(12) United States Patent
Vankayalapati et al.

(10) Patent No.: US 9,266,838 B2
(45) Date of Patent: *Feb. 23, 2016

(54) SUBSTITUTED (E)-N'-(1-PHENYLETHYLIDENE) BENZOHYDRAZIDE ANALOGS AS HISTONE DEMETHYLASE INHIBITORS

(71) Applicants: Hariprasad Vankayalapati, Draper, UT (US); Venkataswamy Sorna, Salt Lake City, UT (US); Steven L. Warner, Sandy, UT (US); Bret Stephens, Riverton, UT (US); David J. Bearss, Alpine, UT (US); Sunil Sharma, Salt Lake City, UT (US)

(72) Inventors: Hariprasad Vankayalapati, Draper, UT (US); Venkataswamy Sorna, Salt Lake City, UT (US); Steven L. Warner, Sandy, UT (US); Bret Stephens, Riverton, UT (US); David J. Bearss, Alpine, UT (US); Sunil Sharma, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 79 days.

This patent is subject to a terminal disclaimer.

(21) Appl. No.: 13/921,895

(22) Filed: Jun. 19, 2013

(65) Prior Publication Data

US 2014/0163017 A1 Jun. 12, 2014

Related U.S. Application Data

(63) Continuation-in-part of application No. 13/586,603, filed on Aug. 15, 2012, now Pat. No. 8,987,335.

(60) Provisional application No. 61/523,801, filed on Aug. 15, 2011.

(51) Int. Cl.

| C07D 231/12 | (2006.01) |
|---|---|
| C07C 251/86 | (2006.01) |
| C07C 311/16 | (2006.01) |
| C07C 311/37 | (2006.01) |
| C07D 207/48 | (2006.01) |
| C07D 213/61 | (2006.01) |
| C07D 213/71 | (2006.01) |
| C07D 213/53 | (2006.01) |
| C07D 213/81 | (2006.01) |
| C07D 295/26 | (2006.01) |

(52) U.S. Cl.
CPC ............ *C07D 231/12* (2013.01); *C07C 251/86* (2013.01); *C07C 311/16* (2013.01); *C07C 311/37* (2013.01); *C07D 207/48* (2013.01); *C07D 213/53* (2013.01); *C07D 213/61* (2013.01); *C07D 213/71* (2013.01); *C07D 213/81* (2013.01); *C07D 295/26* (2013.01)

(58) Field of Classification Search
CPC .. C07C 251/86; C07C 311/16; C07C 311/37; C07D 207/48; C07D 213/53; C07D 216/61; C07D 213/71; C07D 213/81; C07D 231/12
See application file for complete search history.

(56) References Cited

U.S. PATENT DOCUMENTS

| 2004/0110963 | A1 | 6/2004 | Burri et al. |
|---|---|---|---|
| 2006/0167009 | A1 | 7/2006 | Jolidon et al. |
| 2007/0042997 | A1 | 2/2007 | Itai et al. |
| 2007/0207093 | A1 | 9/2007 | Bryant et al. |
| 2008/0214495 | A1 | 9/2008 | Alstermark et al. |
| 2008/0269206 | A1 | 10/2008 | Russell et al. |
| 2009/0247641 | A1 | 10/2009 | Morgan |
| 2010/0048638 | A1 | 2/2010 | Crawford et al. |
| 2010/0130564 | A1 | 5/2010 | Melnick et al. |
| 2010/0247543 | A1 | 9/2010 | Maes et al. |
| 2011/0189306 | A1 | 8/2011 | Kartner et al. |
| 2012/0010075 | A1 | 1/2012 | Young et al. |
| 2012/0148682 | A1* | 6/2012 | Young et al. .................. 424/638 |
| 2012/0232052 | A1 | 9/2012 | Yamagishi et al. |

FOREIGN PATENT DOCUMENTS

| EP | 2107908 A2 | 10/2009 |
|---|---|---|
| WO | 2006/136008 A1 | 12/2006 |
| WO | 2012/062704 A1 | 5/2012 |
| WO | 2013/025805 A1 | 2/2013 |

OTHER PUBLICATIONS

Patani et al. "Bioisosterism: A Rational Approach in Drug Design", Chem. Rev., 1996, vol. 96, pp. 3147-3176.*

Sheridan, R.P. "The Most Common Chemical Replacements in Drug-Like Compounds" J. Chem. Inf. Comput. Sci., 2002, vol. 42, pp. 103-108.*

J. G. Cannon Chapter Nineteen in Burger's Medicinal Chemistry and Drug Discovery, Fifth Edition, vol. I: Principles and Practice, Wiley-Interscience 1995, pp. 783-802, 784.*

(Continued)

*Primary Examiner* — Kendra D Carter
(74) *Attorney, Agent, or Firm* — Wood, Phillips, Katz, Clark & Mortimer

(57) ABSTRACT

In one aspect, the invention relates to substituted (E)-N'-(1-phenylethylidene)benzohydrazide analogs, derivatives thereof, and related compounds, which are useful as inhibitors of lysine-specific histone demethylase, including LSD1; synthetic methods for making the compounds; pharmaceutical compositions comprising the compounds; and methods of using the compounds and compositions to treat disorders associated with dysfunction of the LSD1. This abstract is intended as a scanning tool for purposes of searching in the particular art and is not intended to be limiting of the present invention.

8 Claims, No Drawings

(56) References Cited

OTHER PUBLICATIONS

Nicola et al. "Discovery of novel inhibitors targeting enoyl-acyl carrier protein reductase in Plasmodium falciparum by structure-based virtual screening" Biochemical and Biophysical Research Communications, 2007, vol. 358, pp. 686-691.*

Smirnov et al. "Synthesis and Diruetic Activity of 3-sulfamoyl-4-chlorobenzoyl hydrazones of carbonyl compounds" Zhimiko-Farmatsevticheskiy Zhurnal, 1996, vol. 30, No. 7, pp. 25-26.*
Translation of Smirnov et al. reference, Nov. 2014, pp. 1-9.*
International Search Report and Written Opinion for corresponding PCT Application No. PCT/US14/43179 mailed Oct. 23, 2014.

* cited by examiner

```
                          SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: HMOX_F primer

<400> SEQUENCE: 1
aactttcaga agggccaggt                                              20

<210> SEQ ID NO 2
<211> LENGTH: 20
<212> TYPE: DNA
<213> ORGANISM: Artificial Sequence
<220> FEATURE:
<223> OTHER INFORMATION: HMOX_R primer

<400> SEQUENCE: 2
gtagacaggg gcgaagactg                                              20

<210> SEQ ID NO 3
<211> LENGTH: 22
<212> TYPE: DNA
<213> ORGANISM: Artificial Sequence
<220> FEATURE:
<223> OTHER INFORMATION: HPRT_F primer

<400> SEQUENCE: 3
tgctgaggat ttggaaaggg tg                                           22

<210> SEQ ID NO 4
<211> LENGTH: 22
<212> TYPE: DNA
<213> ORGANISM: Artificial Sequence
<220> FEATURE:
<223> OTHER INFORMATION: HPRT_R primer

<400> SEQUENCE: 4
ccttgagcac acagagggct ac                                           22

<210> SEQ ID NO 5
<211> LENGTH: 20
<212> TYPE: DNA
<213> ORGANISM: Artificial Sequence
<220> FEATURE:
<223> OTHER INFORMATION: B-Actin_F primer

<400> SEQUENCE: 5
ctggaacggt gaaggtgaca                                              20

<210> SEQ ID NO 6
<211> LENGTH: 23
<212> TYPE: DNA
<213> ORGANISM: Artificial Sequence
<220> FEATURE:
<223> OTHER INFORMATION: B-Actin_R primer

<400> SEQUENCE: 6
aagggacttc ctgtaacaac gca                                          23
```

SUBSTITUTED (E)-N'-(1-PHENYLETHYLIDENE)BENZOHYDRAZIDE ANALOGS AS HISTONE DEMETHYLASE INHIBITORS

BACKGROUND

Over the past decade it has become clear that epigenetic changes, which alter gene activity without altering DNA sequence, collaborate with genetic mistakes to promote cancer development and progression (Tsai, H. C. and Baylin, S. B. *Cell Res* 2011, 21 (3), 502-17; and Fullgrabe, J., Kavanagh, E., and Joseph, B. *Oncogene* 2011). The regulation of the modifications on DNA and the proteins associated with DNA has become an area of intense interest and the enzymes involved in these processes have been suggested as a new class of protein targets for drug development. The major proteins associated with DNA are histone proteins. Histone tails are subject to a variety of posttranslational modifications, such as phosphorylation, acetylation, methylation, and ubiquitination, and these modifications, especially acetylation and methylation on lysine residues, play a major role in the regulation of gene expression, and are often dysregulated in cancer (Fullgrabe, J., Kavanagh, E., and Joseph, B. *Oncogene* 2011).

Recently an enzyme called Lysine-Specific Demethylase 1 (LSD1) was found to catalyze the oxidative demethylation of monomethylated and dimethylated histone H3 at lysine 4 (H3K4me1 and H3K4me2) and lysine 9 (H3K9me1 and H3K9me2) through a flavin adenine dinucleotide (FAD)-dependent reaction (Shi, Y., et al. *Cell* 2004, 119 (7), 941-53; and Metzger, E., et al. *Nature* 2005, 437 (7057), 436-9). Whereas histone acetylation is associated with loose chromatin and gene activation, methylation of histones is less straightforward. Using the lysine residues regulated by LSD1 as an example, methylation at H3K4 is generally associated with gene activation, while methylation of H3K9 is associated with transcriptional repression.

There is currently one known mammalian homolog of LSD1 which is a protein variously designated LSD2, KDM1b, and AOF1. It shares a similar domain homology, but exhibits less than 31% sequence identity (Fang, R. et al. *Molecular Cell* 2010, 39:222-233). It has been shown that LSD2 is a H3K4me1/2 demethylase that specifically regulates histone H3K4 methylation within intragenic regions of its target genes (ibid.). Both LSD1 and LSD2 contain a SWIRM domain, a FAD coenzyme-binding motif, and a C-terminal amine oxidase domain, all of which are critical to the enzymatic activity. However, unlike LSD1, the protein LSD2 contains a CW-type zinc finger domain in its N-terminal domain, a region which is unstructured in LSD1. Furthermore, LSD2 lacks the "tower domain" of LSD1. At a cellular level, it has been suggested that LSD2 has a role in transcriptional regulation (ibid.). As expected, LSD2 appears to play a role in regulating DNA methylation as well, although the role in DNA methylation may be developmental stage specific (ibid.; Ciccone, D. N., et al. *Nature* 2009 461:415-418; Karytinos, A., et al. *J. Biol. Chem.* 2009 284:17775-17782; and Yang, Z., et al. *Cell Res.* 2010 20:276-287).

Several lines of evidence point to LSD1 as being a possible therapeutic target in cancer. LSD1 is reportedly over-expressed in a variety of tumors including neuroblastoma, ER-negative breast, bladder, lung, and colorectal tumors (Schulte, J. H., et al. *Cancer Res* 2009, 69 (5), 2065-71; Lim, S., et al. *Carcinogenesis* 2010, 31 (3), 512-20; and Hayami, S., et al. *Int J Cancer* 2011, 128 (3), 574-86). Increased methylation of the permissive H3K4 mark by LSD1 inhibition has been shown to reactivate expression of tumor suppressor genes in cancer models (Huang, Y., et al. *Clin Cancer Res* 2009, 15 (23), 7217-28). In addition, LSD1 has been found to associate with estrogen and androgen receptors leading to the specific demethylation of the repressive H3K9 mark, thereby increasing target gene expression (Metzger, E., et al. *Nature* 2005, 437 (7057), 436-9; and Garcia-Bassets, I., et al. *Cell* 2007, 128 (3), 505-18). Thus, depending upon cofactors bound to LSD1, demethylation by LSD1 can contribute to cancer through both the permissive H3K4 and the repressive H3K9 mark. Therefore, the inhibition of LSD1 might be an effective strategy for re-expression of epigenetically silenced tumor suppressor genes as well as down regulation of important cancer pathways in a number of cancer types. Several LSD1 inhibitors have been reported, but they have shown poor selectivity and/or pharmacological properties, making further exploration of LSD1 biology difficult.

Monoamine oxidase (MAO) inhibitors such as tranylcypromine and pargyline have been reported as LSD1 inhibitors, and there have been several reports regarding attempts to discover derivatives with increased selectivity for LSD1 over MAO (Mimasu, S., et al. *Biochemistry* 2010, 49 (30), 6494-503; Binda, C., et al. *J Am Chem Soc* 2010, 132 (19), 6827-33; Culhane, J. C., et al. *J Am Chem Sac* 2006, 128 (14), 4536-7; Culhane, J. C., et al. *J Am Chem Soc* 2010, 132 (9), 3164-76; and Ueda, R., et al. *J Am Chem Soc* 2009, 131 (48), 17536-7). These compounds irreversibly inactivate LSD1 by covalent binding to the FAD cofactor. Polyamine derivatives have also been evaluated as LSD1 inhibitors, where compounds with activity in the μM range have been described (Huang, Y., et al. *Clin Cancer Res* 2009, 15 (23), 7217-28; Sharma, S. K., et al. *J Med Chem* 2010, 53 (14), 5197-212; and Huang, Y., et al. *Proc Natl Acad Sci USA* 2007, 104 (19), 8023-8). In general, these and other reported LSD1 inhibitors are neither adequately selective nor potent enough to optimally interact with the crucial amino acid residues of the substrate-binding site present in LSD1.

In summary, the LSD proteins play a key role in epigenetic and transcriptional regulation, and they are frequently altered in mammalian cancers, thus making them an attractive target for therapeutic intervention. Despite advances in drug discovery directed to identifying inhibitors of LSD1 and/or LSD2 protein activity, there is still a scarcity of compounds that are both potent, efficacious, and selective inhibitors of either LSD1 or LSD2. Furthermore, there is a scarcity of compounds effective in the treatment of cancer and other diseases associated with dysfunction in LSD1 and/or LSD2. These needs and other needs are satisfied by the present invention.

SUMMARY

In accordance with the purpose(s) of the invention, as embodied and broadly described herein, the invention, in one aspect, relates to compounds useful as inhibitors of lysine-specific demethylase, or LSD. In a further aspect, the disclosed compounds and products of disclosed methods of making, or a pharmaceutically acceptable salt, hydrate, solvate, or polymorph thereof, are modulators of LSD activity, methods of making same, pharmaceutical compositions comprising same, and methods of treating disorders associated with a LSD activity dysfunction using same. In a still further aspect, the present invention relates to compounds that bind to a LSD protein and negatively modulate LSD activity. The disclosed compounds can, in one aspect, exhibit subtype selectivity. In a further aspect, the disclosed compounds exhibit selectivity for the LSD1 member of the LSD protein family. In a still further aspect, the disclosed compounds exhibit selectivity for the LSD2 member of the LSD protein family.

Also disclosed are pharmaceutical compositions comprising, a therapeutically effective amount of a disclosed compound and a pharmaceutically acceptable carrier.

Also disclosed are synthetic methods for making the disclosed compounds. In a further aspect, disclosed are the products of the disclosed synthetic methods.

Disclosed are methods for the treatment of a disorder associated with a LSD activity dysfunction in a mammal comprising the step of administering to the mammal a therapeutically effective amount of a disclosed compound, or a pharmaceutically acceptable salt, hydrate, solvate, or polymorph thereof.

Also disclosed are methods for inhibition of LSD activity in a mammal comprising the step of administering to the mammal a therapeutically effective amount of least one disclosed compound, or a pharmaceutically acceptable salt, hydrate, solvate, or polymorph thereof.

Also disclosed are methods for inhibiting LSD activity in at least one cell, comprising the step of contacting the at least one cell with an effective amount of least one disclosed compound, or a pharmaceutically acceptable salt, hydrate, solvate, or polymorph thereof.

Also disclosed are uses of a disclosed compound, or a pharmaceutically acceptable salt, hydrate, solvate, or polymorph thereof. In a further aspect, the invention relates to pharmaceutical compositions comprising a pharmaceutically acceptable carrier and an effective amount of a disclosed compound, or a pharmaceutically acceptable salt, hydrate, solvate, or polymorph thereof.

Also disclosed are kits comprising at least one disclosed compound, or a pharmaceutically acceptable salt, hydrate, solvate, or polymorph thereof, and one or more of: (a) at least one agent known to increase histone demethylase activity; (b) at least one agent known to decrease histone demethylase activity; (c) at least one agent known to treat a disorder of uncontrolled cellular proliferation; (d) at least one agent known to treat a neurodegenerative disorder; (e) instructions for treating a neurodegenerative disorder; or (f) instructions for treating a disorder associated with uncontrolled cellular proliferation.

Also disclosed are methods for manufacturing a medicament comprising, combining at least one disclosed compound or at least one disclosed product with a pharmaceutically acceptable carrier or diluent. In a further aspect, the invention relates to the use of a disclosed compound in the manufacture of a medicament for the treatment of a disorder associated with a LSD activity dysfunction. In a yet further aspect, the LSD activity dysfunction is a LSD1 activity dysfunction. In an even further aspect, the LSD activity dysfunction is a LSD2 activity dysfunction. In a still further aspect, the invention relates to the used of disclosed compound in the manufacture of a medicament for the treatment of a disorder of uncontrolled cellular proliferation.

Also disclosed are uses of a disclosed compound or a disclosed product in the manufacture of a medicament for the treatment of a disorder associated with a LSD dysfunction in a mammal.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. DEFINITIONS

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as ChemDraw™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the term "LSD" refers collectively to either or both LSD1 and LSD2.

As used herein, the terms "LSD1" and "lysine-specific demethylase 1" can be used interchangeably and refer to a histone demethylase encoded by the KDM1A gene. The KDM1A gene has a gene map locus of 1p36.12 as described by the Entrez Gene cytogenetic band, Ensembl cytogenetic band, and the HGNC cytogenetic band. The term LSD1 refers to a native protein that has 852 amino acids with a molecular weight of about 92903 Da, and is a member of the flavin monoamine oxidase family. The term LSD1 is inclusive of the protein, gene product and/or gene referred to by such alternative designations as: LSD1, KDM1; RP1-184J9.1; AOF2; BHC110; KIAA0601; LSD1; BRAF35-HDAC complex protein BHC110; FAD-binding protein BRAF35-HDAC complex, 110 kDa subunit; amine oxidase (flavin containing) domain 2; lysine-specific histone demethylase 1; lysine-specific histone demethylase 1A; flavin-containing amine oxidase domain-containing protein 2; lysine (K)-specific demethylase 1; amine oxidase (flavin containing) domain 2; and FAD-binding protein BRAF35-HDAC complex, 110 kDa subunit, as used by those skilled in the art.

As used herein, the terms "LSD2 and "lysine-specific demethylase 2 can be used interchangeably and refer to a histone demethylase encoded by the KDM1B gene. The KDM1B gene has a gene map locus of 6p22.3 as described by the Entrez Gene cytogenetic band, Ensembl cytogenetic band, and the HGNC cytogenetic band. The term LSD21 refers to a native protein that has 822 amino acids with a molecular weight of about 92098 Da, and is a member of the flavin monoamine oxidase family. The term LSD2 is inclusive of the protein, gene product and/or gene referred to by such alternative designations as: LSD2, AOF1; FLJ33898; FLJ34109; FLJ43328; C6orf193; DKFZp686I0412; OTTHUMP00000179125; bA204B7.3; dJ298J15.2; flavin-containing amine oxidase domain-containing protein 1; lysine-specific histone demethylase 2; lysine (K)-specific demethylase 1B; amine oxidase (flavin containing) domain 1; amine oxidase, flavin containing 1; lysine-specific histone demethylase 2; chromosome 6 open reading frame 193; and lysine-specific histone demethylase 1B, as used by those skilled in the art.

As used herein, the term "histone demethylase" refers to that group of enzymes which remove methyl groups from histone proteins. The term is inclusive of both histone lysine demethylases, i.e. enzymes which remove methyl groups from lysine residues in histones, and histone arginine demethylases, i.e. enzymes which remove methyl groups from arginine residues in histones.

As used herein, the term "histone lysine demethylase" or "lysine-specific histone demethylase" can be used interchangeably, and both refer to that group of enzymes which remove methyl groups from lysine residues of histone proteins. The histone lysine demethylases are a group of enzymes which comprise the following specific forms: LSD1, LSD2, JMJD2A, JMJD2B, JMJD2C and JMJD2D.

As used herein, the terms "optional" or "optionally" means that the subsequently described event or circumstance can or can not occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of a disorder of uncontrolled cellular proliferation associated with a histone lysine demethylase dysfunction prior to the administering step. In some aspects of the disclosed method, the subject has been diagnosed with a need for inhibition of a histone lysine demethylase prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, zebra fish etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder of uncontrolled cellular proliferation" means having been subjected to a physical examination by a person of skill, for example, a physician, and found to have a condition that can be diagnosed or treated by a compound or composition that can inhibit a histone lysine demethylase. As a further example, "diagnosed with a need for inhibition of a histone demethylase" refers to having been subjected to a physical examination by a person of skill, for example, a physician, and found to have a condition characterized by a histone demethylase dysfunction. Such a diagnosis can be in reference to a disorder, such as a disorder of uncontrolled cellular proliferation, cancer and the like, as discussed herein. For example, the term "diagnosed with a need for inhibition of histone demethylase activity" refers to having been subjected to a physical examination by a person of skill, for example, a physician, and found to have a condition that can be diagnosed or treated by inhibition of histone demethylase activity. For example, "diagnosed with a need for treatment of one or more disorders of uncontrolled cellular proliferation associated with a histone demethylase dysfunction" means having been subjected to a physical examination by a person of skill, for example, a physician, and found to have one or more disorders of uncontrolled cellular proliferation associated with a histone demethylase dysfunction.

As used herein, the phrase "identified to be in need of treatment for a disorder," or the like, refers to selection of a subject based upon need for treatment of the disorder. For example, a subject can be identified as having a need for treatment of a disorder (e.g., a disorder related to a dysfunction of histone demethylase activity) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, intraurethral administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target receptor, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex, and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "$EC_{50}$," is intended to refer to the concentration of a substance (e.g., a compound or a drug) that is required for 50% agonism or activation of a biological process, or component of a process, including a protein, subunit, organelle, ribonucleoprotein, etc. In one aspect, an $EC_{50}$ can refer to the concentration of a substance that is required for 50% agonism or activation in vivo, as further defined elsewhere herein. In a further aspect, $EC_{50}$ refers to the concentration of agonist or activator that provokes a response halfway between the baseline and maximum response.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. For example, an $IC_{50}$ can refer to the concentration of a substance that is required for 50% inhibition in vivo or the inhibition is measured in vitro, as further defined elsewhere herein. Alternatively, $IC_{50}$ refers to the half maximal (50%) inhibitory concentration (IC) of a substance The inhibition can be measured in a cell-line such as AN3 CA, BT-20, BT-549, HCT 116, HER218, MCF7, MDA-MB-231, MDA-MB-235, MDA-MB-435S, MDA-MB-468, PANC-1, PC-3, SK-N-MC, T-47D, and U-87 MG. In a yet further aspect, the inhibition is measured in a cell-line, e.g. HEK-293 or HeLa, transfected with a mutant or wild-type mammalian histone demethylase, e.g. LSD1 or LSD2.

The term "pharmaceutically acceptable" describes a material that is not biologically or otherwise undesirable, i.e., without causing an unacceptable level of undesirable biological effects or interacting in a deleterious manner.

The term "stable," as used herein, refers to compounds that are not substantially altered when subjected to conditions to allow for their production, detection, and, in certain aspects, their recovery, purification, and use for one or more of the purposes disclosed herein.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

For example, a "C1-C3 alkyl" group can be selected from methyl, ethyl, n-propyl, i-propyl, and cyclopropyl, or from a subset thereof. In certain aspects, the "C1-C3 alkyl" group can be optionally further substituted. As a further example, a "C1-C4 alkyl" group can be selected from methyl, ethyl, n-propyl, i-propyl, cyclopropyl, n-butyl, i-butyl, s-butyl, t-butyl, and cyclobutyl, or from a subset thereof. In certain aspects, the "C1-C4 alkyl" group can be optionally further substituted. As a further example, a "C1-C6 alkyl" group can be selected from methyl, ethyl, n-propyl, i-propyl, cyclopropyl, n-butyl, i-butyl, s-butyl, t-butyl, cyclobutyl, n-pentyl, i-pentyl, s-pentyl, t-pentyl, neopentyl, cyclopentyl, n-hexyl, i-hexyl, 3-methylpentane, 2,3-dimethylbutane, neohexane, and cyclohexane, or from a subset thereof. In certain aspects, the "C1-C6 alkyl" group can be optionally further substituted. As a further example, a "C1-C8 alkyl" group can be selected from methyl, ethyl, n-propyl, i-propyl, cyclopropyl, n-butyl, i-butyl, s-butyl, t-butyl, cyclobutyl, n-pentyl, i-pentyl, s-pentyl, t-pentyl, neopentyl, cyclopentyl, n-hexyl, i-hexyl, 3-methylpentane, 2,3-dimethylbutane, neohexane, cyclohexane, heptane, cycloheptane, octane, and cyclooctane, or from a subset thereof. In certain aspects, the "C1-C8 alkyl" group can be optionally further substituted. As a further example, a "C1-C12 alkyl" group can be selected from methyl, ethyl, n-propyl, i-propyl, cyclopropyl, n-butyl, i-butyl, s-butyl, t-butyl, cyclobutyl, n-pentyl, i-pentyl, s-pentyl, t-pentyl, neopentyl, cyclopentyl, n-hexyl, i-hexyl, 3-methylpentane, 2,3-dimethylbutane, neohexane, cyclohexane, heptane, cycloheptane, octane, cyclooctane, nonane, cyclononane, decane, cyclodecane, undecane, cycloundecane, dodecane, and cyclododecane, or from a subset thereof. In certain aspects, the "C1-C12 alkyl" group can be optionally further substituted.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, nitrile, sulfonamide, or thiol as described herein.

The term "polyalkylene group" as used herein is a group having two or more $CH_2$ groups linked to one another. The polyalkylene group can be represented by the formula $—(CH_2)_a—$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $—OA^1$ where $A^1$ is alkyl or cycloalkyl as defined above. "Alkoxy" also includes polymers of alkoxy groups as just described; that is, an alkoxy can be a polyether such as $—OA^1-OA^2$ or $—OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol $C=C$. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, nitrite, sulfonamide, or thiol, as described herein.

The term "cycloalkenyl" as used herein is a non-aromatic carbon-based ring composed of at least three carbon atoms and containing at least one carbon-carbon double bound, i.e., $C=C$. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, nitrile, sulfonamide, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, nitrile, sulfonamide, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, nitrile, sulfonamide, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, nitrile, sulfonamide, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halogen," "halide," and "halo," as used herein, refer to the halogens fluorine, chlorine, bromine, and iodine. It is also contemplated that, in various aspects, halogen can be selected from fluoro, chloro, bromo, and iodo. For example, halogen can be selected from fluoro, chloro, and bromo. As a further example, halogen can be selected from fluoro and chloro. As a further example, halogen can be selected from chloro and bromo. As a further example, halogen can be selected from bromo and iodo. As a further example, halogen can be selected from chloro, bromo, and iodo. In one aspect, halogen can be fluoro. In a further aspect, halogen can be chloro. In a still further aspect, halogen is bromo. In a yet further aspect, halogen is iodo.

It is also contemplated that, in certain aspects, pseudohalogens (e.g. triflate, mesylate, tosylate, brosylate, etc.) can be used in place of halogens. For example, in certain aspects, halogen can be replaced by pseudohalogen. As a further example, pseudohalogen can be selected from triflate, mesylate, tosylate, and brosylate. In one aspect, pseudohalogen is triflate. In a further aspect, pseudohalogen is mesylate. In a further aspect, pseudohalogen is tosylate. In a further aspect, pseudohalogen is brosylate.

The term "heterocycle," as used herein refers to single and multi-cyclic aromatic or non-aromatic ring systems in which at least one of the ring members is other than carbon. Heterocycle includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —Si$A^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)$A^1$, —S(O)$_2A^1$, —OS(O)$_2A^1$, or —OS(O)$_2$O$A^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A', where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula A'S(O)$_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1$S(O)$A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

Suitable monovalent substituents on a substitutable carbon atom of an "optionally substituted" group are independently halogen; —$(CH_2)_{0-4}R^\circ$; —$(CH_2)_{0-4}OR^\circ$; —$O(CH_2)_{0-4}R^\circ$, —O—$(CH_2)_{0-4}(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$(CH_2)_{0-4}O(CH_2)_{0-1}$-pyridyl which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR$—, $SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(C_{1-4}$ straight or branched)alkylene)O—$N(R^\circ)_2$; or —$(C_{1-4}$ straight or branched alkylene)C(O)O—$N(R^\circ)_2$, wherein each $R^\circ$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^\bullet$; -(halo$R^\bullet$), —$(CH_2)_{0-2}OH$, —$(CH_2)_{0-2}OR^\bullet$), —$(CH_2)_{0-2}CH(OR^\bullet)_2$; —$O(haloR^\bullet)$, —CN, —$N_3$, —$(CH_2)_{0-2}C(O)R^\bullet$), —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —$(C_{1-4}$ straight or branched alkylene)C(O)OR$^\bullet$, or —$SSR^\bullet$ wherein each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =$NNR^*_2$, =$NNHC(O)R^*$, =$NNHC(O)OR^*$, =$NNHS(O)_2R^*$, =$NR^*$, =$NOR^*$, —$O(C(R^*_2))_{2-3}O$—, or —$S(C(R^*_2))_{2-3}S$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of $R^*$ is selected from hydrogen, $C_{4-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, —$R^\bullet$, -(halo$R^\bullet$), —OH, —$OR^\bullet$, —$O(haloR^\bullet)$, —CN, —C(O)OH, —$C(O)OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^\dagger$, $NR^\dagger_2$, —$C(O)R^\dagger$, —$C(O)OR^\dagger$, —$C(O)C(O)R^\dagger$, —$C(O)CH_2C(O)R^\dagger$, —$S(O)_2R^\dagger$, —$S(O)_2NR^\dagger_2$, —$C(S)NR^\dagger_2$, —$C(NH)NR^\dagger_2$, or —$N(R^\dagger)S(O)_2R^\dagger$; wherein each $R^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, —$R^\bullet$, -(halo$R^\bullet$), —OH, —$OR^\bullet$, —$O(haloR^\bullet)$, —ON, —C(O)OH, —$C(O)OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides—including chloro, bromo, and iodo—and pseudohalides (sulfonate esters)—including triflate, mesylate, tosylate, and brosylate. It is also contemplated that a hydroxyl moiety can be converted into a leaving group via Mitsunobu reaction.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, *Protective Groups in Organic Synthesis*, T. W. Greene, P. G. M. Wuts, Wiley-Interscience, 1999).

The term "protecting group" means a group which protects one or more functional groups of a compound giving rise to a protected derivative of the specified compound. Functional groups which may be protected include, by way of example, amino groups, hydroxyl groups, and the like. Protecting groups are well-known to those skilled in the art and are described, for example, in T. W. Greene and G. M. Wuts, *Protective Groups in Organic Synthesis*, Third Edition, Wiley, New York, 1999, and references cited therein.

The term "amino-protecting group" means a protecting group suitable for preventing undesired reactions at an amino group, include, but are not limited to, tert-butoxycarbonyl (BOC), trityl (Tr), benzyloxycarbonyl (Cbz), 9-fluorenylmethoxycarbonyl (FMOC), formyl, trimethylsilyl (TMS), tert-butyldimethylsilyl (TBS), benzyl, p-methoxybenzyl, p-fluorobenzyl, p-chlorobenzyl, p-bromobenzyl, diphenylmethyl naphtylmethyl, tetrahydropyran (THP), and the like.

The term "hydroxyl-protecting group" means a protecting group suitable for preventing undesirable reactions at a hydroxyl group. Representative hydroxyl-protecting groups include, but are not limited to, silyl groups including tri(1-6C)-alkylsilyl groups, such as trimethylsilyl (TMS), triethylsilyl (TES), tert-butyldimethylsilyl (TBS), and the like; esters (acyl groups) including (1-6C)-alkanoyl groups, such as formyl, acetyl, and the like; arylmethyl groups, such as benzyl (Bn), p-methoxybenzyl (PMB), 9-fluorenylmethyl (Fm), diphenylmethyl (benzhydryl, DPM), tetrahydropyran (THP), methoxylmethyl (MOM), methylthiomethyl (MTM), benzyloxymethyl (BOM), and the like.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

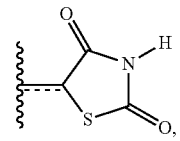

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture.

Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., *The Royal Society of Chemistry*, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

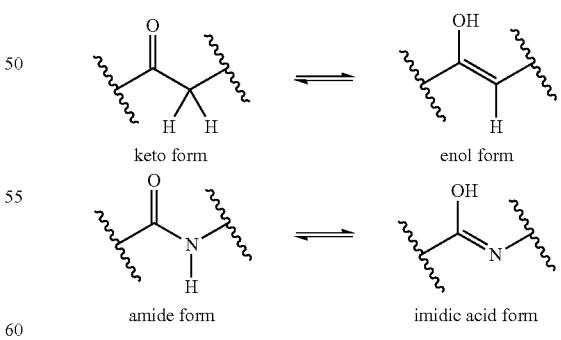

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

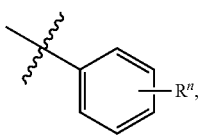

which is understood to be equivalent to a formula:

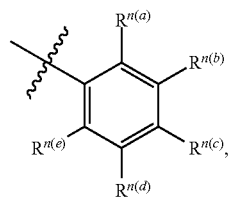

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Sigma-Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as *Fieser and Fieser's Reagents for Organic Synthesis*, Volumes 1-17 (John Wiley and Sons, 1991); *Rodd's Chemistry of Carbon Compounds*, Volumes 1-5 and Supplementals (Elsevier Science Publishers, 1989); *Organic Reactions*, Volumes 1-40 (John Wiley and Sons, 1991); March's *Advanced Organic Chemistry*, (John Wiley and Sons, 4th Edition); and Larock's *Comprehensive Organic Transformations* (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

In one aspect, the invention relates to compounds useful as inhibitors of histone demethylase. In a further aspect, the compounds are useful as inhibitors of lysine-specific histone demethylase ("LSD"). Moreover, in one aspect, the compounds of the invention are useful in the treatment of disorders of uncontrolled cellular proliferations. In a further aspect, the disorder of uncontrolled cellular proliferation is a cancer or a tumor. In a still further aspect, the disorder of uncontrolled cellular proliferation is associated with a LSD dysfunction, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, the invention relates to a compound having a structure represented by formula (I)

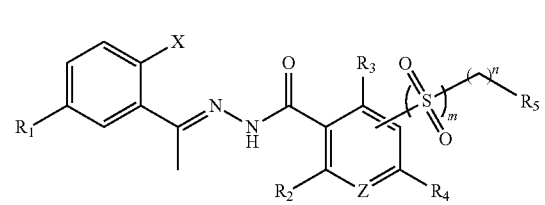

(I)

or a formula (II)

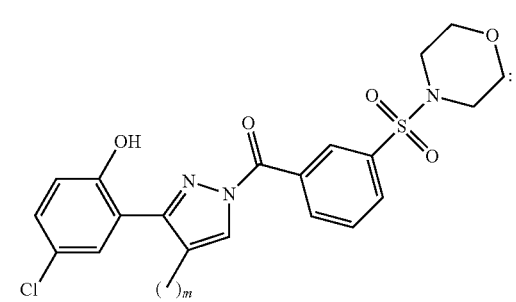

(II)

wherein m is 0 or 1;

n is an integer from 0 to 3;

X is selected from the group consisting of OH, $NO_2$ and F;

Z is selected from the group consisting of N and CH;

$R_1$ is selected from the group consisting of halo, C1-C3 haloalkyl, and C1-C3 polyhaloalkyl;

each of $R_2$, $R_3$, and $R_4$ is independently selected from the group consisting of hydrogen, halo, hydroxyl, cyano, amino, C2-C6 alkalkoxy, C1-C6 alkoxy, C1-C6 alkyl, C1-C6 polyhaloalkyl, and C1-C6 haloalkyl;

$R_5$ is selected from the group consisting of $NR_6R_7$, C1-C6 alkyl, C3-C6 cycloalkyl,

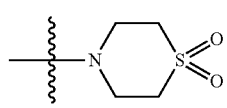

and Cy, and substituted with 0-3 groups independently selected from halo, hydroxyl, amino, C2-C6 alkalkoxy, C1-C6 alkylalcohol, C1-C6 alkoxy, C1-C6 alkyl, C1-C6 polyhaloalkyl, C1-C6 haloalkyl, C3-C6 cycloalkyl, and Cy;

Cy is a heterocycloalkyl selected from the group consisting of aziridinyl, azetidinyl, pyrrolidinyl, piperidinyl, azepanyl, oxazolidinyl, imidazolidinyl, pyrazolidinyl, piperazinyl, oxazinanyl, morpholinyl, hexahydrophyrimidinyl, and hexahydropyridazinyl; and each of $R_6$ and $R_7$ is independently selected from the group consisting of hydrogen, C1-C6 alkyl, C3-C6 cycloalkyl, and C3-C6 heterocycloalkyl;

or a pharmaceutically acceptable salt thereof.

In some embodiments, the invention provides a compound selected from the group consisting of:

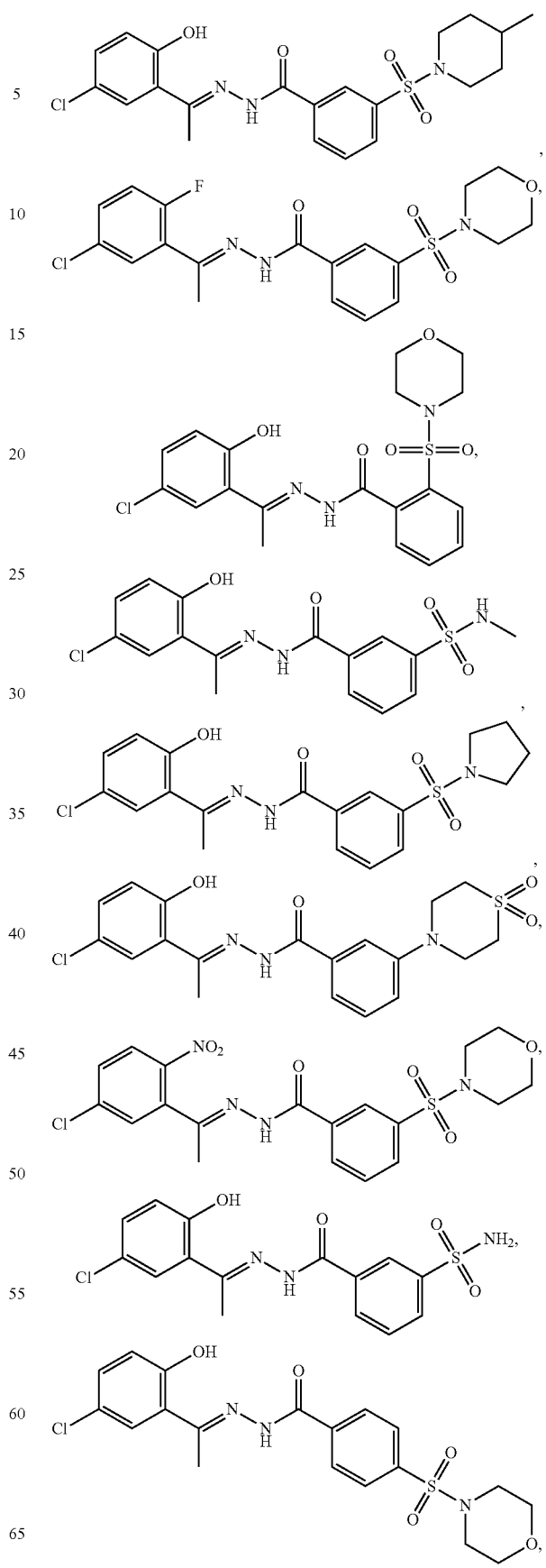

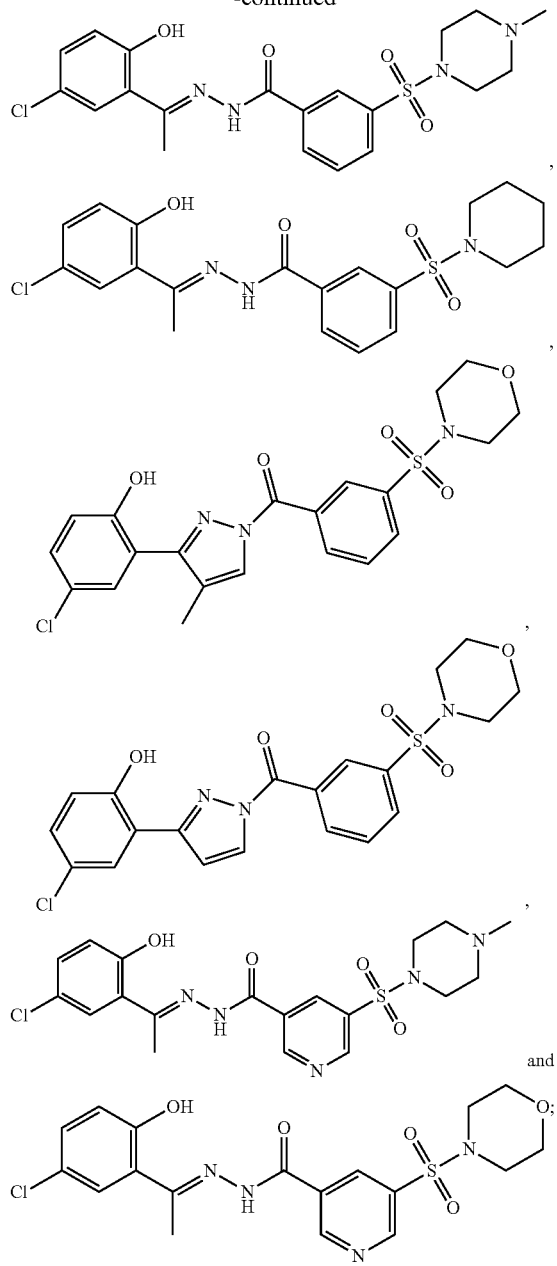

, or a pharmaceutically acceptable salt thereof.

In yet other embodiments, the invention provides a compound having a structure represented by a formula:

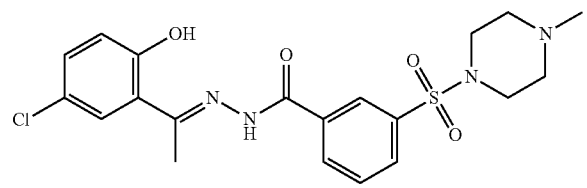

or a pharmaceutically acceptable salt thereof.

In yet other embodiments, the invention provides a compound having a structure represented by a formula:

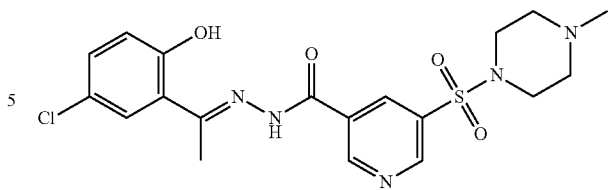

or a pharmaceutically acceptable salt thereof.

The invention also provides a pharmaceutical composition comprising a therapeutically effective amount of any of a compound of the invention and a pharmaceutically acceptable carrier.

The invention also provides a method for the treatment of a disorder of uncontrolled cellular proliferation in a mammal, the method comprising the step of administering to the mammal an effective amount of any of the compounds of the invention.

The invention also provides a method for decreasing histone demethylase activity in a mammal, the method comprising the step of administering to the mammal an effective amount of any of the compounds of the invention.

2. Inhibition of Histone Demethylase Activity

In one aspect, the disclosed compounds exhibit inhibition of LSD protein activity. In a yet further aspect, the disclosed compounds exhibit selective inhibition of LSD1 protein activity. In an even further aspect, the disclosed compounds exhibit selective inhibition of LSD2 protein activity. In a still further aspect, the disclosed compounds inhibit LSD demethylase activity. In a still further aspect, the disclosed compounds exhibit binding to the FAD domain of LSD. In an even further aspect, the disclosed compounds exhibit inhibition of LSD-mediated demethylation of histone 3 (H3) at the Lys4 position. In a still further aspect, the disclosed compounds exhibit inhibition LSD-mediated demethylation of H3K3m1 and H3K4me2. In a yet further aspect, the disclosed compounds exhibit inhibition LSD-mediated demethylation of H3K9me2 and H3K9me1.

In a still further aspect, the disclosed compounds inhibit LSD1 demethylase activity. In a still further aspect, the disclosed compounds exhibit binding to the FAD domain of LSD1. In an even further aspect, the disclosed compounds exhibit inhibition of LSD1-mediated demethylation of histone 3 (H3) at the Lys4 position. In a still further aspect, the disclosed compounds exhibit inhibition LSD1-mediated demethylation of H3K3m1 and H3K4me2. In a yet further aspect, the disclosed compounds exhibit inhibition LSD1-mediated demethylation of H3K9me2 and H3K9me1.

In a still further aspect, the disclosed compounds inhibit LSD2 demethylase activity. In a still further aspect, the disclosed compounds exhibit binding to the FAD domain of LSD2. In an even further aspect, the disclosed compounds exhibit inhibition of LSD2-mediated demethylation of histone 3 (H3) at the Lys4 position. In a still further aspect, the disclosed compounds exhibit inhibition LSD2-mediated demethylation of H3K3m1 and H3K4me2.

In a further aspect, the disclosed compounds exhibit disruption of LSD interaction with a complexes comprising one or more of HDAC1/2, CoREST, CtBP1, BRAF35 and BHC80 proteins. In a still further aspect, the disclosed compounds disrupt binding of LSD1 to one or more proteins selected from HDAC1/2, CoREST, CtBP1, BRAF35 and BHC80 proteins. In a still further aspect, the disclosed compounds disrupt binding of LSD2 to one or more proteins selected from G9a, NSD3, HDAC1/2, CoREST, CtBP1, BRAF35 and BHC80 proteins.

Inhibition of LSD activity can be determined by a variety of both in vitro and in vivo methods known to one skilled in the art. For example, enzymatic activity can be determined in in vitro enzyme assay systems. In various aspects, the enzymatic activity of either LSD1 or LSD2 can be determined in a spectrophometric assay. Briefly, the assay is based on the multistep enzymatic reaction in which LSD1 or LSD2 first produces $H_2O_2$ during the demethylation of lysine 4 on a peptide corresponding to the first 21 amino acids of the N-terminal tail of histone H3. In the presence of horseradish peroxidase, the $H_2O_2$ produced reacts with ADHP to produce the highly fluorescent compound resorufin that can be analyzed with an excitation wavelength of 530-540 nm and an emission wavelength of 585-595 nm. The assay requires a source of LSD1 or LSD2 enzyme, either purified from natural sources (e.g. a tissue or cultured cells), isolated as a recombinantly expressed protein, or as a unpurified protein in whole cell extracts. In one aspect, the disclosed compounds exhibit inhibition of LSD protein activity with an $IC_{50}$ in an EMSA assay of less than about 300 µM, less than about 100 µM, less than about 50 µM, less than about 10 µM, less than about 1 µM, less than about 500 nM, or of less than about 100 nM. In a further aspect, the disclosed compounds exhibit inhibition of LSD1 protein activity with an $IC_{50}$ in an EMSA assay of less than about 300 µM, less than about 100 less than about 50 µM, less than about 10 µM, less than about 1 µM, less than about 500 nM, or of less than about 100 nM. In a still further aspect, the disclosed compounds exhibit inhibition of LSD2 protein activity with an $IC_{50}$ in an EMSA assay of less than about 300 µM, less than about 100 µM, less than about 50 µM, less than about 10 µM, less than about 1 µM, less than about 500 nM, or of less than about 100 nM.

In one aspect, the disclosed compounds are selective for LSD. In a further aspect, selective inhibition of LSD activity is determined using an enzyme assay. In various further aspects, the compound inhibits LSD activity in an enzyme assay with an $IC_{50}$ less than the $IC_{50}$ for MAO A and/or MAO B. That is, a disclosed compound can have selectivity for the LSD protein vis-à-vis MAO A and/or MAO B. For example, in one aspect, a disclosed compound can inhibit LSD with an $IC_{50}$ of about 5-fold less than that for MAO A, of about 10-fold less than that for MAO A, of about 20-fold less than that for MAO A, of about 30-fold less than that for MAO A, of about 50-fold less than that for MAO A, of about 100-fold less than that for MAO A, of about 250-fold less than that for MAO A, of about 500-fold less than that for MAO A, of about 1000-fold less than that for MAO A, and more than about 1000-fold less than that for MAO A. In a further aspect, a disclosed compound can inhibit LSD with an $IC_{50}$ of about 5-fold less than that for MAO B, of about 10-fold less than that for MAO B, of about 20-fold less than that for MAO B, of about 30-fold less than that for MAO B, of about 50-fold less than that for MAO B, of about 100-fold less than that for MAO B, of about 250-fold less than that for MAO B, of about 500-fold less than that for MAO B, of about 1000-fold less than that for MAO B, and more than about 1000-fold less than that for MAO B.

In one aspect, the disclosed compounds are selective for LSD1. In a further aspect, selective inhibition of LSD1 activity is determined using an enzyme assay. In various further aspects, the compound inhibits LSD1 activity in an enzyme assay with an $IC_{50}$ less than the $IC_{50}$ for one or more of LSD2, MAO A, and MAO B. That is, a disclosed compound can have selectivity for the LSD1 protein vis-à-vis one or more of LSD2, MAO A, and MAO B. For example, in one aspect, a disclosed compound can inhibit LSD1 with an $IC_{50}$ of about 5-fold less than that for LSD2, of about 10-fold less than that for LSD2, of about 20-fold less than that for LSD2, of about 30-fold less than that for LSD2, or of about 50-fold less than that for LSD2. In a further aspect, a disclosed compound can inhibit LSD1 with an $IC_{50}$ of about 5-fold less than that for MAO A, of about 10-fold less than that for MAO A, of about 20-fold less than that for MAO A, of about 30-fold less than that for MAO A, of about 50-fold less than that for MAO A, of about 100-fold less than that for MAO A, of about 250-fold less than that for MAO A, of about 500-fold less than that for MAO A, of about 1000-fold less than that for MAO A, and more than about 1000-fold less than that for MAO A. In a further aspect, a disclosed compound can inhibit LSD1 with an $IC_{50}$ of about 5-fold less than that for MAO B, of about 10-fold less than that for MAO B, of about 20-fold less than that for MAO B, of about 30-fold less than that for MAO B, of about 50-fold less than that for MAO B, of about 100-fold less than that for MAO B, of about 250-fold less than that for MAO B, of about 500-fold less than that for MAO B, of about 1000-fold less than that for MAO B, and more than about 1000-fold less than that for MAO B.

In one aspect, the disclosed compounds are selective for LSD2. In a further aspect, selective inhibition of LSD2 activity is determined using an enzyme assay. In various further aspects, the compound inhibits LSD2 activity in an enzyme assay with an $IC_{50}$ less than the $IC_{50}$ for one or more of LSD1, MAO A, and MAO B. That is, a disclosed compound can have selectivity for the LSD2 protein vis-à-vis one or more of LSD1, MAO A, and MAO B. For example, in one aspect, a disclosed compound can inhibit LSD2 with an $IC_{50}$ of about 5-fold less than that for LSD1, of about 10-fold less than that for LSD1, of about 20-fold less than that for LSD1, of about 30-fold less than that for LSD1, or of about 50-fold less than that for LSD1. In a further aspect, a disclosed compound can inhibit LSD2 with an $IC_{50}$ of about 5-fold less than that for MAO A, of about 10-fold less than that for MAO A, of about 20-fold less than that for MAO A, of about 30-fold less than that for MAO A, of about 50-fold less than that for MAO A, of about 100-fold less than that for MAO A, of about 250-fold less than that for MAO A, of about 500-fold less than that for MAO A, of about 1000-fold less than that for MAO A, and more than about 1000-fold less than that for MAO A. In a further aspect, a disclosed compound can inhibit LSD2 with an $IC_{50}$ of about 5-fold less than that for MAO B, of about 10-fold less than that for MAO B, of about 20-fold less than that for MAO B, of about 30-fold less than that for MAO B, of about 50-fold less than that for MAO B, of about 100-fold less than that for MAO B, of about 250-fold less than that for MAO B, of about 500-fold less than that for MAO B, of about 1000-fold less than that for MAO B, and more than about 1000-fold less than that for MAO B.

In various aspects, the disclosed compounds exhibit binding to a LSD protein. In a further aspect, the disclosed compounds exhibit binding to the FAD domain of a LSD protein. In a still further aspect, the disclosed compounds exhibit binding to LSD1 protein. In an even further aspect, the disclosed compounds exhibit binding to LSD2 protein. The binding affinity of a disclosed compound for a LSD protein, e.g. LSD1 protein, can be determined by various methods known to one skilled in the art. In one aspect, the disclosed compounds exhibit binding to LSD protein with a $K_D$ of less than about 50 µM, less than about 10 µM, less than about 1 µM, less than about 500 nM, or of less than about 100 nM. In a further aspect, the $K_D$ is determined using an SPR method.

In a still further aspect, the binding is determined using LSD1 protein. In a yet further aspect, the binding is determined using LSD2 protein.

In various further aspects, the binding to LSD is selective. In a further aspect, the disclosed compounds exhibit a $K_D$ for LSD binding less than the $K_D$ of MAO A and/or MAO B. That is, a disclosed compound can have selectivity for the LSD protein vis-à-vis MAO A and/or MAO B proteins. For example, in one aspect, a disclosed compound can bind LSD with a $K_D$ of about 5-fold less than that for MAO A, of about 10-fold less than that for MAO A, of about 20-fold less than that for MAO A, of about 30-fold less than that for MAO A, of about 50-fold less than that for MAO A, of about 100-fold less than that for MAO A, of about 250-fold less than that for MAO A, of about 500-fold less than that for MAO A, of about 1000-fold less than that for MAO A, and of more than about 1000-fold less than that for MAO A. In a further aspect, a disclosed compound can bind LSD with a $K_D$ of about 5-fold less than that for MAO B, of about 10-fold less than that for MAO B, of about 20-fold less than that for MAO B, of about 30-fold less than that for MAO B, of about 50-fold less than that for MAO B, of about 100-fold less than that for MAO B, of about 250-fold less than that for MAO B, of about 500-fold less than that for MAO B, of about 1000-fold less than that for MAO B, and of more than about 1000-fold less than that for MAO B.

In various further aspects, the binding to LSD1 is selective. In a further aspect, the disclosed compounds exhibit a $K_D$ for LSD1 binding less than the $K_D$ for one or more of LSD2, MAO A, and MAO B. That is, a disclosed compound can have selectivity for the LSD1 protein vis-à-vis one or more of LSD2, MAO A, and MAO B proteins. For example, in one aspect, a disclosed compound can bind LSD1 with a $K_D$ of about 5-fold less than that for LSD2, of about 10-fold less than that for LSD2, of about 20-fold less than that for LSD2, of about 30-fold less than that for LSD2, or about 50-fold less than that for LSD2. In a further aspect, a disclosed compound can bind LSD1 with a $K_D$ of about 5-fold less than that for MAO A, of about 10-fold less than that for MAO A, of about 20-fold less than that for MAO A, of about 30-fold less than that for MAO A, of about 50-fold less than that for MAO A, of about 100-fold less than that for MAO A, of about 250-fold less than that for MAO A, of about 500-fold less than that for MAO A, of about 1000-fold less than that for MAO A, and of more than about 1000-fold less than that for MAO A. In a further aspect, a disclosed compound can bind LSD1 with a $K_D$ of about 5-fold less than that for MAO B, of about 10-fold less than that for MAO B, of about 20-fold less than that for MAO B, of about 30-fold less than that for MAO B, of about 50-fold less than that for MAO B, of about 100-fold less than that for MAO B, of about 250-fold less than that for MAO B, of about 500-fold less than that for MAO B, of about 1000-fold less than that for MAO B, and of more than about 1000-fold less than that for MAO B.

In various further aspects, the binding to LSD2 is selective. In a further aspect, the disclosed compounds exhibit a $K_D$ for LSD2 binding less than the $K_D$ for one or more of LSD1, MAO A, and MAO B. That is, a disclosed compound can have selectivity for the LSD2 protein vis-à-vis one or more of LSD1, MAO A, and MAO B proteins. For example, in one aspect, a disclosed compound can bind LSD2 with a $K_D$ of about 5-fold less than that for LSD1, of about 10-fold less than that for LSD1, of about 20-fold less than that for LSD1, of about 30-fold less than that for LSD1, or about 50-fold less than that for LSD1. In a further aspect, a disclosed compound can bind LSD2 with a $K_D$ of about 5-fold less than that for MAO A, of about 10-fold less than that for MAO A, of about 20-fold less than that for MAO A, of about 30-fold less than that for MAO A, of about 50-fold less than that for MAO A, of about 100-fold less than that for MAO A, of about 250-fold less than that for MAO A, of about 500-fold less than that for MAO A, of about 1000-fold less than that for MAO A, and of more than about 1000-fold less than that for MAO A. In a further aspect, a disclosed compound can bind LSD2 with a $K_D$ of about 5-fold less than that for MAO B, of about 10-fold less than that for MAO B, of about 20-fold less than that for MAO B, of about 30-fold less than that for MAO B, of about 50-fold less than that for MAO B, of about 100-fold less than that for MAO B, of about 250-fold less than that for MAO B, of about 500-fold less than that for MAO B, of about 1000-fold less than that for MAO B, and of more than about 1000-fold less than that for MAO B.

Alternatively, the inhibition of STAT protein activity can be determined in a cell-based assay. There are a variety of cell-based assays that are suitable for determination of inhibition of LSD protein activity known to one skilled in the art. For example, cell growth inhibition or cell arrest can be determined using a cell, either a permanent cell-line or a primary cell culture that has a LSD protein with dysfunction activity. In a further aspect, the LSD protein is LSD1. In a still further aspect, the LSD protein is LSD2. In a yet further aspect, the LSD protein dysfunction is one wherein the LSD protein is has acquired a gain of function mutation. Alternatively, the LSD protein dysfunction has a phenotype of persistent or constitutive activity. For example, the LSD protein can have a persistent or constitutive activity due to a dysfunction in an upstream regulatory protein. In a further aspect, the LSD protein is overexpressed due to a dysfunction in regulation of transcription and/or translation of the LSD gene. In a further aspect, the cell harbors an active oncogene is associated with LSD dysfunction.

In one aspect, the disclosed compounds and products of disclosed methods of making inhibit cell growth. In a still further aspect, the disclosed compounds and products of disclosed methods inhibit cell growth in an in vitro assay system. In an even further aspect, the in vitro assay system makes use of a cell-line derived from a from cancer or tumor selected from breast cancer, ovarian cancer, testicular cancer, lung cancer, liver cancer, prostate cancer, pancreatic cancer and a sarcoma. In a yet further aspect, the cell-line is derived from a human source. In a yet further aspect, the disclosed compounds inhibit cell growth in a cell with a persistently active LSD protein. In an even further aspect, the cell-line has an activated LSD protein. In a still further aspect, the cell-line is selected from AN3 CA, BT-20, BT-549, HCT 116, HER218, MCF7, MDA-MB-231, MDA-MB-235, MDA-MB-435S, MDA-MB-468, PANC-1, PC-3, SK-N-MC, T-47D, and U-87 MG. In one aspect, the disclosed compounds exhibit inhibition of cell growth activity in an in vitro cell-based assay with an $IC_{50}$ of less than about 500 µM, of less than about about 250 µM, less than about 100 µM, less than about 50 µM, less than about 10 µM, less than about 1 µM, less than about 500 nM, of less than about 100 nM, of less than about 10 nM, and of less than about 1 nM.

In one aspect, the disclosed compounds and products of disclosed methods of making inhibit cell migration. In a still further aspect, the disclosed compounds and products of disclosed methods inhibit cell migration in an in vitro assay system. In an even further aspect, the in vitro assay system makes use of a cell-line derived from a from cancer or tumor selected from breast cancer, ovarian cancer, testicular cancer, lung cancer, liver cancer, prostate cancer, pancreatic cancer and a sarcoma. In a yet further aspect, the cell-line is derived from a human source. In a yet further aspect, the disclosed compounds inhibit cell growth in a cell with a persistently active LSD protein. In an even further aspect, the cell-line has an activated LSD protein. In a still further aspect, the cell-line is selected from AN3 CA, BT-20, BT-549, HCT 116, HER218, MCF7, MDA-MB-231, MDA-MB-235, MDA-MB-435S, MDA-MB-468, PANC-1, PC-3, SK-N-MC, T-47D, and U-87 MG. In one aspect, the disclosed compounds exhibit inhibition of cell migration in an in vitro cell-based assay with an $IC_{50}$ of less than about 300 less than about 100 µM, less than about 50 µM, less than about 10 µM less than about 1 µM, less than about 500 nM, or of less than about 100 nM.

C. METHODS OF MAKING THE COMPOUNDS

In one aspect, the invention relates to methods of making compounds useful as inhibitors of LSD. In a further aspect, the products of disclosed methods of making are modulators of LSD activity. In a yet further aspect, the products of disclosed methods of making bind to a STAT protein and negatively modulate LSD activity. The compounds can, in one aspect, exhibit subtype selectivity. In a still further aspect, the products of disclosed methods of making exhibit selectivity for the LSD1 member of the LSD protein family. In an even further aspect, the products of the disclosed methods of making exhibit selectivity for the LSD2 member of the LSD protein family.

In one aspect, the invention relates to methods of making compounds useful as inhibitors of histone demethylase, which can be useful in the treatment of disorders of uncontrolled cellular proliferation. In a further aspect, the histone demethylase is LSD1. In a yet further aspect, the histone demethylase is LSD2.

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, in addition to other standard manipulations known in the literature or to one skilled in the art. The following examples are provided so that the invention might be more fully understood, are illustrative only, and should not be construed as limiting.

In one aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

1. Route I

In one aspect, substituted (E)-N'-(1-phenylethylidene)benzohydrazide analogs of the present invention can be prepared generically by the synthetic scheme as shown below.

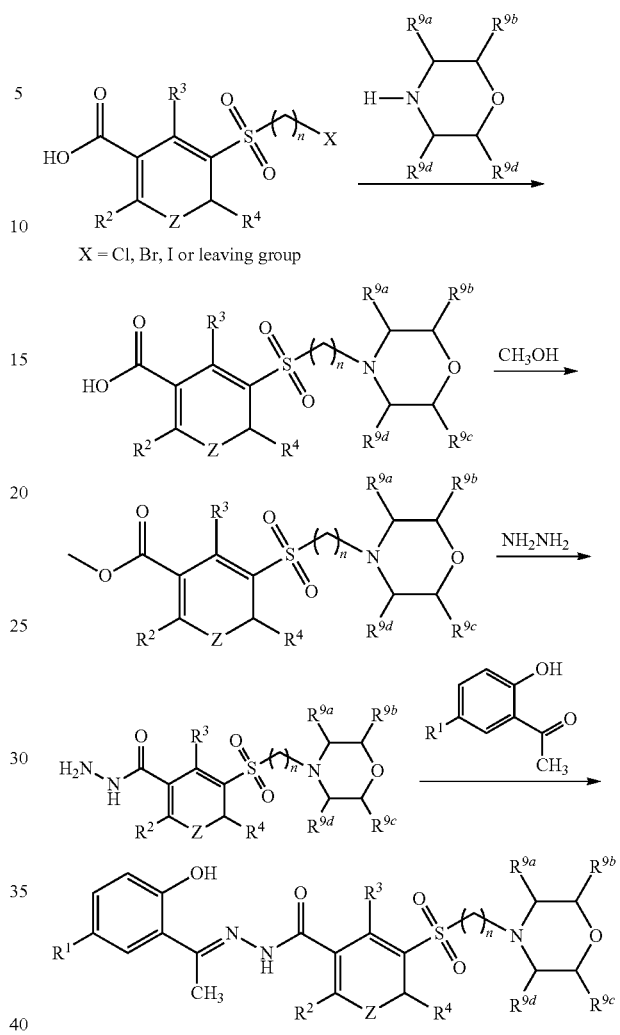

Compounds are represented in generic form, with substituents as noted in compound descriptions elsewhere herein. A more specific example is set forth below.

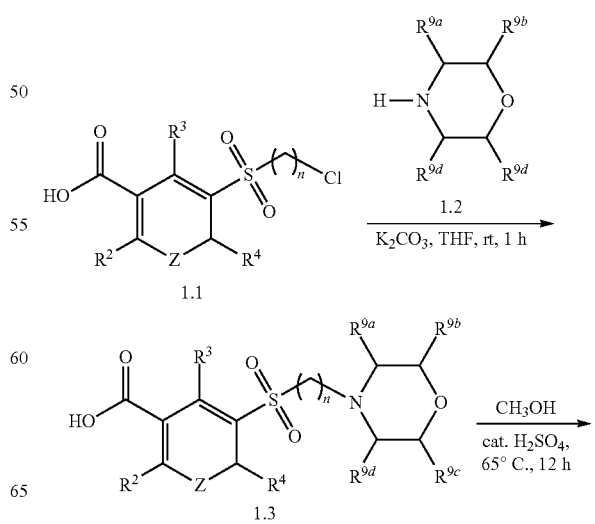

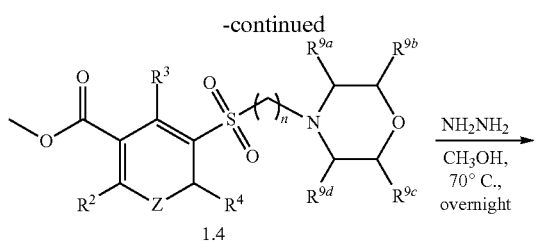

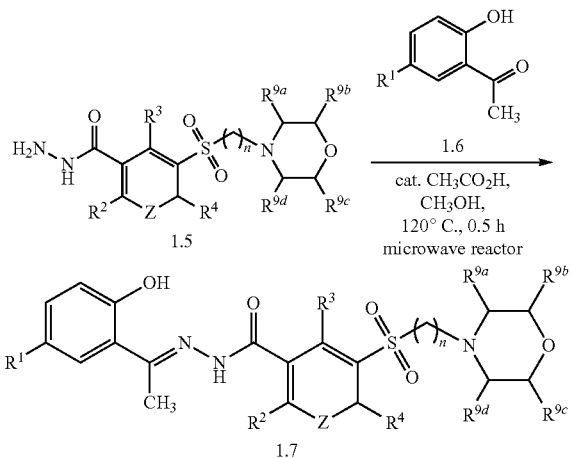

In one aspect, Route I begins with a suitable substituted acid derivative (1.1). Suitable substituted acid derivatives (1.1) are commercially available or can be readily prepared by one skilled in the art. In a typical reaction, compound of the type 1.1 is added to the amine derivative of type 1.2 in the presence of a suitable base, e.g., potassium carbonate, in suitable solvent such as THF. The reaction is stirred at room temperature (about 15-30° C.) for a time sufficient to complete the reaction, e.g., about twelve hours. After completion of the reaction, the solvent is removed under vacuum, and the compound of type 1.3 is isolated and purified by chromatography.

In one aspect, compounds of type 1.4 can be prepared by reaction of compounds of type 1.3 with an alcohol by an esterification reaction. In a typical reaction, a compound of type 1.3 is heated at a suitable temperature (e.g., at reflux, about 65° C.) in a suitable alcoholic solvent, e.g., methanol, in the presence of an acid catalyst such as concentrated sulfuric acid for a time sufficient to complete the reaction, e.g., overnight (about 8-18 h). After completion of the reaction, the solvent is removed under vacuum, and the compound of type 1.4, is isolated and purified by chromatography.

In one aspect, compounds of type 1.4 can provide compounds of type 1.5 by reaction with an appropriate hydrazine derivative (NH2NHR4). In a typical reaction, a compound of type 1.4 is added to a suitable hydrazine derivative (NH2NHR4) and heated at suitable temperature (e.g., at reflux, about 65° C.) in a suitable solvent, e.g., methanol, for a time sufficient to complete the reaction (e.g., about 12 h). After completion of the reaction, the solvent is removed under vacuum, and the compound of type 1.5, is isolated and purified by chromatography.

In one aspect, compounds of type 1.5 can provide compounds of type 1.7 by reaction with an appropriate carbonyl-containing compound (1.6). In a typical reaction, a compound of type 1.6 and a suitable hydrazine derivative (1.5) are dissolved in a suitable solvent, e.g., methanol, in the presence of a suitable acid catalyst (e.g., acetic acid), and the mixture is heated using a microwave reactor at suitable temperature, e.g., about 120° C., for a time sufficient to complete the reaction (e.g., about 30 min). After completion of the reaction and following cooling, the solvent is removed under vacuum, and the compounds of type 1.7, are isolated and purified by chromatography.

2. Route II

In one aspect, substituted (E)-N'-(1-phenylethylidene)benzohydrazide analogs of the present invention can be prepared generically by the synthetic scheme as shown below.

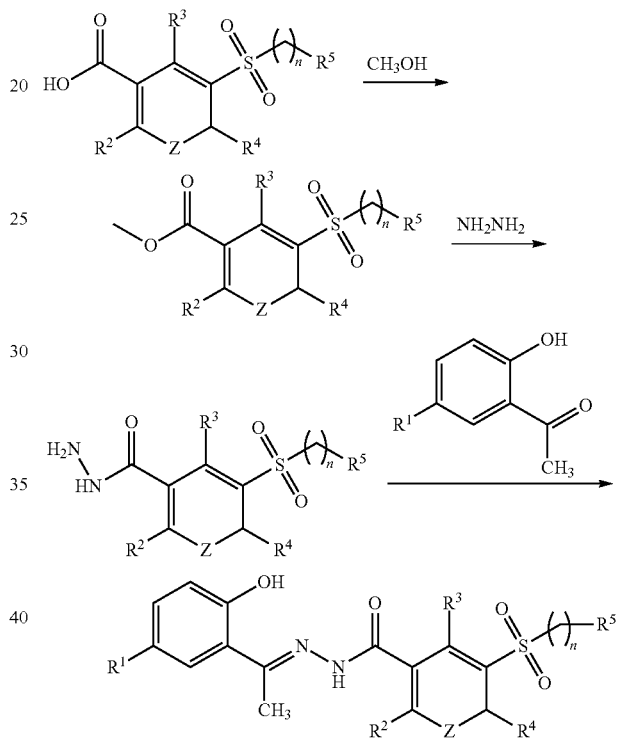

Compounds are represented in generic form, with substituents as noted in compound descriptions elsewhere herein. A more specific example is set forth below.

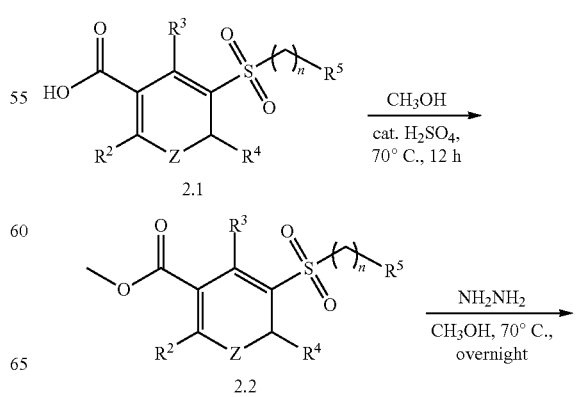

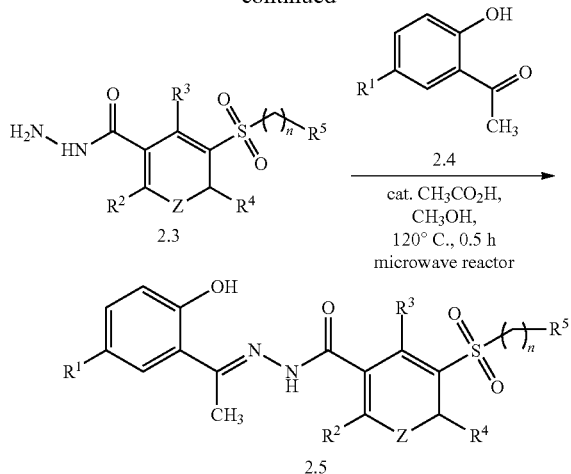

In one aspect, Route II begins with a suitable substituted acid derivative (2.1). Suitable substituted acid derivatives (2.1) are commercially available or can be readily prepared by one skilled in the art. In one aspect, compounds of type 2.2 can be prepared by reaction of compounds of type 2.1 with an alcohol by an esterification reaction. In a typical reaction, a compound of type 2.1 is heated at a suitable temperature (e.g., at reflux, about 70° C.) in a suitable alcoholic solvent, e.g., methanol, in the presence of an acid catalyst such as concentrated sulfuric acid for a time sufficient to complete the reaction, e.g., overnight (about 8-18 h). After completion of the reaction, the solvent is removed under vacuum, and the compound of type 2.2, is isolated and purified by chromatography.

In one aspect, compounds of type 2.2 can provide compounds of type 2.3 by reaction with an appropriate hydrazine derivative ($NH_2NHR^4$). In a typical reaction, a compound of type 2.2 is added to a suitable hydrazine derivative ($NH_2NHR^4$) and heated a suitable temperature (e.g., at reflux, about 70° C.) in a suitable solvent, e.g., methanol for time sufficient to complete the reaction such as overnight (8-18 h). After completion of the reaction, the solvent is removed under vacuum, and the compound of type 2.3, is isolated and purified by chromatography.

In one aspect, compounds of type 2.3 can be used to provide compounds of type 2.5 by reaction with an appropriate carbonyl-containing compound (2.4). In a typical reaction, a compound of type 2.4 and a suitable hydrazine derivative (2.3) are dissolved in a suitable solvent, e.g., methanol, in the presence of a suitable acid catalyst (e.g., acetic acid), and the mixture is heated using a microwave reactor at suitable temperature, e.g., about 120° C., at a time sufficient to complete the reaction (e.g., about 30 min). After completion of the reaction and following cooling, the solvent is removed under vacuum, and the compounds of type 2.5, are isolated and purified by chromatography.

In a further aspect, the compound produced exhibits inhibition of a histone demethylase. In a still further aspect, the histone demethylase is a member of the lysine-specific ("LSD") family of histone demethylases. In yet further aspect, the histone demethylase is LSD1. In an even further aspect, the histone demethylase is LSD2. In a still further aspect, the compound produced exhibits inhibition of cell viability.

In a further aspect, the compound produced exhibits inhibition with an $IC_{50}$ of less than about $1.0 \times 10^{-4}$ M. In a still further aspect, the compound produced exhibits inhibition with an $IC_{50}$ of less than about $1.0 \times 10^{-5}$ M. In a yet further aspect, the compound produced exhibits inhibition with an $IC_{50}$ of less than about $1.0 \times 10^{-6}$ M. In an even further aspect, the compound produced exhibits inhibition with an $IC_{50}$ of less than about $1.0 \times 10^{-7}$ M. In a still further aspect, the compound produced exhibits inhibition with an $IC_{50}$ of less than about $1.0 \times 10^{-8}$ M. In a yet further aspect, the compound produced exhibits inhibition with an $IC_{50}$ of less than about $1.0 \times 10^{-9}$ M.

It is contemplated that each disclosed methods can further comprise additional steps, manipulations, and/or components. It is also contemplated that any one or more step, manipulation, and/or component can be optionally omitted from the invention.

It is understood that a disclosed methods can be used to provide the disclosed compounds. It is also understood that the products of the disclosed methods can be employed in the disclosed methods of using.

D. PHARMACEUTICAL COMPOSITIONS

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In a further aspect, the invention relates to pharmaceutical compositions comprising a pharmaceutically acceptable carrier and an effective amount of the product of a disclosed synthetic method. In a further aspect, the effective amount is a therapeutically effective amount. In a further aspect, the effective amount is a prophylactically effective amount. In a further aspect, the compound is a disclosed compound.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require inhibition or negative modulation of LSD protein activity an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the from of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for inhibiting or negatively modulating LSD protein activity (e.g., treatment of a disorder of uncontrolled cellular proliferation, or one or more neurodegenerative disorders associated with LSD dysfunction) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

E. METHODS OF USING THE COMPOUNDS AND COMPOSITIONS

The disclosed compounds can be used as single agents or in combination with one or more other drugs in the treatment, prevention, control, amelioration or reduction of risk of the aforementioned diseases, disorders and conditions for which compounds of formula I or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

The pharmaceutical compositions and methods of the present invention can further comprise other therapeutically active compounds as noted herein which are usually applied in the treatment of the above mentioned pathological conditions.

1. Treatment Methods

The compounds disclosed herein are useful for treating, preventing, ameliorating, controlling or reducing the risk of a variety of disorders wherein the patient or subject would benefit from inhibition or negative modulation of a LSD protein. In one aspect, a treatment can include selective inhibition of LSD to an extent effective to affect histone demethylation activity. Thus, a disorder can be associated with histone demethylation activity, for example dysfunctional epigenetic regulation of genes in a cancer cell. In one aspect, provided is a method of treating or preventing a disorder in a subject comprising the step of administering to the subject at least one disclosed compound; at least one disclosed pharmaceutical composition; and/or at least one disclosed product in a dosage and amount effective to treat the disorder in the subject.

Also provided is a method for the treatment of one or more disorders, for which LSD inhibition is predicted to be beneficial, in a subject comprising the step of administering to the subject at least one disclosed compound; at least one disclosed pharmaceutical composition; and/or at least one disclosed product in a dosage and amount effective to treat the disorder in the subject.

In one aspect, provided is a method for treating a disorder of uncontrolled cellular proliferation, comprising: administering to a subject at least one disclosed compound; at least one disclosed pharmaceutical composition; and/or at least one disclosed product in a dosage and amount effective to treat the disorder in the subject. In a further aspect, provided is a method for treating or preventing a neurodegenerative disorder, comprising: administering to a subject at least one disclosed compound; at least one disclosed pharmaceutical composition; and/or at least one disclosed product in a dosage and amount effective to treat the disorder in the subject. Also provided is a method for the treatment of a disorder in a mammal comprising the step of administering to the mammal at least one disclosed compound, composition, or medicament.

The invention is directed at the use of described chemical compositions to treat diseases or disorders in patients (preferably human) wherein LSD inhibition would be predicted to have a therapeutic effect, such as disorders of uncontrolled cellular proliferation (e.g. cancers) and neurodegenerative disorders such as Alzheimer's disease, Huntington's disease, and Parkinson's disease, by administering one or more disclosed compounds or products.

The compounds disclosed herein are useful for treating, preventing, ameliorating, controlling or reducing the risk of a variety of disorders of uncontrolled cellular proliferation. In one aspect, the disorder of uncontrolled cellular proliferation is associated with a histone demethylase dysfunction. In a further aspect, the histone demethylase dysfunction is disregulation of the LSD. In a still further aspect, the histone demethylase dysfunction is disregulation of the LSD1. In an even further aspect, the histone demethylase dysfunction is disregulation of the LSD2.

Also provided is a method of use of a disclosed compound, composition, or medicament. In one aspect, the method of use is directed to the treatment of a disorder. In a further aspect, the disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

Examples of disorders associated with a histone demethylase dysfunction include a disorder of uncontrolled cellular proliferation. In a yet further aspect, the disorder of uncontrolled cellular proliferation is cancer. In a yet further aspect, the cancer is a leukemia. In an even further aspect, the cancer is a sarcoma. In a still further aspect, the cancer is a solid tumor. In a yet further aspect, the cancer is a lymphoma.

It is understood that cancer refer to or describe the physiological condition in mammals that is typically characterized by unregulated cell growth. The cancer may be multi-drug resistant (MDR) or drug-sensitive. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer.

In various aspects, further examples of cancers are basal cell carcinoma, biliary tract cancer; bone cancer; brain and CNS cancer; choriocarcinoma; connective tissue cancer; esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas In a further aspect, the cancer is a hematological cancer. In a still further aspect, the hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), Hodgkin lymphoma, Non-Hodgkin lymphoma, multiple myeloma, solitary myeloma, localized myeloma, and extramedullary myeloma. In a still further aspect, the cancer is selected from chronic lymphocytic leukemia, small lymphocytic lymphoma, B-cell non-Hodgkin lymphoma, and large B-cell lymphoma.

In a further aspect, the cancer is a cancer of the brain. In a still further aspect, the cancer of the brain is selected from a glioma, medulloblastoma, primitive neuroectodermal tumor (PNET), acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor. In a yet further aspect, the glioma is selected from ependymoma, astrocytoma, oligodendroglioma, and oligoastrocytoma. In an even further aspect, the glioma is selected from juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, multifocal gliomatous tumor, multicentric glioblastoma multiforme tumor, paraganglioma, and ganglioglioma.

In one aspect, the cancer can be a cancer selected from cancers of the blood, brain, genitourinary tract, gastrointestinal tract, colon, rectum, breast, kidney, lymphatic system, stomach, lung, pancreas, and skin. In a further aspect, the cancer is selected from prostate cancer, glioblastoma multiforme, endometrial cancer, breast cancer, and colon cancer. In a further aspect, the cancer is selected from a cancer of the breast, ovary, prostate, head, neck, and kidney. In a still further aspect, the cancer is selected from cancers of the blood, brain, genitourinary tract, gastrointestinal tract, colon, rectum, breast, livery, kidney, lymphatic system, stomach, lung, pancreas, and skin. In a yet further aspect, the cancer is selected from a cancer of the lung and liver. In an even further aspect, the cancer is selected from a cancer of the breast, ovary, testes and prostate In a still further aspect, the cancer is a cancer of the breast. In a yet further aspect, the cancer is a cancer of the ovary. In an even further aspect, the cancer is a cancer of the prostate. In a still further aspect, the cancer is a cancer of the testes.

In various aspects, disorders associated with a histone demethylase dysfunction include neurodegenerative disorders. In a further aspect, the neurodegenerative disease is selected from Alzheimer's disease, Parkinson's disease, and Huntington's disease.

The compounds are further useful in a method for the prevention, treatment, control, amelioration, or reducation of risk of the diseases, disorders and conditions noted herein. The compounds are further useful in a method for the prevention, treatment, control, amelioration, or reduction of risk of the aforementioned diseases, disorders and conditions in combination with other agents.

The present invention is further directed to administration of a LSD inhibitor for improving treatment outcomes in the context of disorders of uncontrolled cellular proliferation, including cancer. That is, in one aspect, the invention relates to a cotherapeutic method comprising the step of administering to a mammal an effective amount and dosage of at least one compound of the invention in connection with cancer therapy.

In a further aspect, administration improves treatment outcomes in the context of cancer therapy. Administration in connection with cancer therapy can be continuous or intermittent. Administration need not be simultaneous with therapy and can be before, during, and/or after therapy. For example, cancer therapy can be provided within 1, 2, 3, 4, 5, 6, 7 days before or after administration of the compound. As a further example, cancer therapy can be provided within 1, 2, 3, or 4 weeks before or after administration of the compound. As a still further example, cognitive or behavioral therapy can be provided before or after administration within a period of time of 1, 2, 3, 4, 5, 6, 7, 8, 9, or 10 half-lives of the administered compound.

In one aspect, the disclosed compounds can be used in combination with one or more other drugs in the treatment, prevention, control, amelioration, or reduction of risk of diseases or conditions for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly.

Accordingly, the pharmaceutical compositions include those that contain one or more other active ingredients, in addition to a compound of the present invention.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present invention. When a compound of the present invention is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present invention.

The weight ratio of a disclosed compound to the second active ingredient can be varied and will depend upon the effective dose of each ingredient. Generally, an effective dose of each will be used. Thus, for example, when a compound of the present invention is combined with another agent, the weight ratio of a disclosed compound to the other agent will generally range from about 1000:1 to about 1;1000, preferably about 200:1 to about 1:200. Combinations of a compound of the present invention and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be coadministered, either in concomitant therapy or in a fixed combination.

In one aspect, the compound can be employed in combination with anti-cancer therapeutic agents or other known therapeutic agents.

In the treatment of conditions which require inhibition or negative modulation of LSD, an appropriate dosage level will generally be about 0.01 to 1000 mg per kg patient body weight per day which can be administered in single or multiple doses. Preferably, the dosage level will be about 0.1 to about 250 mg/kg per day; more preferably about 0.5 to about 100 mg/kg per day. A suitable dosage level can be about 0.01 to 250 mg/kg per day, about 0.05 to 100 mg/kg per day, or about 01 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in one aspect, the invention relates to methods for inhibiting or negatively modulating LSD in at least one cell, comprising the step of contacting the at least one cell with at least one compound of the invention, in an amount effective to modulate or activate LSD activity response, e.g. LSD1 or LSD2, in the at least one cell. In a further aspect, the cell is mammalian, for example human. In a further aspect, the cell has been isolated from a subject prior to the contacting step. In a further aspect, contacting is via administration to a subject.

a. Treatment of a Disorder of Uncontrolled Cellular Proliferation

In one aspect, the invention relates to a method for the treatment of a disorder of uncontrolled cellular proliferation in a mammal, the method comprising the step of administering to the mammal an effective amount of least one disclosed compound or a product of a disclosed method of making a compound, or a pharmaceutically acceptable salt, hydrate, solvate, or polymorph thereof, thereby treating the disorder of uncontrolled cellular proliferation.

In a still further aspect, the effective amount is a therapeutically effective amount. In a yet still further aspect, the effective amount is a prophylactically effective amount.

In a further aspect, the mammal is a human. In a yet further aspect, the method further comprises the step of identifying a mammal in need of treatment of a disorder of uncontrolled cellular proliferation. In a still further aspect, the mammal has been diagnosed with a need for treatment of a disorder of uncontrolled cellular proliferation prior to the administering step.

In a further aspect, the disorder of uncontrolled cellular proliferation is associated with a histone demethylase dysfunction. In a further aspect, the histone demethylase is a lysine-specific histone demethylase. In a yet further aspect, the lysine-specific histone demethylase is LSD1. In an even further aspect, the lysine-specific histone demethylase is LSD2.

In a further aspect, the disorder of uncontrolled cellular proliferation is a cancer. In a yet further aspect, the cancer is a leukemia. In an even further aspect, the cancer is a sarcoma. In a still further aspect, the cancer is a solid tumor. In a yet further aspect, the cancer is a lymphoma. In an even further aspect, the cancer is selected from chronic lymphocytic leukemia, small lymphocytic lymphoma, B-cell non-Hodgkin lymphoma, and large B-cell lymphoma. In a still further aspect, the cancer is selected from cancers of the blood, brain, genitourinary tract, gastrointestinal tract, colon, rectum, breast, livery, kidney, lymphatic system, stomach, lung, pancreas, and skin. In a yet further aspect, the cancer is selected from a cancer of the lung and liver. In an even further aspect, the cancer is selected from a cancer of the breast, ovary, testes and prostate. In a still further aspect, the cancer is a cancer of the breast. In a yet further aspect, the cancer is a cancer of the ovary. In an even further aspect, the cancer is a cancer of the prostate. In a still further aspect, the cancer is a cancer of the testes.

b. Decreasing Histone Demethylase Activity

In one aspect, the invention relates to a method for decreasing histone demethylase activity in a mammal, the method comprising the step of administering to the mammal an effective amount of at least one disclosed compound or a product of a disclosed method of making a compound, or a pharmaceutically acceptable salt, hydrate, solvate, or polymorph thereof, or a pharmaceutically acceptable salt, hydrate, solvate, or polymorph thereof, thereby decreasing histone demethylase activity in the mammal.

In a still further aspect, the effective amount is a therapeutically effective amount. In a yet still further aspect, the effective amount is a prophylactically effective amount.

In a further aspect, the mammal is a human. In a yet further aspect, the method further comprises the step of identifying a mammal in need of decreasing histone demethylase activity. In a still further aspect, the mammal has been diagnosed with a need for decreasing histone demethylase activity prior to the administering step.

In a further aspect, the histone demethylase is a lysine-specific histone demethylase. In a yet further aspect, the lysine-specific histone demethylase is LSD1. In an even further aspect, the lysine-specific histone demethylase is LSD2.

In a further aspect, the need for decreasing histone demethylase activity is associated with a histone demethylase dysfunction. In a yet further aspect, the histone demethylase dysfunction is associated with a disorder of uncontrolled cellular proliferation. In a yet further aspect, the method further comprises the step of identifying a mammal in need of treating a disorder of uncontrolled cellular proliferation. In a still further aspect, the mammal has been diagnosed with a need for treating a disorder of uncontrolled cellular proliferation prior to the administering step.

In a still further aspect, the disorder of uncontrolled cellular proliferation is a cancer. In a yet further aspect, the cancer is a leukemia. In an even further aspect, the cancer is a sarcoma. In a still further aspect, the cancer is a solid tumor. In a yet further aspect, the cancer is a lymphoma. In an even further aspect, the cancer is selected from chronic lymphocytic leukemia, small lymphocytic lymphoma, B-cell non-Hodgkin lymphoma, and large B-cell lymphoma. In a still further aspect, the cancer is selected from cancers of the blood, brain, genitourinary tract, gastrointestinal tract, colon, rectum, breast, livery, kidney, lymphatic system, stomach, lung, pancreas, and skin. In a yet further aspect, the cancer is selected from a cancer of the lung and liver. In an even further aspect, the cancer is selected from a cancer of the breast, ovary, testes and prostate. In a still further aspect, the cancer is a cancer of the breast. In a yet further aspect, the cancer is a cancer of the ovary. In an even further aspect, the cancer is a cancer of the prostate. In a still further aspect, the cancer is a cancer of the testes.

c. Decreasing Histone Demethylase Activity in Cells

In one aspect, the invention relates to a method for decreasing histone demethylase activity in at least one cell, the method comprising the step of contacting the at least one cell with an effective amount of least one disclosed compound or a product of a disclosed method of making a compound, or a pharmaceutically acceptable salt, hydrate, solvate, or polymorph thereof, or a pharmaceutically acceptable salt, hydrate, solvate, or polymorph thereof, thereby decreasing histone demethylase activity in the cell.

In a still further aspect, the effective amount is a therapeutically effective amount. In a yet still further aspect, the effective amount is a prophylactically effective amount.

In a further aspect, the cell is mammalian. In a still further aspect, the cell is human. In a yet further aspect, contacting is via administration to a mammal. In a further aspect, the method further comprises the step of identifying the mammal as having a need of decreasing histone demethylase activity in a cell. In a still further aspect, the mammal has been diagnosed with a need for decreasing histone demethylase activity prior to the administering step.

In a further aspect, the histone demethylase is a lysine-specific histone demethylase. In a yet further aspect, the lysine-specific histone demethylase is LSD1. In an even further aspect, the lysine-specific histone demethylase is LSD2.

In a further aspect, the need for decreasing histone demethylase activity in a cell is associated with a disorder of uncontrolled cellular. In a still further aspect, the disorder of uncontrolled cellular proliferation is a cancer. In a yet further aspect, the cancer is a leukemia. In an even further aspect, the cancer is a sarcoma. In a still further aspect, the cancer is a solid tumor. In a yet further aspect, the cancer is a lymphoma. In an even further aspect, the cancer is selected from chronic lymphocytic leukemia, small lymphocytic lymphoma, B-cell non-Hodgkin lymphoma, and large B-cell lymphoma. In a still further aspect, the cancer is selected from cancers of the blood, brain, genitourinary tract, gastrointestinal tract, colon, rectum, breast, livery, kidney, lymphatic system, stomach, lung, pancreas, and skin. In a yet further aspect, the cancer is selected from a cancer of the lung and liver. In an even further aspect, the cancer is selected from a cancer of the breast, ovary, testes and prostate. In a still further aspect, the cancer is a cancer of the breast. In a yet further aspect, the cancer is a cancer of the ovary. In an even further aspect, the cancer is a cancer of the prostate. In a still further aspect, the cancer is a cancer of the testes.

2. Manufacture of a Medicament

In one aspect, the invention relates to a method for the manufacture of a medicament for inhibition of histone demethylase activity in a mammal comprising combining a therapeutically effective amount of a disclosed compound or product of a disclosed method with a pharmaceutically acceptable carrier or diluent.

F. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein.

The following exemplary compounds of the invention were synthesized. The Examples are provided herein to illustrate the invention, and should not be construed as limiting the invention in any way. The Examples are typically depicted in free base form, according to the IUPAC naming convention. However, some of the Examples were obtained or isolated in salt form.

As indicated, some of the Examples were obtained as racemic mixtures of one or more enantiomers or diastereomers. The compounds may be separated by one skilled in the art to isolate individual enantiomers. Separation can be carried out by the coupling of a racemic mixture of compounds to an enantiomerically pure compound to form a diastereomeric mixture, followed by separation of the individual diastereomers by standard methods, such as fractional crystallization or chromatography. A racemic or diastereomeric mixture of the compounds can also be separated directly by chromatographic methods using chiral stationary phases.

1. General Chemical Materials and Methods

All analytical or anhydrous grade reagents were purchased from commercial sources and were used without further purification. Solvents were of analytical or anhydrous grade (Sigma-Aldrich). Specialty chemicals and building blocks obtained from several suppliers were of the highest offered purity (always ≥95%).

NMR spectroscopy was performed on a Varian Unity 400 instrument with a 5 mm broadband probe and using standard pulse sequences. Chemical shifts (δ) are reported in parts-per-million (ppm) downfield from solvent references. Coupling constants (J-values) are expressed in Hz.

Mass spectrometry was performed on a Finnigan LCQ Duo LCMS ion trap electrospray (ESI) mass spectrometer. All samples were analyzed by positive ESI-MS and the mass-to-charge ratio (m/z) of the protonated molecular ion is reported.

Microwave-assisted reactions were performed on a Biotage Initiator 2.5 at various powers.

Hydrogenation reactions were performed on a standard Parr hydrogenation apparatus.

Reactions were monitored either by HPLC or TLC. When monitored by TLC, reactions were analyzed on Baker flexible-backed plates coated with 200 μm of silica gel containing a fluorescent indicator. Preparative TLC was performed on 20 cm×20 cm. Analtech Uniplates coated with a 1000 or 2000 μm silica gel layer containing a fluorescent (UV 254) indicator. Elution mixtures are reported as v:v. Spot visualization was achieved using UV light.

Flash chromatography was performed on a Teledyne Isco CombiFlash RF 200 using appropriately sized Redisep Rf Gold or Standard normal-phase silica or reversed-phase C-18 columns. Crude compounds were adsorbed on silica gel, 70-230 mesh 40 Å (for normal phase) or Celite 503 (for reversed-phase) and loaded into solid cartridges. Elution mixtures are reported as v:v.

2. Molecular Modeling and Virtual Screening Methods

All computational studies employed PDB ID 2Z5U for the structural coordinates of LSD1. Virtual docking methods ICM, Glide and GOLD programs were implemented. The protein structure was prepared by 3D protonation, deletion of water molecules and energy minimization using the ICM force field and distance-dependent dielectric potential with an RMS gradient of 0.1; heavy atoms in the protein were kept fixed, and histidine residues were considered as neutral. Virtual screening calculations utilized default parameters (unless explicitly specified otherwise) with ICM and Glide scores as scoring functions respectively. In both cases, FAD was defined as the ligand and an active site region was defined by a sphere of radius 12 Å around the bound FAD in complex with LSD1.

Confirmation of the accuracy and efficiency of the applied docking protocol used the FAD cofactor adenine dinucleotide fragment, and the flavin fragment, and known LSD1 inhibitors (decoy set) as positive controls. Two separate docking runs were carried out with ICM and the Glide docking program; GOLD docking was employed for re-scoring.

The compound database was prepared using Ligprep 2.1.23 (Schrödinger, LLC., New York, N.Y.). Two rounds of VS, including HTVS and standard precision (SP) docking, were adopted. The top 10000 compounds ranked by Glide were stored and submitted for additional docking experiments using ICM docking. The final set of 2000 hits was selected based on ICM scores and individual compounds were visually inspected to check the docking poses and interactions between ligands and LSD1. GOLD consensus scoring functions were employed further to re-score these 2000 hits selected from Glide and ICM. Finally, 121 compounds were purchased (if available) or synthesized for LSD1 inhibition studies.

3. MD Simulation Methods

All simulations were performed using the AMBER ff99SB force field (Hornak, V., et al. *Proteins* 2006, 65 (3), 712-25) for LSD1, the general Amber force field ('gaff'; see Wang, J., et al. *J Comput Chem* 2004, 25 (9), 1157-74) for compound 12, and the TIP3P (Jorgensen, W. L., *Journal of Chemical Physics* 1982, (77), 4156-4163) model for water was employed. The simulations approximated long-range electrostatic interactions using the particle-mesh Ewald method (PME) procedure (Essmann, U., et al. *Journal of Chemical Physics* 1995, (103), 8577-8593; Darden, T., et al. *Journal of Chemical Physics* 1993, (98), 10089-10092). Using LEaP the binding modes generated from ICM docking in complex with LSD1 were solvated to neutral charge and the complexes were first minimized with PMEMD (Case, D. A, et al. *AMBER*11, San Francisco, 2010). Following minimization, 200 ps of unrestrained molecular dynamics simulation using a non-bonded interaction cutoff of 9 Å was run for both binding modes with a constant pressure periodic boundary maintaining 1 atm of pressure and isotropic position scaling with a relaxation time of 2 ps. SHAKE was used to constrain bonds involving hydrogen and Langevin dynamics were used to regulate temperature (Case, D. A., et al. *AMBER*11, San Francisco, 2010), maintaining 300 K. Relative free energies of binding for comparisons between the two binding modes were predicted using MMPBSA.py[9] with 100 snapshots at 1-ps intervals starting either at 1 ps or 101 ps into the trajectory.

4. Virtual Screening Results

The first crystal structures of LSD1 elucidating critical architectural features were later by Stavropoulos et al. (*Nat Struct Mol Biol* 2006, 13(7):626-32; Protein Data Bank or PDB ID 2H94; see http://www.wwpdb.org/), Yang et al. (*Mol Cell* 2006, 23 (3), 377-87; PDB ID 2IW5), and Chen et al. (*Proc Natl Acad Sci USA* 2006, 103 (38), 13956-61; PDB ID 2HKO). These 2.9 Å, 2.57 Å, and 2.8 Å structures, respectively, show a highly negatively charged substrate-binding cavity spacious enough to accommodate the N-terminal tail of histone H3. Further, an N-terminal SWIRM domain and an insertion in the core catalytic domain, termed the Tower Domain, were established as necessary structural motifs for enzymatic activity and interactions with cofactors such as CoREST. For the studies described herein, the structure, PDB ID 2Z5U, was used with bound LSD1 inhibitor tranylcypromine for computational studies, including virtual screening, docking, and molecular dynamics (Mimasu, S., et al. *Biochem Biophys Res Commun* 2008, 366 (1), 15-22). In order to evaluate the chemical space outside of tranylcypromine and polyamine derivatives, HTVS was used with an in-house library. The library was curated from publicly available vendor libraries, totaling approximately 13 million compounds, using custom filters developed in-house. Compounds were filtered based on Lipinski's rule of five, with exceptions occurring in only 62,000 compounds. Further, structurally redundant compounds were removed such that the resulting library contained a diverse, yet manageable set of about 2 million compounds. Prior to screening, compounds were prepared using the LigPrep module of the Schrodinger Suite as well as ICM's inbuilt preparation of three-dimensional (3D) ligands such that physiologically relevant protonation states were used.

Prepared ligands were then docked against three different sites on LSD1; the FAD site located in the amine oxidase domain, and the adenine dinucleotide and flavin fragments of this pocket. The docking protocols used by both ICM and Glide were run with the FAD, adenine dinucleotide, flavin fragments, and known LSD1 inhibitors to check for accuracy. In addition to the docking algorithm rankings, visual inspection of the docking results was used to evaluate binding position, suitable pose, and orientation. Taken together, the scoring functions from ICM and Glide were able to correctly identify known inhibitors within the top 2% of the decoy set used. GOLD was used to re-score and the GOLD fitness function produced similar enrichments.

A virtual screen was set up against the FAD-binding pocket of LSD1 using the established docking protocol and the 2 million-compound database. The top 10,000 compounds were selected from both ICM and Glide scoring functions for further analysis. A few identical compounds were scored similarly between the two algorithms; this redundancy was filtered out. Furthermore, visual inspection was performed to filter out similar compounds and to increase the diversity of the final selection. Visual analysis also allowed identification of key interactions within the FAD-binding pocked of LSD1. These include hydrogen bonding with Ser289, Arg310 and Arg316, van der Waals interactions with Val590 and Leu625, and π interactions with Trp756. Moreover, compounds with hydroxyl and hydrophobic electron withdrawing groups seemed to show increased enrichment in the initial docking results. The FAD-binding pocket of LSD1 is a deep and narrow crevice in the interior of the protein and is surrounded by hydrophobic amino acid residues. Thus the hydrophobic character of the compounds may play an important role in the random walk of the compound into the active site.

Based on the selection criteria discussed above, 121 structurally distinct compounds were procured and submitted for biochemical screening against LSD1. The biochemical assay, as described in the experimental section, measures $H_2O_2$ produced from the oxidative demethylation of a peptide substrate. From the 121 compounds, a series of related compounds, which showed potent activity in the biochemical assay, were identified. Docking scores, ranks, and accompanying biochemical assay results for the series are presented in Tables 1, 2, and 6-9.

Of the ten active compounds in Table 1 (and associated tables providing biochemical and cellular data, Tables 6, 8, and 9), that were discovered using virtual screening methods, e.g. compounds 1, 2, 4 and 5 showed similar binding modes within the FAD-binding site of LSD1. Additionally, the docking scores for compounds 1, 2, 4 and 5 correlated well with the observed biochemical activity. These results suggested that improved inhibitors targeted toward the adenine dinucleotide pocket in the amine oxidase domain of LSD1 were accessible.

The Glide scores are predictive and correlated well with compounds having p-OH or m-Cl aryl substitutions (compounds 1 and 5). It is clear from these studies that the hydrophobic electron withdrawing groups such as —Cl are tolerated, whereas small alkyl substituents such as methyl (e.g. compound 8) or fused bicyclic containing compound 10 have lower activity. Introduction of any donating groups particularly the —$OCH_3$ functional group at the $2^{nd}$ position lost activity due to lack of Gly314 H-bonding interactions (e.g. compound 6). The lack of biochemical activity of compound 6 was highly predictive from docking scores, where ICM and Glide provided −18.39 and −6.63 kcal/mol energies respectively. In subsequent docking analysis, additional benzohydrazine series of compounds were identified, with hydrazine —C methyl or aryl 4-substituted sulfone containing compounds, as exemplified by the virtual hit compound 9, which exhibited potent LSD1 inhibition activity with an $IC_{50}$ of 19 nM. The low docking score of compound 9 is primarily due to the shift in 2-OH aryl ring position. Compound 9, with a sulfone/morpholine substituent, was chosen as a backbone for further optimization due, in part, to its chemical stability.

The binding mode of compound 12 with the sulfone/morpholine is depicted with the docking pose predicted from ICM in FIG. 1. In this model, the phenolic group fits well in the pocket composed of residues Ser289, Gly314 and Arg316. The central carbonyl group appears to be involved in strong H-bonding interactions with Arg310 amino group and the morpholine oxygen shows H-bonding interactions with Val590. These sets of hydrogen bonding interactions were also observed with Glide and GOLD docking experiments. The additional experiments showed the morpholine substituted aryl ring participating in Tr-Tr interactions with Trp756 residue while the morpholine oxygen retained in H-bonding with Val590.

Chemical optimization also focused on the design of compounds containing heteroaryl rings on either side of compound 12. Computational models using these results generated a variety of chemically plausible scaffolds, from which a substituted pyridine was identified as being an appropriate moiety capable of interacting with Ser289, Gly314 and Arg316, surrounding residues and ideal properties. A representative is compound 24, which had potent LSD1 activity of (28 nM) and also exhibited a similar binding mode to that of compound 12 (see FIG. 2).

Many of the representative compounds contain a C-alkyl hydrazine to increase metabolic stability of the series. However, a bulkier group, like the ethyl group of compound 21, isn't well accommodated by the binding pocket as illustrated in different biochemical activities of compounds 12 and 21. Aryl substitution with methylsulfone (compound 25) and substituted with a morpholine ring (compound 12) increased biochemical efficacy by roughly an order of magnitude when compared to compound 11. Addition of only a morpholine ring maintains some biochemical activity as illustrated by compound 23. Replacing the sulfono-morpholine with sulfono-N-dimethyl also maintained biochemical activity as illustrated by compound 18. Additionally, replacement of the 2-OH group with a chloro was found not to be well accommodated and a significant drop in activity was demonstrated between compounds 12 and 16. Results with compound 24 suggest that using a substituted pyridine is accommodated by the enzyme, but various other substitutions and heterocycles generally resulted in a drop in biochemical activity as illustrated in compounds 13, 14, 15, 17, 19, 20 and 22.

Many of the representative compounds in Table 2 contained a C-alkyl hydrazine to increase metabolic stability of the series. However, a bulkier group, e.g. the ethyl group of compound 21, is less well accommodated by the binding pocket as illustrated in the different biochemical activities of compounds 12 and 21. The aryl substitution with methylsulfone (e.g. compound 25) and substituted with a morpholine ring (compound 12) increased biochemical efficacy by roughly an order of magnitude when compared to compound 11. Addition of a heterocycle, e.g. a morpholine ring, maintains biochemical activity as illustrated by compound 23. Replacing the sulfono-morpholine with sulfono-N-dimethyl also maintained biochemical activity as illustrated by compound 18. Additionally, replacement of the 2-OH group with a chloro was found not to be accommodated with a significant drop in activity between compounds 12 and 16. As discussed above, compound 24 suggests that using a substituted pyridine is accommodated by the enzyme. Further analysis suggests that the hydroxyl of compound 12 is associated with increased biochemical activity, e.g. when this substituent group is substituted with a chlorine (compound 16), activity was decreased.

TABLE 1

| No. | Structure | ICM Score | Glide Score | Gold Fitness |
| --- | --- | --- | --- | --- |
| 1 | 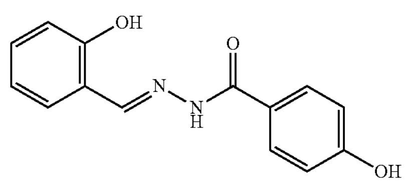 [SMILES: O=C(N/N=C/c1ccccc1O)c1ccc(O)cc1] | −42.25 | −8.14 | 56.26 |
| 2 | 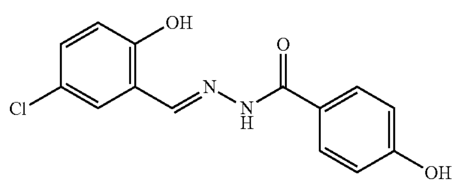 [SMILES: O=C(N/N=C/c1cc(Cl)ccc1O)c1ccc(O)cc1] | −42.25 | −7.92 | 58.21 |
| 3 | 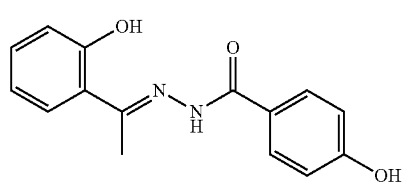 [SMILES: C/C(=N\NC(=O)c1ccc(O)cc1)c1ccccc1O] | −21.91 | −7.87 | 51.29 |
| 4 | 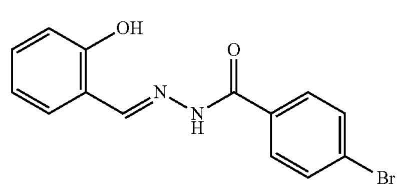 [SMILES: O=C(N/N=C/c1ccccc1O)c1ccc(Br)cc1] | −37.77 | −8.64 | 57.69 |

TABLE 1-continued
| No. | Structure | ICM Score | Glide Score | Gold Fitness |
|---|---|---|---|---|
| 5 | 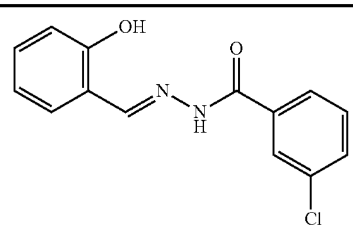 | −36.3 | −8.84 | 47.98 |
| 6 | 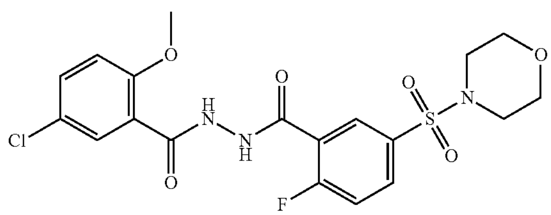 [SMILES: COc1ccc(Cl)cc1C(=O)NNC(=O)c1cc(S(=O)(=O)N2CCOCC2)ccc1F] | −18.39 | −6.63 | 49.93 |
| 7 | 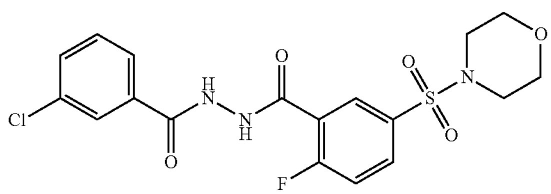 [SMILES: O=C(NNC(=O)c1cc(S(=O)(=O)N2CCOCC2)ccc1F)c1cccc(Cl)c1] | −8.16 | −7.21 | 41.86 |
| 8 | 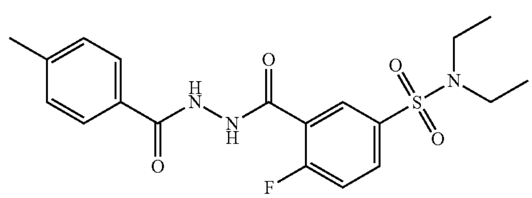 [SMILES: CCN(CC)S(=O)(=O)c1ccc(F)c(C(=O)NNC(=O)c2ccc(C)cc2)c1] | −8.5 | −6.81 | 52.19 |
| 9 | 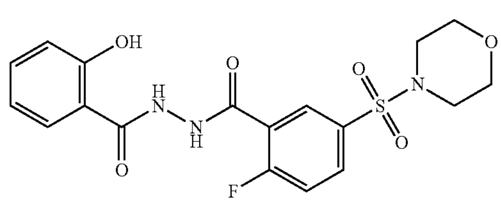 [SMILES: O=C(NNC(=O)c1cc(S(=O)(=O)N2CCOCC2)ccc1F)c1ccccc1O] | −24 | −6.26 | 43.26 |
| 10 | 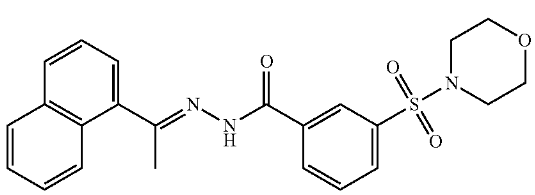 [SMILES: C/C(=N\NC(=O)c1cccc(S(=O)(=O)N2CCOCC2)c1)c1cccc2ccccc12] | −20.97 | −6.14 | 46.64 |
TABLE 2
| No. | Structure | ICM Score | Glide Score | Gold Fitness |
|---|---|---|---|---|
| 11 | 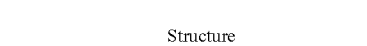 | −29.76 | −7.89 | 58.21 |

TABLE 2-continued

| No. | Structure | ICM Score | Glide Score | Gold Fitness |
|---|---|---|---|---|
| 12 | 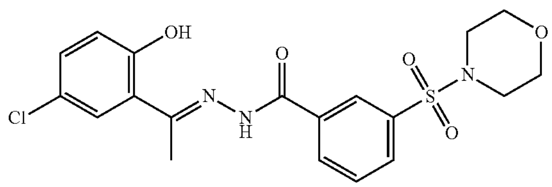 | −38.16 | −8.96 | 58.17 |
| 13 | 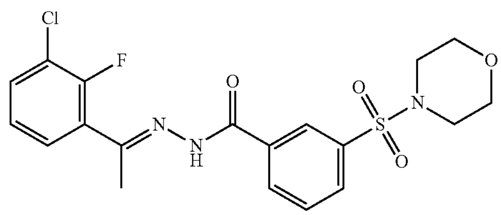 [SMILES: C/C(=N\NC(=O)c1cccc(S(=O)(=O)N2CCOCC2)c1)c1cccc(Cl)c1F] | −36.14 | −9.21 | 54.88 |
| 14 | 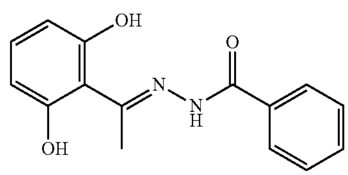 [SMILES: C/C(=N\NC(=O)c1ccccc1)c1c(O)cccc1O] | −23.81 | −6.75 | 46.21 |
| 15 | 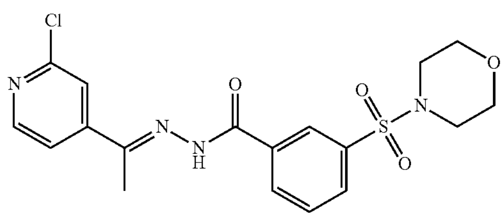 [SMILES: C/C(=N\NC(=O)c1cccc(S(=O)(=O)N2CCOCC2)c1)c1ccnc(Cl)c1] | −31.24 | −7.91 | 51.29 |
| 16 | 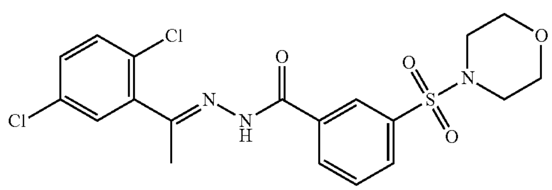 [SMILES: C/C(=N\NC(=O)c1cccc(S(=O)(=O)N2CCOCC2)c1)c1cc(Cl)ccc1Cl] | −41.26 | −6.87 | 53.29 |
| 17 | 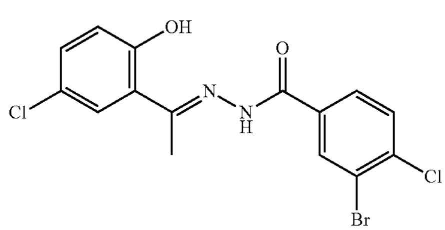 [SMILES: C/C(=N\NC(=O)c1ccc(Cl)c(Br)c1)c1cc(Cl)ccc1O] | −29.23 | −7.93 | 43.29 |
| 18 | 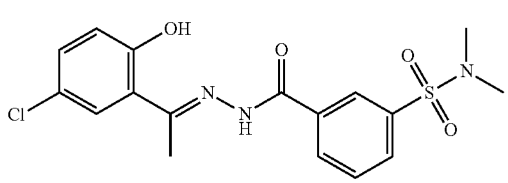 [SMILES: C/C(=N\NC(=O)c1cccc(S(=O)(=O)N(C)C)c1)c1cc(Cl)ccc1O] | −41.96 | −9.87 | 53.92 |

TABLE 2-continued

| No. | Structure | ICM Score | Glide Score | Gold Fitness |
|---|---|---|---|---|
| 19 | (structure) | −27.24 | −6.87 | 43.76 |
| 20 | (structure) | −21.41 | −6.28 | 37.28 |
| 21 | (structure) | −23.11 | −7.21 | 39.84 |
| 22 | (structure) | −19.88 | −6.97 | 37.24 |
| 23 | (structure) | −38.11 | −8.21 | 46.81 |
| 24 | (structure) | −37.11 | −9.23 | 51.65 |
| 25 | (structure) | −39.14 | −8.21 | 49.11 |

5. Molecular Dynamic Simulation Results

Molecular dynamice ("MD") simulations were carried out using the two different docking poses of compound 12 to determine if there was a preference for one docking pose over another. These data can better inform which interactions play a role in the results obtained with the compounds synthesized.

The docking results show the higher ranked pose with compound 12 bound into the dinucleotide binding pocket via direct H-bond interactions with Ser289 or Arg316 via its hydroxyl moiety (binding mode 1, see FIG. 3 and Table 3). However, there is another pose favorably scored with the morpholine ring of compound 12 interacting with Ser289 and Arg316 (binding mode 2, see FIG. 3 and Table 3).

MD using the AMBER suite was used to evaluate the energetics of binding for both predicted binding modes. Simulations for binding mode 1 showed π-conjugated electron interactions between compound 12 and Arg 316 as well as potential for hydrogen bonding between the hydroxyl and Ser289. Analysis of binding mode 2 showed potential π-π interactions between compound 12 and Trp756 with more favorable hydrogen bonds with Arg310 and Arg316. Further, binding mode 1 is predicted to have hydrogen bonding with Val590 while binding mode two has van der Waals interactions involving the chloro group. MMPBSA analysis of the final 100 ps of simulation showed that binding mode 2 was predicted to have a free energy of binding of ~−40.8 kcal/mol, which is nearly 20 kcal/mol more favorable than ~−21.0 for binding mode 1. The first 100 ps of simulation likely reflect in part the equilibration of the complex such that the calculated free energies of binding are not as favorable. This finding contrasts with the rankings of the binding poses during the docking process. It is possible that this difference arises from differences in the protein structure during docking and MD, with a rigid structure used to increase the speed of the docking protocol and a flexible structure used for MD.

TABLE 3

| MD | Compound No. 12 (Binding Mode 1) | Compound No. 12 (Binding Mode 2) |
|---|---|---|
| 1-100 ps: ΔG-bind (kcal/mol) | −20.2154 | −32.9117 |
| 101-200 ps: ΔG-bind (kcal/mol) | −21.0263 | −40.8046 |
| 150-200 ps: ligand RMSD (Å) | 0.394 | 1.560 |

6. Preparation of (E)-N'-(1-(5-chloro-2-hydroxyphenyl)ethylidene)benzohydrazide

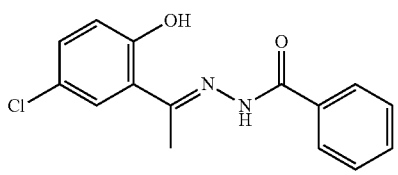 [SMILES: C/C(=N\NC(=O)c1ccccc1)c1cc(Cl)ccc1O]

1-(5-Chloro-2-hydroxyphenyl)ethanone (100 mg, 0.586 mmol) and benzohydrazide (80 mg, 0.586 mmol) were dissolved in methanol (4 mL) in the presence of acetic acid as a catalyst, and then the reaction mixture was heated via microwave irradiation to 120° C. for 30 min. Following cooling, the solvent was removed by vacuum, and the resulting crude material was purified by flash column chromatography (2% $CH_3OH/CH_2Cl_2$) affording the title compound (90 mg) as a solid. $^1$H NMR (400 MHz, DMSO-$d_6$): δ 7.95 (m, 2H), 7.67-7.62 (m, 2H), 7.56 (m, 2H), 7.35 (dd, 1H, J=2.4 & 8.8 Hz), 6.95 (d, 1H, J=8.4 Hz), 3.35 (s, 3H). ESI-MS: 289.0 [M+H]$^+$.

7. Preparation of (E)-N'-(1-(2,6-dihydroxyphenyl)ethylidene)benzohydrazide

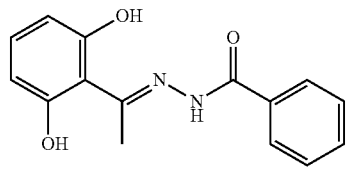 [SMILES: C/C(=N\NC(=O)c1ccccc1)c1c(O)cccc1O]

1-(2,6-Dihydroxyphenyl)ethanone (100 mg, 0.657 mmol) and benzohydrazide (89 mg, 0.657 mmol) were dissolved in methanol (4 mL) in the presence of acetic acid as a catalyst and then the reaction mixture was heated via microwave irradiation to 120° C. for 30 min. Following cooling, the solvent was removed by vacuum, and the resulting crude material was purified by flash column chromatography (2% $CH_3OH/CH_2Cl_2$) affording the title compound (100 mg) as a solid. $^1$H NMR (400 MHz, $CD_3OD$): δ 7.59 (m, 2H), 7.49 (m, 1H), 7.39 (m, 2H), 7.11 (t, 1H, J=8.0 Hz), 6.45 (m, 2H), 2.35 (s, 3H). ESI-MS: 271.1 [M+H]$^+$.

8. Preparation of 3-(Morpholinosulfonyl)benzoic acid

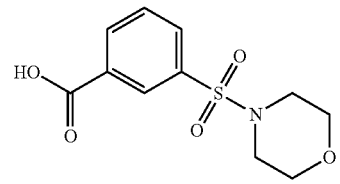

3-(Chlorosulfonyl)benzoic acid (250 mg, 1.133 mmol) was added to morpholine (99 mg, 1.133 mmol) in the presence of potassium carbonate (313 mg, 2.266 mmol) in THF (5 mL) at room temperature, and reaction mixture allowed to stirred for 12 h at rt. The reaction was monitored by TLC. After completion of the reaction, the solvent was removed by vacuum, and then compound was purified by column chromatography (3% $CH_3OH/CH_2Cl_2$) affording the title compound (160 mg) as a solid. $^1$H NMR (400 MHz, $CD_3OD$): δ 8.34 (m, 1H), 8.32 (d, 1H, J=8.0 Hz), 7.99 (m, 1H), 7.76 (t, 1H, J=8.0 Hz), 3.70 (m, 4H), 2.98 (m, 4H). ESI-MS: 272.0 [M+H]$^+$.

9. Preparation of Methyl 3-(morpholinosulfonyl)benzoate

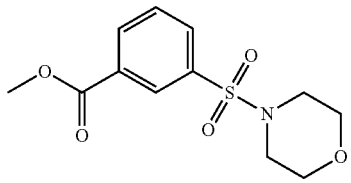 [SMILES: COC(=O)c1cccc(S(=O)(=O)N2CCOCC2)c1]

3-(Morpholinosulfonyl)benzoic acid (100 mg, 0.369 mmol) was refluxed overnight in methanol in the presence of catalytic concentrated $H_2SO_4$ at 65° C. The reaction was monitored by TLC. After completion of the reaction, the solvent was removed by vacuum and then compound was purified by column chromatography to yield the title compound as an off white solid (60 mg). $^1$H NMR (400 MHz, CDCl$_3$): δ 8.38 (t, 1H, J=1.6 Hz), 8.27 (m, 1H), 7.92 (m, 1H), 7.64 (t, 1H, J=8.0 Hz), 3.95 (s, 3H), 3.73 (m, 4H), 3.00 (m, 4H). ESI-MS: 286.1 [M+H]$^+$.

10. Preparation of 3-(morpholinosulfonyl)benzohydrazide

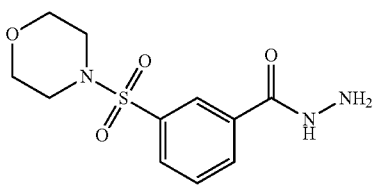 [SMILES: NNC(=O)c1cccc(S(=O)(=O)N2CCOCC2)c1]

Methyl 3-(morpholinosulfonyl)benzoate (120 mg, 0.421 mmol) was added to hydrazine (17.52 mg, 0.547 mmol) in methanol and refluxed for 12 h at 65° C. The reaction was monitored by TLC. Upon completion of the reaction and cooling the reaction mixture, the solvent was removed by vacuum and then compound was purified by column chromatography to yield the title compound as an off white solid (90 mg). $^1$H NMR (400 MHz, CDCl$_3$): δ 8.16 (m, 1H), 8.12 (m, 1H), 8.04 (m, 1H), 7.85 (m, 1H), 7.63 (t, 1H, J=8.0 Hz), 4.19 (m, 2H), 3.71 (m, 4H), 2.97 (m, 4H). ESI-MS: 286.1 [M+H]$^+$.

11. Preparation of (E)-N'-(1-(5-chloro-2-hydroxyphenyl)ethylidene)-3-(morpholinosulfonyl)benzohydrazide

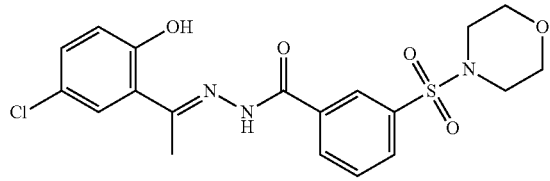 [SMILES: C/C(=N\NC(=O)c1cccc(S(=O)(=O)N2CCOCC2)c1)c1cc(Cl)ccc1O]

1-(5-Chloro-2-hydroxyphenyl)ethanone (20 mg, 0.117 mmol) and 3-(morpholinosulfonyl)benzohydrazide (33.5 mg, 0.117 mmol) were dissolved in methanol (4 mL) in the presence of acetic acid as a catalyst, and the reaction mixture was heated via microwave irradiation to 120° C. for 30 min. Following cooling, the solvent was removed by vacuum and the resulting crude material was purified by flash column chromatography (2% CH$_3$OH/CH$_2$Cl$_2$) affording the title compound (16 mg) as a solid. $^1$H NMR (400 MHz, CD$_3$OD): δ 8.26 (m, 1H), 8.17 (d, 1H, J=8.0 Hz), 7.92 (d, 1H, J=8.0 Hz), 7.72 (t, 1H, J=8.0 Hz), 7.48 (d, 1H, J=2.0 Hz), 7.22 (m, 1H), 6.91 (d, 1H, J=8.8 Hz), 3.72 (m, 4H), 3.01 (m, 4H), 2.43 (s, 3H). ESI-MS: 438.1 [M+H]$^+$.

12. Preparation of (E)-N'-(1-(3-chloro-2-fluorophenyl)ethylidene)-3-(morpholinosulfonyl)benzohydrazide

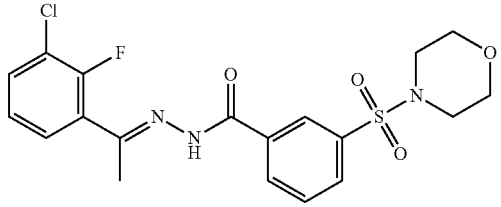 [SMILES: C/C(=N\NC(=O)c1cccc(S(=O)(=O)N2CCOCC2)c1)c1cccc(Cl)c1F]

1-(3-Chloro-2-fluorophenyl)ethanone (20 mg, 0.116 mmol) and 3-(morpholinosulfonyl)benzohydrazide (33.1 mg, 0.116 mmol) were dissolved in methanol (4 mL) in the presence of acetic acid as a catalyst, and the reaction mixture was heated via microwave irradiation to 120° C. for 30 min. Following cooling, the solvent was removed by vacuum and the resulting crude material was purified by flash column chromatography (2% CH$_3$OH/CH$_2$Cl$_2$) affording the title compound (22 mg) as a solid. $^1$H NMR (400 MHz, CDCl$_3$): δ 9.43 (s, 1H), 8.37 (m, 1H), 8.16 (m, 1H), 7.87 (d, 1H, J=7.2 Hz), 7.65 (m, 1H), 7.41 (m, 1H), 7.10 (t, 1H, J=8.0 Hz), 3.71 (m, 4H), 2.95 (m, 4H), 2.38 (s, 3H). ESI-MS: 440.1 [M+H]$^+$.

13. Preparation of (E)-N'-(1-(2-chloropyridin-4-yl)ethylidene)-3-(morpholinosulfonyl)benzohydrazide

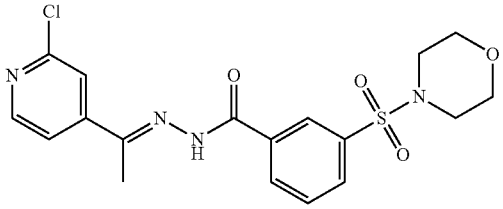 [SMILES: C/C(=N\NC(=O)c1cccc(S(=O)(=O)N2CCOCC2)c1)c1ccnc(Cl)c1]

1-(2-Chloropyridin-4-yl)ethanone (20 mg, 0.129 mmol) and 3-(morpholinosulfonyl)benzohydrazide (36.7 mg, 0.129 mmol) were dissolved in methanol (4 mL) in the presence of acetic acid as a catalyst, and the reaction mixture was heated via microwave irradiation to 120° C. for 30 min. Following cooling, the solvent was removed by vacuum and the resulting crude material was purified by flash column chromatography affording the title compound in a 60% yield. $^1$H NMR (400 MHz, CDCl$_3$): δ 9.43 (m, 1H), 8.39 (m, 2H), 8.15 (d, 1H, J=8.0 Hz), 7.93 (d, 1H, J=7.6 Hz), 7.70 (t, 1H, J=7.6 Hz), 7.52 (m, 1H), 3.73 (m, 4H), 3.02 (m, 4H), 2.35 (s, 3H). ESI-MS: 423.1 [M+H]$^+$.

14. Preparation of (E)-N'-(1-(2,5-dichlorophenyl)ethylidene)-3-(morpholinosulfonyl)benzohydrazide

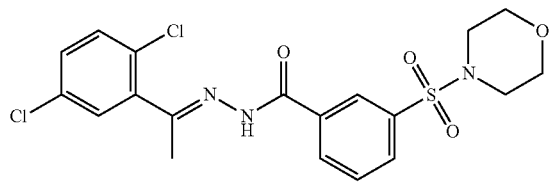 [SMILES: C/C(=N\NC(=O)c1cccc(S(=O)(=O)N2CCOCC2)c1)c1cc(Cl)ccc1Cl]

1-(2,5-Dichlorophenyl)ethanone (20 mg, 0.106 mmol) and 3-(morpholinosulfonyl)benzohydrazide (30.2 mg, 0.106 mmol) were dissolved in methanol (4 mL) in the presence of acetic acid as a catalyst, and the reaction mixture was heated via microwave irradiation to 120° C. for 30 min. Following cooling, the solvent was removed by vacuum and the resulting crude material was purified by flash column chromatography affording the title compound in a 10 mg yield. $^1$H NMR (400 MHz, CDCl$_3$): δ 8.29 (m, 1H), 8.09 (m, 1H), 7.81 (m, 1H), 7.57 (m, 1H), 7.40 (m, 1H), 7.26 (m, 2H), 3.52 (m, 4H), 2.91 (m, 4H), 2.28 (s, 3H). ESI-MS: 456.1 [M+H]$^+$.

15. Preparation of Methyl 4-hydrazinyl-3-(morpholinosulfonyl)benzoate

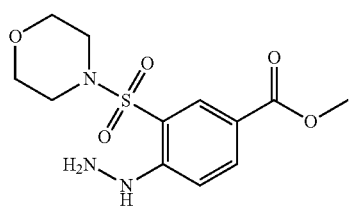 [SMILES: COC(=O)c1ccc(NN)c(S(=O)(=O)N2CCOCC2)c1]

Methyl 4-fluoro-3-(morpholinosulfonyl)benzoate (30 mg, 0.099 mmol) was added to hydrazine (4.44 mg, 0.138 mmol) in methanol (8 mL) and refluxed for 5 h at 65° C. The reaction was monitored by TLC. Upon completion of the reaction and cooling, the solvent was removed by vacuum, and the compound was purified by column chromatography affording the title compound (20 mg). $^1$H NMR (400 MHz, CD$_3$OD): δ 8.15 (d, 1H, J=2.0 Hz), 8.03 (dd, 1H, J=2.4 & 9.2 Hz), 7.48 (d, 1H, J=9.2 Hz), 3.86 (s, 3H), 3.67 (m, 4H), 3.04 (m, 4H). ESI-MS: 316.1 [M+H]$^+$.

16. Preparation of Methyl 4-fluoro-3-(morpholinosulfonyl)benzoate

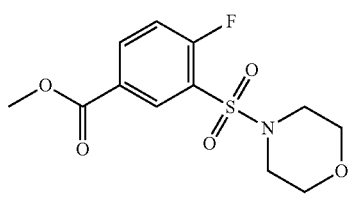 [SMILES: COC(=O)c1ccc(F)c(S(=O)(=O)N2CCOCC2)c1]

4-Fluoro-3-(morpholinosulfonyl)benzoic acid (50 mg, 0.173 mmol) was refluxed overnight in the presence of concentrated sulfuric acid (1.117 mg, 8.64 µmol) in methanol (8 mL) at 70° C. The reaction was monitored by TLC. After completion of the reaction, the solvent was removed by vacuum and compound was purified by column chromatography affording the title compound (20 mg). $^1$H NMR (400 MHz, CD$_3$OD): δ 8.42 (dd, 1H, J=2.0 & 6.4 Hz), 8.33 (m, 1H), 7.49 (t, 1H, J=8.8 Hz), 3.94 (s, 3H), 3.71 (m, 4H), 3.16 (m, 4H).

17. Preparation of Methyl 3-bromo-4-chlorobenzoate

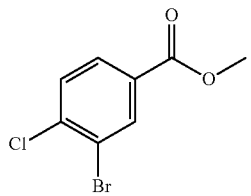

3-Bromo-4-chlorobenzoic acid (200 mg, 0.849 mmol) was refluxed in the presence of concentrated sulfuric acid (5.49 mg, 0.042 mmol) in methanol (10 mL) at 70° C. for overnight. The reaction was monitored by TLC. After completion of the reaction, the solvent was removed by vacuum, and the compound was purified by column chromatography affording the title compound (130 mg). $^1$H NMR (400 MHz, CDCl$_3$): δ 8.29 (d, 1H, J=2.0 Hz), 7.91 (dd, 1H, J=2.0 & 8.4 Hz), 7.52 (d, 1H, J=8.4 Hz), 3.92 (s, 3H). ESI-MS: 250.9 [M+H]$^+$.

18. Preparation of Methyl 3-(N,N-dimethylsulfamoyl)benzoate

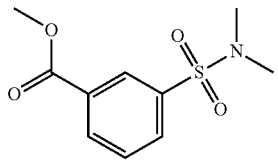 [SMILES: COC(=O)c1cccc(S(=O)(=O)N(C)C)c1]

3-(N,N-Dimethylsulfamoyl)benzoic acid (200 mg, 0.872 mmol) was refluxed overnight in the presence of concentrated sulfuric acid (5.64 mg, 0.044 mmol) in methanol (10 mL) at 70° C. Reaction was monitored by TLC. After completion of the reaction, the solvent was removed by vacuum and then compound was purified by column chromatography affording the title compound (125 mg). $^1$H NMR (400 MHz, CDCl$_3$): δ 8.42 (s, 1H), 8.27 (d, 1H, J=8.0 Hz), 7.97 (d, 1H, J=7.2 Hz), 7.65 (t, 1H, J=8.0 Hz), 3.96 (s, 3H), 2.74 (s, 6H). ESI-MS: 244.0 [M+H]$^+$.

19. Preparation of 3-bromo-4-chlorobenzohydrazide

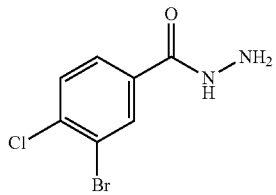 [SMILES: NNC(=O)c1ccc(Cl)c(Br)c1]

Methyl 3-bromo-4-chlorobenzoate (120 mg, 0.481 mmol) was added to hydrazine (23.12 mg, 0.721 mmol) in methanol (8 mL) and refluxed for 12 h at 70° C. Reaction was monitored by TLC. After completion of the reaction, the solvent was removed by vacuum and then compound was purified by column chromatography affording the title compound (30 mg). $^1$H NMR (400 MHz, CDCl$_3$): δ 8.02 (d, 1H, J=1.6 Hz), 7.60 (dd, 1H, J=2.0 & 8.0 Hz), 7.52 (d, 1H, J=8.0 Hz). ESI-MS: 250.9 [M+H]$^+$.

20. Preparation of 3-(hydrazinecarbonyl)-N,N-dimethylbenzenesulfonamide

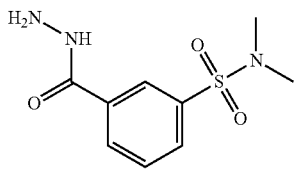 [SMILES: CN(C)S(=O)(=O)c1cccc(C(=O)NN)c1]

Methyl 3-(N,N-dimethylsulfamoyl)benzoate (150 mg, 0.617 mmol) was added to hydrazine (29.6 mg, 0.925 mmol) in methanol (10 mL) and refluxed for 8 h at 65° C. Following cooling, the reaction was monitored by TLC. After completion of the reaction, the solvent was removed by vacuum and the compound was purified by column chromatography affording the title compound (60 mg). $^1$H NMR (400 MHz, CDCl$_3$): δ 8.11 (s, 1H), 8.01 (d, 1H, J=8.4 Hz), 7.92 (d, 1H, J=8.0 Hz), 7.65 (t, 1H, J=8.0 Hz), 2.73 (5, 6H). ESI-MS: 244.0 [M+H]$^+$.

1. Preparation of (E)-3-bromo-4-chloro-N'-(1-(5-chloro-2-hydroxyphenyl)ethylidene)benzohydrazide

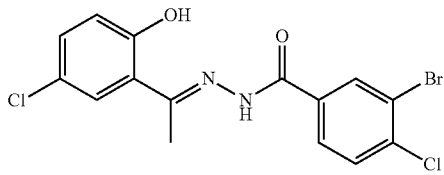 [SMILES: C/C(=N\NC(=O)c1ccc(Cl)c(Br)c1)c1cc(Cl)ccc1O]

3-Bromo-4-chlorobenzohydrazide (30 mg, 0.120 mmol) and 1-(5-chloro-2-hydroxyphenyl)ethanone (20.51 mg, 0.120 mmol) were dissolved in methanol (4 mL) in the presence of acetic acid as a catalyst, and the reaction mixture was heated via microwave irradiation to 120° C. for 30 min. The reaction was monitored by TLC. Upon completion of the reaction and following cooling, the solvent was removed by vacuum, and the resulting crude material was purified by flash column chromatography (2% CH$_3$OH/CH$_2$Cl$_2$) affording the title compound (15 mg). $^1$H NMR (400 MHz, acetone-d$_5$): δ 8.30 (s, 1H), 7.98 (d, 1H, J=8.4 Hz), 7.73 (d, 1H, J=8.4 Hz), 7.61 (d, 1H, J=2.4 Hz), 7.29 (dd, 1H, J=2.4 & 8.4 Hz), 6.93 (d, 1H, J=8.8 Hz), 2.55 (s, 3H). ESI-MS: 402.9 [M+H]$^+$.

22. Preparation of (E)-3-(2-(1-(5-chloro-2-hydroxyphenyl)ethylidene)hydrazinecarbonyl)-N,N-dimethylbenzenesulfonamide

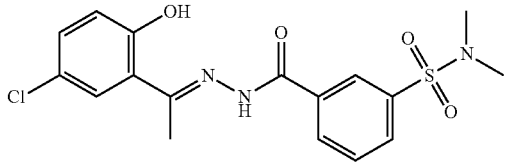

3-(Hydrazinecarbonyl)-N,N-dimethylbenzenesulfonamide (50 mg, 0.0.206 mmol) and 1-(5-chloro-2-hydroxyphenyl)ethanone (35.1 mg, 0.206 mmol) were dissolved in methanol (4 mL) in the presence of acetic acid as a catalyst, and the reaction mixture was heated via microwave irradiation to 120° C. for 30 min. The reaction was monitored by TLC. Upon completion of the reaction and following cooling, the solvent was removed by vacuum, and the resulting crude material was purified by flash column chromatography (2% CH$_3$OH/CH$_2$Cl$_2$) affording the title compound as a solid (15 mg). $^1$H NMR (400 MHz, acetone-d$_6$): δ 8.29 (m, 2H), 8.01 (d, 1H, J=8.4 Hz), 7.83 (t, 1H, J=8.4 Hz), 7.62 (d, 1H, J=2.4 Hz), 7.32 (dd, 1H, J=2.4 & 8.8 Hz), 6.96 (d, 1H, J=8.8 Hz), 2.73 (s, 6H), 2.58 (s, 3H). ESI-MS: 396.0 [M+H]$^+$.

23. Preparation of 5-bromo-6-chloronicotinohydrazide

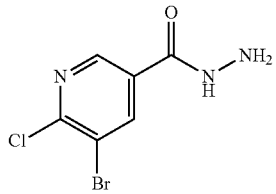 [SMILES: NNC(=O)c1cnc(Cl)c(Br)c1]

Methyl 5-bromo-6-chloronicotinate (100 mg, 0.399 mmol) was added to hydrazine (19.19 mg, 0.599 mmol) in methanol (8 mL) and heated overnight at 70° C. The reaction was monitored by TLC. Upon completion of the reaction, the solvent was removed by vacuum, and the compound was purified by column chromatography affording the title compound (20 mg). $^1$H NMR (400 MHz, CD$_3$OD): δ 8.33 (d, 1H, J=2.4 Hz), 8.01 (d, 1H, J=2.4 Hz).

24. Preparation of (E)-5-bromo-6-chloro-N'-(1-(5-chloro-2-hydroxyphenyl)ethylidene)nicotinohydrazide

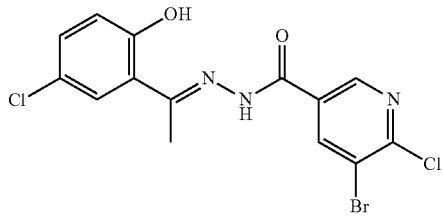 [SMILES: C/C(=N\NC(=O)c1cnc(Cl)c(Br)c1)c1cc(Cl)ccc1O]

5-Bromo-6-chloronicotinohydrazide (15 mg, 0.060 mmol) and 1-(5-chloro-2-hydroxyphenyl)ethanone (10.22 mg, 0.060 mmol) were dissolved in methanol (4 mL) in the presence of acetic acid as a catalyst and the reaction mixture was heated via microwave irradiation to 120° C. for 30 min. The reaction was monitored by TLC. Upon completion of the reaction and following cooling, the solvent was removed by vacuum, and the resulting crude material was purified by flash column chromatography (2% CH$_3$OH/CH$_2$Cl$_2$) affording the title compound as a solid (8 mg). $^1$H NMR (400 MHz, DMSO-d$_6$): δ 8.39 (d, 1H, J=2.4 Hz), 8.28 (s, 1H), 7.63 (d, 1H, J=2.4 Hz), 7.32 (dd, 1H, J=2.4 & 8.8 Hz), 7.06 (d, 1H, J=6.8 Hz), 6.92 (d, 1H, J=9.2 Hz), 6.81 (d, 1H, J=6.8 Hz), 2.47 (s, 3H). ESI-MS: 404.0 [M+H]$^+$.

25. Preparation of Methyl 5-chloronicotinate

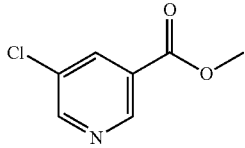

5-Chloronicotinic acid (200 mg, 1.269 mmol) was refluxed overnight in the presence of concentrated sulfuric acid (8.20 mg, 0.063 mmol) in methanol (10 mL) at 70° C. The reaction was monitored by TLC. After completion of the reaction, the solvent was removed by vacuum and the compound was purified by column chromatography affording the title compound (120 mg). $^1$H NMR (400 MHz, CDCl$_3$): δ 9.07 (d, 1H, J=1.6 Hz), 8.72 (d, 1H, J=2.0 Hz), 8.26 (m, 1H), 3.95 (s, 1H).

26. Preparation of Methyl 5-chloronicotinate

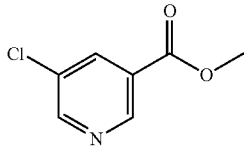

5-Chloronicotinic acid (200 mg, 1.269 mmol) was refluxed overnight in the presence of concentrated sulfuric acid (8.20 mg, 0.063 mmol) in methanol (8 mL) at 70° C. The reaction was monitored by TLC. After completion of the reaction, the solvent was removed by vacuum and the compound was purified by column chromatography affording the title compound (120 mg). $^1$H NMR (400 MHz, CDCl$_3$): δ 9.07 (d, 1H, J=1.6 Hz), 8.72 (d, 1H, J=2.0 Hz), 8.26 (m, 1H), 3.95 (s, 1H).

27. Preparation of 5-chloronicotinohydrazide

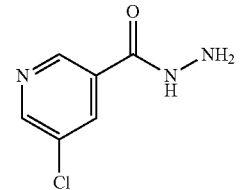 [SMILES: NNC(=O)c1cncc(Cl)c1]

Hydrazine (17.93 mg, 0.560 mmol) was added to methyl 5-chloronicotinate (80 mg, 0.466 mmol) in methanol (8 mL) and heated overnight at 70° C. The reaction was monitored by TLC. After completion of the reaction, the solvent was removed by vacuum and the compound was purified by column chromatography affording the title compound (40 mg). $^1$H NMR (400 MHz, CD$_3$OD): δ 8.85 (d, 1H, J=2.0 Hz), 8.70 (d, 1H, J=2.4 Hz), 8.22 (t, 1H, J=2.0 Hz). ESI-MS: 172.0 [M+H]$^+$.

28. Preparation of (E)-5-chloro-N'-(1-(5-chloro-2-hydroxyphenyl)ethylidene)nicotinohydrazide

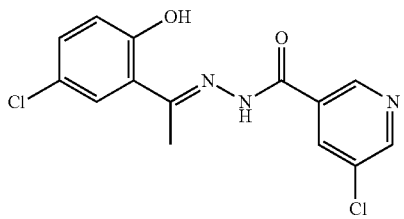 [SMILES: C/C(=N\NC(=O)c1cncc(Cl)c1)c1cc(Cl)ccc1O]

5-Chloronicotinohydrazide (30 mg, 0.175 mmol) and 1-(5-chloro-2-hydroxyphenyl)ethanone (29.8 mg, 0.175 mmol) were dissolved in methanol (4 mL) in the presence of acetic acid as a catalyst, and the reaction mixture was heated via microwave irradiation to 120° C. for 30 min. The reaction was monitored by TLC. Upon completion of the reaction and following cooling, the solvent was removed by vacuum, and the resulting crude material was purified by flash column chromatography (2% CH$_3$OH/CH$_2$Cl$_2$) affording the title compound as a solid (20 mg). $^1$H NMR (400 MHz, acetone-d$_6$): δ 9.06 (s, 1H), 8.77 (s, 1H), 8.37 (s, 1H), 7.62 (d, 1H, J=2.8 Hz), 7.31 (dd, 1H, J=2.0 & 8.4 Hz), 6.95 (d, 1H, J=8.8 Hz), 2.58 (s, 3H). ESI-MS: 324.0 [M+H]$^+$.

29. Preparation of (E)-N'-(1-chloro-2-hydroxyphenyl)propylidene)-3-(morpholinosulfonyl)benzohydrazide

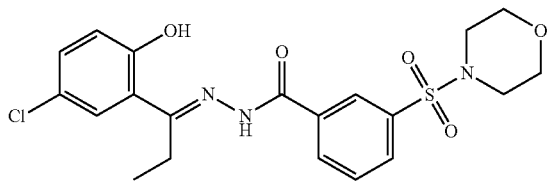 [SMILES: CC/C(=N\NC(=O)c1cccc(S(=O)(=O)N2CCOCC2)c1)c1cc(Cl)ccc1O]

3-(Morpholinosulfonyl)benzohydrazide (40 mg, 0.140 mmol) and 1-(5-chloro-2-hydroxyphenyl)propan-1-one (25.9 mg, 0.140 mmol) were dissolved in methanol (4 mL) in the presence of acetic acid as a catalyst, and the reaction mixture was heated via microwave irradiation to 120° C. for 30 min. The reaction was monitored by TLC. Upon completion of the reaction and following cooling, the solvent was removed by vacuum, and the resulting crude material was purified by flash column chromatography (2% CH$_3$OH/CH$_2$Cl$_2$) affording the title compound as a solid (20 mg). $^1$H NMR (400 MHz, acetone-d$_6$): δ 8.26 (m, 2H), 8.00 (d, 1H, J=7.6 Hz), 7.84 (t, 1H, J=8.0 Hz), 7.64 (d, 1H, J=2.4 Hz), 7.33 (m, 1H), 6.98 (d, 1H, J=9.2 Hz), 3.69 (m, 4H), 3.10 (q, 2H, J=7.6 Hz), 2.99 (m, 4H), 1.26 (t, 3H, J=7.6 Hz). ESI-MS: 452.1 [M+H]$^+$.

30. Preparation of (E)-3-(morpholinosulfonyl)-N'-(1-(pyridin-3-yl)ethylidene)benzohydrazide

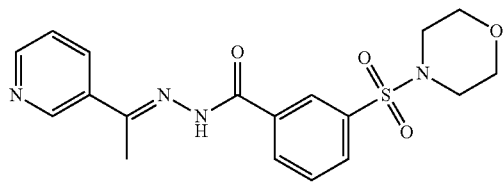

3-(Morpholinosulfonyl)benzohydrazide (40 mg, 0.140 mmol) and 1-(pyridin-3-yl)ethanone (16.98 mg, 0.140 mmol) were dissolved in methanol (4 mL) in the presence of acetic acid as a catalyst, and the reaction mixture was heated via microwave irradiation to 120° C. for 30 min. The reaction was monitored by TLC. Upon completion of the reaction and following cooling, the solvent was removed by vacuum, and the resulting crude material was purified by flash column chromatography (2% $CH_3OH/CH_2Cl_2$) affording the title compound as a solid (15 mg). $^1$H NMR (400 MHz, $CDCl_3$): δ 9.53 (bs, 1H), 8.87 (s, 1H), 8.59 (m, 1H), 8.39 (m, 1H), 8.17 (m, 1H), 7.98 (m, 1H), 7.89 (d, 1H, J=8.0 Hz), 7.67 (t, 1H, J=8.0 Hz), 7.32 (m, 1H), 3.70 (m, 4H), 3.00 (m, 4H), 2.39 (s, 3H). ESI-MS: 389.0 [M+H]$^+$.

31. Preparation of 3-morpholinobenzohydrazide

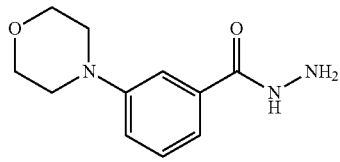 [SMILES: NNC(=O)c1cccc(N2CCOCC2)c1]

Methyl 3-morpholinobenzoate (100 mg, 0.452 mmol) was added to hydrazine (14.48 mg, 0.452 mmol) in methanol (10 mL) and refluxed for 12 h at 65° C. The reaction was monitored by TLC. Upon completion of the reaction and following cooling, the solvent was removed by vacuum and the compound was purified by column chromatography (2% $CH3OH/CH_2Cl_2$) affording the title compound as a solid (52 mg). $^1$H NMR (400 MHz, DMSO-$d_6$): δ 9.69 (s, 1H), 7.35 (s, 1H), 7.27 (m, 2H), 7.07 (m, 1H), 4.45 (bs, 2H), 3.74 (m, 4H), 3.14 (m, 4H). ESI-MS: 222.1 [M+H]$^+$.

32. Preparation of (E)-N'-(1-(5-chloro-2-hydroxyphenyl)ethylidene)-3-morpholinobenzohydrazide

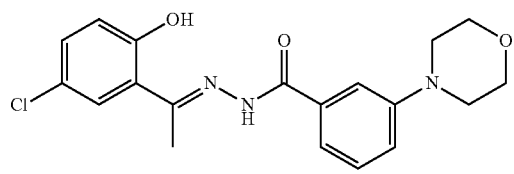 [SMILES: C/C(=N\NC(=O)c1cccc(N2CCOCC2)c1)c1cc(Cl)ccc1O]

1-(5-Chloro-2-hydroxyphenyl)ethanone (40 mg, 0.234 mmol) and 3-morpholinobenzohydrazide (51.9 mg, 0.234 mmol) were dissolved in methanol (4 mL) in the presence of acetic acid as a catalyst, and the reaction mixture was heated via microwave irradiation to 120° C. for 30 min. The reaction was monitored by TLC. Upon completion of the reaction and following cooling, the solvent was removed by vacuum, and the resulting crude material was purified by flash column chromatography (2% $CH_3OH/CH_2Cl_2$) affording the title compound (60 mg) as a solid. $^1$H NMR (400 MHz, DMSO-$d_6$): δ 7.65 (d, 1H, J=2.4 Hz), 7.42-7.32 (m, 4H), 7.20 (m, 1H), 6.94 (d, 1H, J=8.8 Hz), 3.77 (m, 4H), 3.19 (m, 4H), 2.48 (s, 3H). ESI-MS: 374.1 [M+H]$^+$.

33. Preparation of 5-(methylsulfonyl)nicotinohydrazide

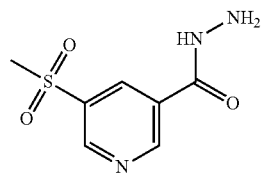

Methyl 5-(methylsulfonyl)nicotinate (100 mg, 0.465 mmol) were added to hydrazine (17.87 mg, 0.558 mmol) in methanol (10 mL) and refluxed for 12 h at 70° C. The reaction was monitored by TLC. Upon completion of the reaction and following cooling, the solvent was removed by vacuum and the compound was purified by flash column chromatography (3% $CH_3OH/CH_2Cl_2$) afforded the title compound (83 mg, 80% yield) as a solid. $^1$H NMR (400 MHz, $CDCl_3$): δ 9.20 (d, 1H, J=2.0 Hz), 9.17 (d, 1H, J=2.0 Hz), 8.61 (s, 1H), 3.11 (s, 3H). ESI-MS: 216.1 [M+H]$^+$.

34. Preparation of (E)-N'-(1-(5-chloro-2-hydroxyphenyl)ethylidene)-5-(methylsulfonyl)nicotinohydrazide

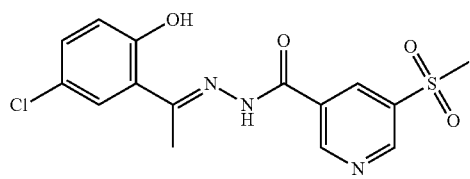 [SMILES: C/C(=N\NC(=O)c1cncc(S(C)(=O)=O)c1)c1cc(Cl)ccc1O]

1-(5-Chloro-2-hydroxyphenyl)ethanone (50 mg, 0.293 mmol) and 5-(methylsulfonyl) nicotinohydrazide (63.1 mg, 0.293 mmol) were dissolved in methanol (4 mL) in the presence of acetic acid as a catalyst, and the reaction mixture was heated via microwave irradiation to 120° C. for 30 min. The reaction was monitored by TLC. Upon completion of the reaction and following cooling, the solvent was removed by vacuum, and the resulting crude material was purified by flash column chromatography (3% $CH_3OH/CH_2Cl_2$) affording the title compound (70 mg, 63.0% yield) as a solid. $^1$H NMR (400 MHz, DMSO-$d_6$): δ 11.86 (s, 1H), 9.37 (s, 1H), 9.27 (s, 1H), 8.76 (s, 1H), 7.68 (s, 1H), 7.36 (d, 1H, J=8.8 Hz), 6.97 (d, 1H, J=8.8 Hz), 3.42 (s, 3H), 2.53 (s, 3H). ESI-MS: 368.8 [M+H]$^+$.

35. Preparation of 3-(methylsulfonyl)benzohydrazide

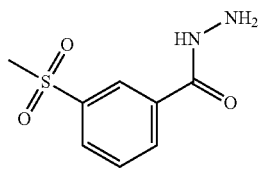

Methyl 3-(methylsulfonyl)benzoate (100 mg, 0.467 mmol) was added to hydrazine (22.44 mg, 0.700 mmol)) in methanol (10 mL) and refluxed for 12 h at 70° C. The reaction was monitored by TLC. Upon completion of the reaction and following cooling, the solvent was removed by vacuum, and the compound was purified by flash column chromatography (3% $CH_3OH/CH_2Cl_2$) affording the title compound (80 mg, 80% yield) as a solid. $^1H$ NMR (400 MHz, $CDCl_3$): δ 8.28 (s, 1H), 8.07 (d, 1H, J=7.6 Hz), 8.01 (d, 1H, J=7.6 Hz), 7.62 (t, 1H, J=7.6 Hz), 3.04 (5, 3H). ESI-MS: 215.1 [M+H]$^+$.

36. Preparation of (E)-N'-(1-(5-chloro-2-hydroxyphenyl)ethylidene)-3-(methylsulfonyl)benzohydrazide

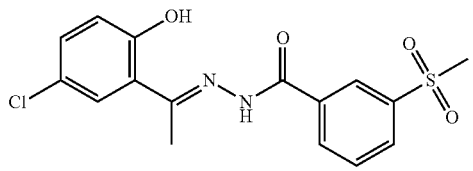 [SMILES: C/C(=N\NC(=O)c1cccc(S(C)(=O)=O)c1)c1cc(Cl)ccc1O]

1-(5-Chloro-2-hydroxyphenyl)ethanone (55 mg, 0.322 mmol) and 3-(methylsulfonyl)benzohydrazide (69.1 mg, 0.322 mmol) were dissolved in methanol (5 mL) in the presence of acetic acid as a catalyst, and the reaction mixture was heated via microwave irradiation to 120° C. for 30 min. The reaction was monitored by TLC. Upon completion of the reaction and following cooling, the solvent was removed by vacuum, and the resulting crude material was purified by flash column chromatography (3% $CH_3OH/CH_2Cl_2$) affording the title compound (75 mg, 63.4% yield) as a solid. $^1H$ NMR (400 MHz, $CD_3OD$): δ 8.49 (s, 1H), 8.26 (d, 1H, J=8.4 Hz), 8.18 (d, 1H, J=7.6 Hz), 7.80 (t, 1H, J=7.6 Hz), 7.60 (d, 1H, J=2.4 Hz), 7.27 (m, 1H), 6.93 (d, 1H, J=8.8 Hz), 3.19 (s, 3H), 2.49 (s, 3H). ESI-MS: 367.8 [M+H]$^+$.

37. Preparation of 3-((4-methylpiperidin-1-yl)sulfonyl)benzoic acid

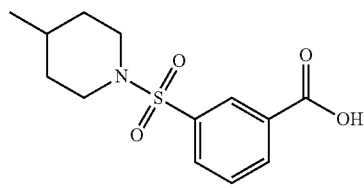

4-methylpiperidine (180 mg, 1.813 mmol) was added to the 3-(chlorosulfonyl)benzoic acid (200 mg, 0.906 mmol) in presence of Potassiumcarbonate (251 mg, 1.813 mmol) in THF (Volume: 5 ml) at room temperature and the reaction mixture was stirred for 12 h at room temperature. Reaction was monitored by TLC. After completion of the reaction, the solvent was removed by vacuum and then compound was purified by column chromatography (3% $CH_3OH/CH_2Cl_2$) afforded the title compound as a solid. 1H NMR ($CD_3OD$, 400 MHz): δ 8.32 (m, 1H), 8.27 (m, 1H), 7.96 (m, 1H), 7.72 (t, 1H, J=8.0 Hz), 3.72 (m, 2H), 2.27 (m, 2H), 1.68 (m, 2H), 1.29 (m, 1H), 1.21 (m, 2H), 0.88 (d, 3H, J=6.4 Hz). ESI-MS: 284.1 [M+H]+

38. Preparation of methyl 3-((4-methylpiperidin-1-yl)sulfonyl)benzoate

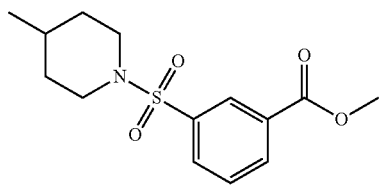

3-((4-methylpiperidin-1-yl)sulfonyl)benzoic acid (120 mg, 0.424 mmol) was refluxed in the presence of con. Sulfuric acid (2.74 mg, 0.021 mmol) in methanol at 70° C. for overnight. Reaction was monitored by TLC. After completion of the reaction, the solvent was removed by vacuum and then compound was purified by flash chromatography afforded the methyl 3-((4-methylpiperidin-1-yl)sulfonyl)benzoate (100 mg, 0.319 mmol, 75% yield). 1H NMR (CDCl3, 400 MHz): δ 8.39 (m, 1H), 8.25 (m, 1H), 7.94 (m, 1H), 7.62 (t, 1H, J=7.6 Hz), 3.95 (s, 3H), 3.77 (m, 2H), 2.25 (m, 2H), 1.67 (m, 2H), 1.29 (m, 3H), 0.90 (d, 3H, J=4.8 Hz). ESI-MS: 298.1[M+H]+

39. Preparation of 2-(morpholinosulfonyl)benzohydrazide

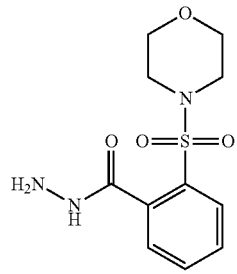

Hydrazine (22.46 mg, 0.701 mmol) was added to the methyl 2-(morpholinosulfonyl)benzoate (100 mg, 0.350 mmol) in methanol and refluxed for 12 h at 70° C. Following cooling, Reaction was monitored by TLC. After completion of the reaction, the solvent was removed by vacuum and then compound was purified by flash chromatography afforded the title compound 2-(morpholinosulfonyl)benzohydrazide (40 mg, 0.129 mmol, 36.8% yield) as a solid. 1H NMR (CDCl3, 400 MHz): δ 7.86 (m, 1H), 7.66-7.56 (m, 2H), 7.52 (dd, 1H, J=1.2 & 7.6 Hz), 7.40 (m, 1H), 4.09 (m, 2H), 3.70 (m, 4H), 3.15 (m, 4H). ESI-MS: 286.1[M+H]+

40. Preparation of 3-((4-methylpiperidin-1-yl)sulfonyl)benzohydrazide

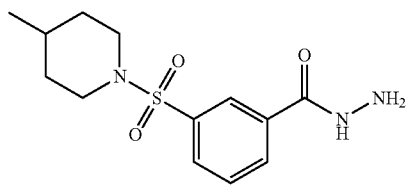

Methyl 3-((4-methylpiperidin-1-yl)sulfonyl)benzoate (100 mg, 0.336 mmol) was added to the hydrazine (21.55 mg, 0.673 mmol) in methanol and refluxed for 8 h at 65° C. Following cooling, reaction was monitored by TLC. After completion of the reaction, the solvent was removed by vacuum and then compound was purified by column chromatography to yield 3-((4-methylpiperidin-1-yl)sulfonyl)benzohydrazide (70 mg, 0.217 mmol, 64.4% yield). 1H NMR (CD3OD, 400 MHz): δ 8.16 (m, 1H), 8.05 (m, 1H), 7.91 (m, 1H), 7.70 (t, 1H, J=7.6 Hz), 3.74 (m, 2H), 2.28 (m, 2H), 1.69 (m, 2H), 1.32-1.16 (m, 3H), 0.90 (d, 3H, J=6.0 Hz). ESI-MS: 298.1[M+H]+

41. Preparation of (E)-N'-(1-(5-chloro-2-hydroxyphenyl)ethylidene)-3-((4-methylpiperidin-1-yl)sulfonyl)benzohydrazide

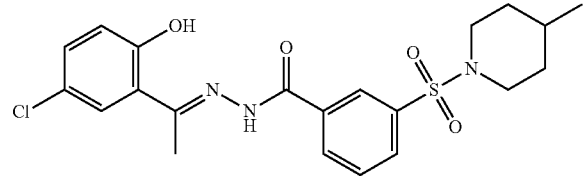 [SMILES: C/C(=N\NC(=O)c1cccc(S(=O)(=O)N2CCC(C)CC2)c1)c1cc(Cl)ccc1O]

3-((4-methylpiperidin-1-yl)sulfonyl)benzohydrazide (70 mg, 0.235 mmol) and 1-(5-chloro-2-hydroxyphenyl)ethanone (40.2 mg, 0.235 mmol) was dissolved in Methanol (Volume: 4 ml) in the presence of acetic acid as a catalyst and then the reaction mixture was heated via microwave irradiation to 120° C. for 30 min. Reaction was monitored by TLC. After completion of the reaction, following cooling, the solvent was removed by vacuum and the resulting crude material was purified by flash column chromatography (2% CH3OH/CH2Cl2) afforded the title compound (E)-N'-(1-(5-chloro-2-hydroxyphenyl)ethylidene)-3-((4-methylpiperidin-1-yl)sulfonyl)benzohydrazide (15 mg, 0.032 mmol, 13.60% yield) as a solid. 1H NMR (CDCl3, 400 MHz): δ 8.11 (m, 2H), 7.81 (m, 1H), 7.59 (m, 1H), 7.39 (m, 1H), 7.19 (m, 1H), 6.89 (m, 1H), 3.69 (m, 2H), 2.41 (m, 2H), 2.24 (m, 2H), 1.63 (m, 2H), 1.24 (m, 4H), 0.87 (d, 3H, J=4.4 Hz). Mass [M+H]+: 450.2

42. Preparation of (E)-N'-(1-(5-chloro-2-fluorophenyl)ethylidene)-3-(morpholinosulfonyl)benzohydrazide

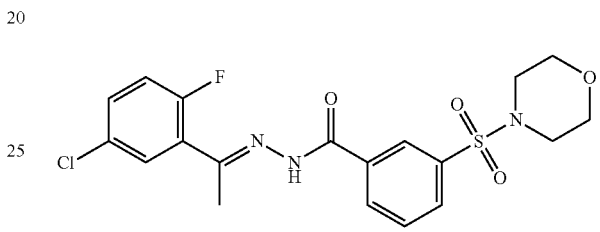

1-(5-chloro-2-fluorophenyl)ethanone (20 mg, 0.116 mmol) and 3-(morpholinosulfonyl)benzohydrazide (33.1 mg, 0.116 mmol) was dissolved in Methanol (Volume: 4 ml) in the presence of acetic acid as a catalyst and then the reaction mixture was heated via microwave irradiation to 120° C. for 30 min. Reaction was monitored by TLC. After completion of the reaction, following cooling, the solvent was removed by vacuum and the resulting crude material was purified by flash column chromatography (2% CH3OH/CH2Cl2) afforded the title compound (E)-N'-(1-(5-chloro-2-fluorophenyl)ethylidene)-3-(morpholinosulfonyl)benzohydrazide (10 mg, 0.022 mmol, 19.22% yield) as a solid. 1H NMR (CDCl3, 400 MHz): δ 8.26 (m, 1H), 8.09 (m, 1H), 7.80 (d, 1H, J=7.6 Hz), 7.58 (t, 1H, J=7.6 Hz), 7.37 (m, 1H), 7.21 (m, 1H), 6.95 (m, 1H), 3.61 (m, 4H), 2.90 (m, 4H), 2.29 (s, 3H). Mass [M+H]+: 440.1

43. Preparation of methyl 3-(pyrrolidin-1-ylsulfonyl)benzoate

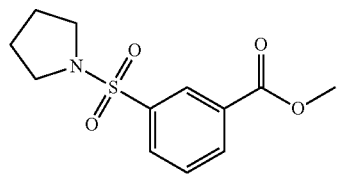 [SMILES: COC(=O)c1cccc(S(=O)(=O)N2CCCC2)c1]

3-(pyrrolidin-1-ylsulfonyl)benzoic acid (200 mg, 0.783 mmol) was refluxed in the presence of con. Sulfuric acid (5.06 mg, 0.039 mmol) in methanol at 70° C. for overnight. Reaction was monitored by TLC. After completion of the reaction, solvent was removed by vacuum and then compound was purified by flash chromatography afforded the methyl 3-(pyrrolidin-1-ylsulfonyl)benzoate (150 mg, 0.535 mmol, 68.3% yield). 1H NMR (CDCl3, 400 MHz): δ 8.47 (m, 1H), 8.25 (d, 1H, J=7.6 Hz), 8.02 (dt, 1H, J=1.2 & 8.0 Hz), 7.63 (t, 1H, J=7.6 Hz), 3.96 (s, 3H), 3.27 (m, 4H), 1.77 (m, 4H). Mass [M+H]+: 270.1

44. Preparation of methyl 3-(N-methylsulfamoyl)benzoate

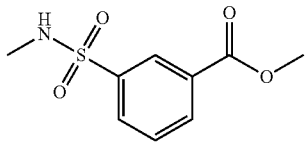

3-(N-methylsulfamoyl)benzoic acid (200 mg, 0.929 mmol) was refluxed in the presence of concentrated sulfuric acid (6.01 mg, 0.046 mmol) in methanol at 70° C. for overnight. Reaction was monitored by TLC. After completion of the reaction, the solvent was removed by vacuum and then compound was purified by flash chromatography afforded the methyl 3-(N-methylsulfamoyl)benzoate (120 mg, 0.497 mmol, 53.5% yield). 1H NMR (CDCl3, 400 MHz): δ 8.51 (m, 1H), 8.25 (m, 1H), 8.06 (dt, 1H, J=1.2 & 8.0 Hz), 7.63 (t, 1H, J=7.6 Hz), 3.96 (s, 3H), 2.69 (s, 3H). Mass [M+H]+: 230.1

45. Preparation of 3-(pyrrolidin-1-ylsulfonyl)benzohydrazide

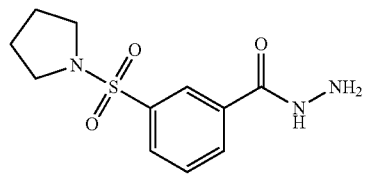 [SMILES: NNC(=O)c1cccc(S(=O)(=O)N2CCCC2)c1]

Methyl 3-(pyrrolidin-1-ylsulfonyl)benzoate (150 mg, 0.557 mmol) was added to the hydrazine (35.7 mg, 1.114 mmol) in methanol and refluxed for 12 h at 65° C. Following cooling, reaction was monitored by TLC. After completion of the reaction, the solvent was removed by vacuum and then compound was purified by column chromatography to yield 3-(pyrrolidin-1-ylsulfonyl)benzohydrazide (110 mg, 0.396 mmol, 71.1% yield). 1H NMR (CDCl3, 400 MHz): δ 8.18 (m, 1H), 8.03 (d, 1H, J=7.6 Hz), 7.97 (d, 1H, J=8.0 Hz), 7.78 (bs, 1H), 7.63 (t, 1H, J=7.6 Hz), 4.17 (bs, 2H), 3.25 (m, 4H), 1.77 (m, 4H). Mass [M+H]+: 270.1

46. Preparation of 3-(hydrazinecarbonyl)-N-methylbenzenesulfonamide

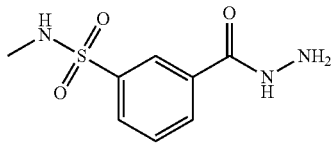

Hydrazine (43.3 mg, 1.352 mmol) was added to the methyl 3-(N-methylsulfamoyl)benzoate (155 mg, 0.676 mmol) in methanol and refluxed for 12 h at 65° C. Following cooling, reaction was monitored by TLC. After completion of the reaction, the solvent was removed by vacuum and then compound was purified by column chromatography to yield 3-(hydrazinecarbonyl)-N-methylbenzenesulfonamide (120 mg, 0.502 mmol, 74.3% yield). 1H NMR (CDCl3, 400 MHz): δ 8.25 (m, 1H), 8.01 (m, 2H), 7.64 (m, 2H), 4.63 (m, 1H), 4.17 (m, 2H), 2.69 (d, 3H, J=5.2 Hz). ESI-MS: 230.0 [M+H]+

47. Preparation of (E)-N'-(1-(5-chloro-2-hydroxyphenyl)ethylidene)-2-(morpholinosulfonyl)benzohydrazide

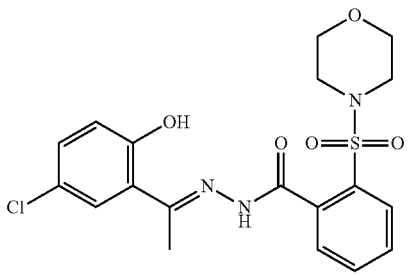 [SMILES: C/C(=N\NC(=O)c1ccccc1S(=O)(=O)N1CCOCC1)c1cc(Cl)ccc1O]

2-(morpholinosulfonyl)benzohydrazide (30 mg, 0.105 mmol) and 1-(5-chloro-2-hydroxyphenyl)ethanone (17.94 mg, 0.105 mmol) was dissolved in Methanol (Volume: 4 ml) in the presence of acetic acid as a catalyst and then the reaction mixture was heated via microwave irradiation to 120° C. for 30 min. Reaction was monitored by TLC. After completion of the reaction, following cooling, the solvent was removed by vacuum and the resulting crude material was purified by flash column chromatography (2% CH3OH/CH2Cl2) afforded the title compound (E)-N'-(1-(5-chloro-2-hydroxyphenyl)ethylidene)-2-(morpholinosulfonyl)benzohydrazide (10 mg, 0.022 mmol, 21.28% yield) as a solid. 1H NMR (CD3OD, 400 MHz): δ 7.95 (d, 1H, J=8.0 Hz), 7.95-7.70 (m, 2H), 7.66 (d, 1H, J=7.6 Hz), 7.56 (d, 1H, J=2.8 Hz), 7.25 (dd, 1H, J=2.8 & 8.8 Hz), 6.91 (d, 1H, J=8.4 Hz), 3.66 (m, 4H), 3.2 (m, 4H), 2.36 (s, 3H). Mass [M+H]+: 438.1

48. Preparation of (E)-3-(2-(1-(5-chloro-2-hydroxyphenyl)ethylidene)hydrazinecarbonyl)-N-methylbenzenesulfonamide

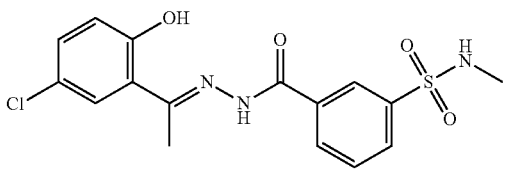 [SMILES: CNS(=O)(=O)c1cccc(C(=O)N/N=C(\C)c2cc(Cl)ccc2O)c1]

3-(hydrazinecarbonyl)-N-methylbenzenesulfonamide (120 mg, 0.523 mmol) and 1-(5-chloro-2-hydroxyphenyl)ethanone (89 mg, 0.523 mmol) was dissolved in Methanol (Volume: 4 ml) in the presence of acetic acid as a catalyst and then the reaction mixture was heated via microwave irradiation to 120° C. for 30 min. Reaction was monitored by TLC. After completion of the reaction, following cooling, the solvent was removed by vacuum and the resulting crude material was purified by flash column chromatography (2% CH3OH/CH2Cl2) afforded the title compound (E)-3-(2-(1-(5-chloro-2-hydroxyphenyl)ethylidene)hydrazinecarbonyl)-N-methylbenzenesulfonamide (75 mg, 0.192 mmol, 36.8% yield) as a solid. 1H NMR (CDCl3, 400 MHz): δ 8.21 (m, 1H), 8.06 (m, 1H), 7.95 (d, 1H, J=7.6 Hz), 7.59 (t, 1H, J=8.0 Hz), 7.39 (d, 1H, J=2.4 Hz), 7.18 (m, 1H), 6.90 (d, 1H, J=8.0 Hz), 2.56 (s, 3H), 2.36 (5, 3H). Mass [M+H]+: 382.1

49. Preparation of (E)-N'-(1-(5-chloro-2-hydroxyphenyl)ethylidene)-3-(pyrrolidin-1-ylsulfonyl)benzohydrazide

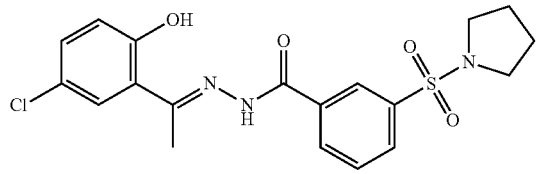 [SMILES: C/C(=N\NC(=O)c1cccc(S(=O)(=O)N2CCCC2)c1)c1cc(Cl)ccc1O]

3-(pyrrolidin-1-ylsulfonyl)benzohydrazide (105 mg, 0.390 mmol) and 1-(5-chloro-2-hydroxyphenyl)ethanone (66.5 mg, 0.390 mmol) was dissolved in Methanol (Volume: 4 ml) in the presence of acetic acid as a catalyst and then the reaction mixture was heated via microwave irradiation to 120° C. for 30 min. Reaction was monitored by TLC. After completion of the reaction, following cooling, the solvent was removed by vacuum and the resulting crude material was purified by flash column chromatography (2% CH$_3$OH/CH$_2$Cl$_2$) afforded the title compound (E)-N'-(1-(5-chloro-2-hydroxyphenyl)ethylidene)-3-(pyrrolidin-1-ylsulfonyl)benzohydrazide (70 mg, 0.163 mmol, 41.7% yield) as a solid. 1H NMR (CDCl3, 400 MHz): δ 8.18 (m, 1H), 8.13 (m, 1H), 7.95 (d, 1H, J=7.6 Hz), 7.65 (t, 1H, J=7.6 Hz), 7.41 (m, 1H), 7.21 (m, 1H), 6.93 (d, 1H, J=8.8 Hz), 3.23 (m, 4H), 2.39 (s, 3H), 1.75 (m, 4H). Mass [M+H]+: 422.1

50. Preparation of methyl 3-(1,1-dioxidothiomorpholino)benzoate

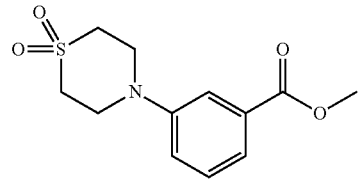 [SMILES: COC(=O)c1cccc(N2CCS(=O)(=O)CC2)c1]

3-(1,1-dioxidothiomorpholino)benzoic acid (100 mg, 0.392 mmol) was refluxed in the presence of con. Sulfuric acid (2.53 mg, 0.020 mmol) in methanol (5 mL) at 70° C. for overnight. Reaction was monitored by TLC. After completion of the reaction, the solvent was removed by vacuum and then compound was purified by flash chromatography afforded the methyl 3-(1,1-dioxidothiomorpholino)benzoate (99 mg, 0.353 mmol, 90% yield). 1H NMR (CDCl3, 400 MHz): δ 7.58 (m, 2H), 7.36 (t, 1H, J=8.0 Hz), 7.09 (m, 1H), 3.91 (s, 3H), 3.89 (m, 4H), 3.11 (m, 4H). Mass [M+H]+: 270.1

51. Preparation of 3-(1,1-dioxidothiomorpholino)benzohydrazide

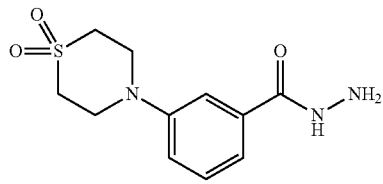 [SMILES: NNC(=O)c1cccc(N2CCS(=O)(=O)CC2)c1]

Methyl 3-(1,1-dioxidothiomorpholino)benzoate (95 mg, 0.353 mmol) was added to the hydrazine (22.61 mg, 0.705 mmol) in methanol and refluxed for 12 h at 65° C. Following cooling, Reaction was monitored by TLC. After completion of the reaction, the solvent was removed by vacuum and then compound was purified by column chromatography (2% CH3OH/CH2Cl2) afforded the title compound 3-(1,1-dioxidothiomorpholino)benzohydrazide (32 mg, 0.109 mmol, 31.0% yield) as a solid. 1H NMR (CDCl3, 400 MHz): δ 7.34 (m, 1H), 7.29 (t, 1H, J=8.4 Hz), 7.18 (d, 1H, J=7.6 Hz), 6.70 (dd, 1H, J=4.8 & 8.0 Hz), 3.85 (m, 4H), 3.05 (m, 4H). Mass [M+H]+: 270.1

52. Preparation of (E)-N'-(1-(5-chloro-2-hydroxyphenyl)ethylidene)-3-(1,1-dioxidothiomorpholino)benzohydrazide

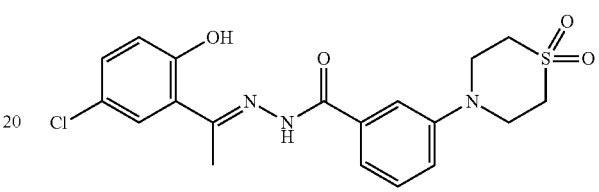

3-(1,1-dioxidothiomorpholino)benzohydrazide (30 mg, 0.111 mmol) and 1-(5-chloro-2-hydroxyphenyl)ethanone (19.00 mg, 0.111 mmol) was dissolved in methanol (Volume: 4 ml) in the presence of acetic acid as a catalyst and then the reaction mixture was heated via microwave irradiation to 120° C. for 30 min. Reaction was monitored by TLC. After completion of the reaction, following cooling, the solvent was removed by vacuum and the resulting crude material was purified by flash column chromatography (2% CH$_3$OH/CH$_2$Cl$_2$) afforded the title compound (E)-N'-(1-(5-chloro-2-hydroxyphenyl)ethylidene)-3-(1,1-dioxidothiomorpholino)benzohydrazide (15 mg, 0.035 mmol, 31.3% yield) as a solid. 1H NMR (DMSO-d6, 400 MHz): δ 7.65 (d, 1H, J=2.0 Hz), 7.47 (m, 1H), 7.41 (t, 1H, J=7.6 Hz), 7.36-7.27 (m, 3H), 6.94 (d, 1H, J=8.8 Hz), 3.87 (m, 4H), 3.17 (m, 4H), 2.48 (s, 3H). Mass [M+H]+: 422.2

53. Preparation of (E)-N'-(1-(5-chloro-2-nitrophenyl)ethylidene)-3-(morpholinosulfonyl)benzohydrazide

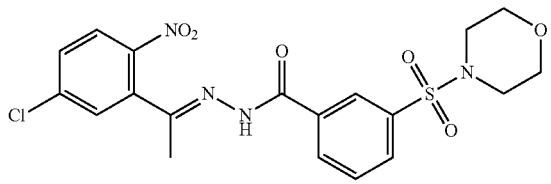

1-(5-chloro-2-nitrophenyl)ethanone (30 mg, 0.150 mmol) and 3-(morpholinosulfonyl)benzohydrazide (42.9 mg, 0.150 mmol) was dissolved in Methanol (Volume: 4 ml) in the presence of acetic acid as a catalyst and then the reaction mixture was heated via microwave irradiation to 120° C. for 30 min. Reaction was monitored by TLC. After completion of the reaction, following cooling, the solvent was removed by vacuum and the resulting crude material was purified by flash column chromatography (2% CH$_3$OH/CH$_2$Cl$_2$), afforded the product (E)-N'-(1-(5-chloro-2-nitrophenyl)ethylidene)-3-(morpholinosulfonyl)benzohydrazide (15 mg, 0.030 mmol, 20.09% yield) as a solid. 1H NMR (CDCl3, 400 MHz): δ 8.20

(m, 1H), 8.07 (m, 1H), 7.88 (m, 1H), 7.66 (m, 1H), 7.51 (m, 2H), 7.39 (m, 1H), 3.69 (m, 4H), 2.99 (m, 4H), 2.29 (s, 3H). Mass [M+H]+: 468.0

54. Preparation of methyl 3-sulfamoylbenzoate

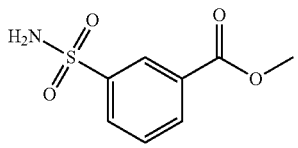

3-sulfamoylbenzoic acid (150 mg, 0.746 mmol) was refluxed in the presence of concentrated Sulfuric acid (4.82 mg, 0.037 mmol) in methanol (5 mL) at 70° C. for overnight. Reaction was monitored by TLC. After completion of the reaction, Solvent was removed by vacuum and then compound was purified by flash chromatography afforded the methyl 3-sulfamoylbenzoate (115 mg, 0.524 mmol, 70.2% yield) as a solid. 1H NMR (CDCl3, 400 MHz): δ 8.53 (m, 1H), 8.18 (d, 1H, J=8.0 Hz), 8.08 (d, 1H, J=7.6 Hz), 7.57 (t, 1H, J=8.0 Hz), 3.92 (s, 3H). Mass [M+H]+: 216.0

55. Preparation of methyl 4-(morpholinosulfonyl)benzoate

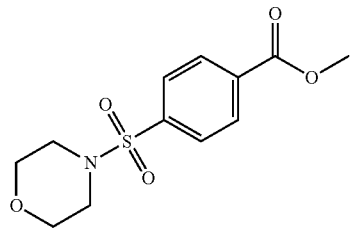 [SMILES: COC(=O)c1ccc(S(=O)(=O)N2CCOCC2)cc1]

4-(morpholinosulfonyl)benzoic acid (150 mg, 0.553 mmol) was refluxed in the presence of con. Sulfuric acid (3.57 mg, 0.028 mmol) in methanol at 70° C. for overnight. Reaction was monitored by TLC. After completion of the reaction, solvent was removed by vacuum and then compound was purified by flash chromatography afforded the methyl 4-(morpholinosulfonyl)benzoate (135 mg, 0.464 mmol, 84% yield). 1H NMR (CDCl3, 400 MHz): δ 8.21 (m, 2H), 7.82 (m, 2H), 3.97 (s, 3H), 3.4 (m, 4H), 3.02 (m, 4H). Mass [M+H]+: 286.0

56. Preparation of 3-(hydrazinecarbonyl)benzenesulfonamide

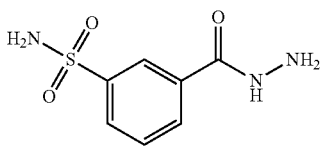 [SMILES: NNC(=O)c1cccc(S(N)(=O)=O)c1]

Methyl 3-sulfamoylbenzoate (110 mg, 0.511 mmol) was added to the hydrazine (32.8 mg, 1.022 mmol) in methanol and refluxed for 8 h at 65° G. Following cooling, reaction was monitored by TLC. After completion of the reaction, the solvent was removed by vacuum and then compound was purified by flash chromatography (5% methanol/DCM) to yield the 3-(hydrazinecarbonyl)benzenesulfonamide (57 mg, 0.260 mmol, 50.8% yield) as a white solid. 1H NMR (CD3OD, 400 MHz): δ 8.32 (m, 1H), 8.04 (d, 1H, J=7.6 Hz), 7.97 (d, 1H, J=7.6 Hz), 7.63 (t, 1H, J=8.0 Hz). Mass [M+H]+: 216.0

57. Preparation of 4-(morpholinosulfonyl)benzohydrazide

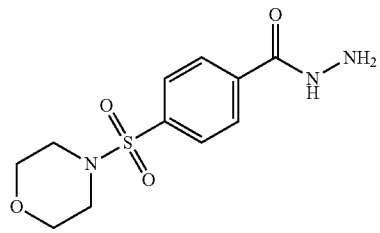 [SMILES: NNC(=O)c1ccc(S(=O)(=O)N2CCOCC2)cc1]

Methyl 4-(morpholinosulfonyl)benzoate (135 mg, 0.473 mmol) was added to the hydrazine (30.3 mg, 0.946 mmol) in methanol and refluxed for 8 h at 65° C. Following cooling, reaction was monitored by TLC. After completion of the reaction, the solvent was removed by vacuum and then compound was purified by flash chromatography (3% methanol/DCM) to yield the 4-(morpholinosulfonyl)benzohydrazide (102 mg, 0.350 mmol, 74.0% yield) as a white solid. 1H NMR (CDCl3, 400 MHz): δ 7.94 (m, 2H), 7.79 (m, 2H), 3.72 (m, 4H), 2.99 (m, 4H). Mass [M+H]+: 286.0

58. Preparation of (E)-3-(2-(1-(5-chloro-2-hydroxyphenyl)ethylidene)hydrazinecarbonyl)benzenesulfonamide

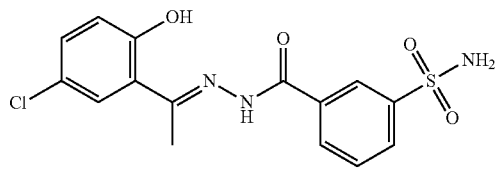 [SMILES: C/C(=N\NC(=O)c1cccc(S(N)(=O)=O)c1)c1cc(Cl)ccc1O]

3-(hydrazinecarbonyl)benzenesulfonamide (50 mg, 0.232 mmol) and 1-(5-chloro-2-hydroxyphenyl)ethanone (39.6 mg, 0.232 mmol) was dissolved in methanol (Volume: 4 ml) in the presence of acetic acid as a catalyst and then the reaction mixture was heated via microwave irradiation to 120° C. for 30 min. Reaction was monitored by TLC. After completion of the reaction, following cooling, the solvent was removed by vacuum and the resulting crude material was purified by flash column chromatography (2% CH3OH/CH2Cl2) afforded the product (E)-3-(2-(1-(5-chloro-2-hydroxyphenyl)ethylidene)hydrazinecarbonyl)benzenesulfonamide (36 mg, 0.094 mmol, 40.4% yield) as a solid. 1H NMR (DMSO-d6, 400 MHz): δ 8.34 (s, 1H), 8.15 (d, 1H, J=7.6 Hz), 8.02 (d, 1H, J=7.6 Hz), 7.73 (t, 1H, J=8.0 Hz), 7.64 (m, 1H), 7.51 (bs, 2H), 7.32 (dd, 1H, J=2.4 & 8.4 Hz), 6.92 (d, 1H, J=8.4 Hz), 2.49 (s, 3H). Mass [M+H]+: 368.0

59. Preparation of (E)-N'-(1-(5-chloro-2-hydroxyphenyl)ethylidene)-4-(morpholinosulfonyl)benzohydrazide

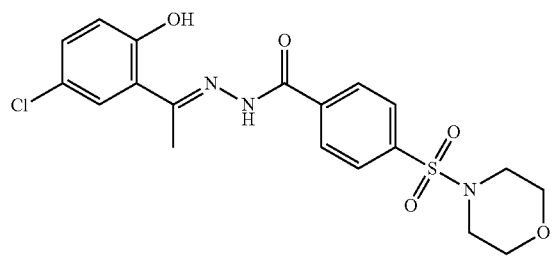 [SMILES: C/C(=N\NC(=O)c1ccc(S(=O)(=O)N2CCOCC2)cc1)c1cc(Cl)ccc1O]

4-(morpholinosulfonyl)benzohydrazide (100 mg, 0.350 mmol) and 1-(5-chloro-2-hydroxyphenyl)ethanone (59.8 mg, 0.350 mmol) was dissolved in methanol (Volume: 4 ml) in the presence of acetic acid as a catalyst and then the reaction mixture was heated via microwave irradiation to 120° C. for 30 min. Reaction was monitored by TLC. After completion of the reaction, following cooling, the solvent was removed by vacuum and the resulting crude material was purified by flash column chromatography (2% $CH_3OH/CH_2Cl_2$) afforded the product (E)-N'-(1-(5-chloro-2-hydroxyphenyl)ethylidene)-4-(morpholinosulfonyl)benzohydrazide (80 mg, 0.177 mmol, 50.6% yield) as a solid. 1H NMR (DMSO-d6, 400 MHz): δ 8.16 (m, 2H), 7.89 (m, 2H), 7.67 (d, 1H, J=2.4 Hz), 7.35 (dd, 1H, J=2.4 & 8.8 Hz), 6.95 (d, 1H, J=8.4 Hz), 3.64 (m, 4H), 2.92 (m, 4H), 2.49 (s, 3H). Mass [M+H]+: 438.0

60. Preparation of 3-((4-methylpiperazin-1-yl)sulfonyl)benzoic acid

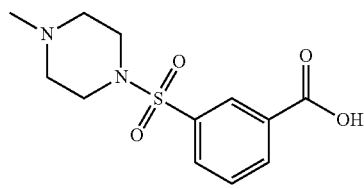 [SMILES: CN1CCN(S(=O)(=O)c2cccc(C(=O)O)c2)CC1]

3-(chlorosulfonyl)benzoic acid (200 mg, 0.906 mmol) was added to the 1-methylpiperazine (100 mg, 0.997 mmol) in presence of potassium carbonate (251 mg, 1.813 mmol) in THF (Volume: 5 ml) at room temperature and the reaction mixture was stirred for 12 h at room temperature. Reaction was monitored by TLC. After completion of the reaction, the solvent was removed by vacuum and then compound was purified by column chromatography (3% $CH_3OH/CH_2Cl_2$) afforded the product 3-((4-methylpiperazin-1-yl)sulfonyl)benzoic acid (100 mg, 0.320 mmol, 35.3% yield) as a solid. 1H NMR (CDCl3, 400 MHz): δ 7.77 (m, 2H), 7.63-7.55 (m, 2H), 3.04 (m, 4H), 2.46 (m 4H), 2.31 (s, 3H). Mass [M+H]+: 285.1

61. Preparation of methyl 3-((4-methylpiperazin-1-yl)sulfonyl)benzoate

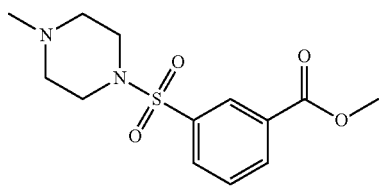

3-((4-methylpiperazin-1-yl)sulfonyl)benzoic acid (250 mg, 0.879 mmol) was refluxed in the presence of concentrated sulfuric acid (5.68 mg, 0.044 mmol) in methanol at 70° C. for overnight. Reaction was monitored by TLC. After completion of the reaction, solvent was removed by vacuum and the crude material was used for further reaction without purification.

62. Preparation of 3-((4-methylpiperazin-1-yl)sulfonyl)benzohydrazide

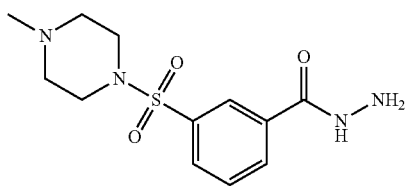 [SMILES: CN1CCN(S(=O)(=O)c2cccc(C(=O)NN)c2)CC1]

Methyl 3-((4-methylpiperazin-1-yl)sulfonyl)benzoate (200 mg, 0.670 mmol) was added to the hydrazine (43.0 mg, 1.341 mmol) in methanol and refluxed for 8 h at 65° C. Following cooling, reaction was monitored by TLC. After completion of the reaction, the solvent was removed by vacuum and then compound was purified by flash chromatography (3% methanol/DCM) to yield the 3-((4-methylpiperazin-1-yl)sulfonyl)benzohydrazide (125 mg, 0.406 mmol, 60.6% yield) as a white solid. 1H NMR (DMSO-d6, 400 MHz): δ 10.08 (s, 1H), 8.12 (m, 2H), 7.84 (d, 1H, J=7.6 Hz), 7.72 (t, 1H, J=7.6 Hz), 4.57 (m, 1H), 2.88 (m, 4H), 2.32 (m, 4H), 2.10 (s, 3H). Mass [M+H]+: 298.9

63. Preparation of (E)-N'-(1-(5-chloro-2-hydroxyphenyl)ethylidene)-3-((4-methylpiperazin-1-yl)sulfonyl)benzohydrazide

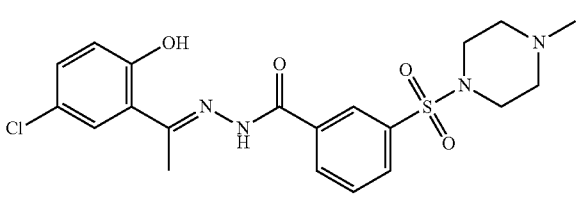

3-((4-methylpiperazin-1-yl)sulfonyl)benzohydrazide (85 mg, 0.285 mmol) and 1-(5-chloro-2-hydroxyphenyl)ethanone (48.6 mg, 0.285 mmol) was dissolved in methanol (Volume: 4 ml) in the presence of acetic acid as a catalyst and then the reaction mixture was heated via microwave irradiation to 120° C. for 30 min. Reaction was monitored by TLC. After completion of the reaction, following cooling, the solvent was removed by vacuum and the resulting crude material was purified by flash column chromatography (2% CH₃OH/CH₂Cl₂) afforded the product (E)-N'-(1-(5-chloro-2-hydroxyphenyl)ethylidene)-3-((4-methylpiperazin-1-yl)sulfonyl)benzohydrazide (70 mg, 0.152 mmol, 53.4% yield) as a solid. 1H NMR (CD3OD, 400 MHz): δ 8.29 (s, 1H), 8.21 (d, 1H, J=7.2 Hz), 7.99 (d, 1H, J=8.0 Hz), 7.78 (t, 1H, J=7.6 Hz), 7.59 (d, 1H, J=2.4 Hz), 7.27 (dd, 1H, J=2.4 & 9.2 Hz), 6.92 (d, 1H, J=8.8 Hz), 3.09 (m, 4H), 2.54 (m, 4H), 2.48 (s, 3H), 2.28 (s, 3H). Mass [M+H]+: 450.9

64. Preparation of 3-(piperidin-1-ylsulfonyl)benzohydrazide

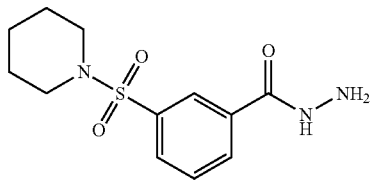 [SMILES: NNC(=O)c1cccc(S(=O)(=O)N2CCCCC2)c1]

Methyl 3-(piperidin-1-ylsulfonyl)benzoate (150 mg, 0.529 mmol) was added to the hydrazine (50.9 mg, 1.588 mmol) in methanol and refluxed for 8 h at 65° C. Following cooling, reaction was monitored by TLC. After completion of the reaction, solvent was removed by vacuum and then compound was purified by flash chromatography (3% methanol/DCM) to yield the 3-(piperidin-1-ylsulfonyl)benzohydrazide (70 mg, 0.245 mmol, 46.2% yield) as a white solid. 1H NMR (CD3OD, 400 MHz): δ 8.17 (t, 1H, J=1.2 Hz), 8.05 (dt, 1H, J=1.2 & 8.0 Hz), 7.90 (dt, 1H, J=1.2 & 8.0 Hz), 7.69 (t, 1H, J=7.6 Hz), 2.99 (m, 4H), 1.62 (m, 4H), 1.43 (m, 2H). Mass [M+H]+: 284.1

65. Preparation of (E)-N'-(1-(5-chloro-2-hydroxyphenyl)ethylidene)-3-(piperidin-1-ylsulfonyl)benzohydrazide

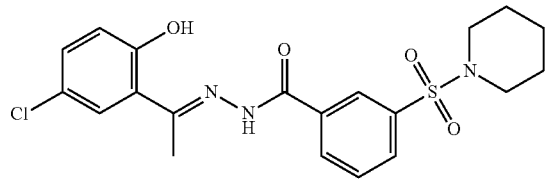 [SMILES: C/C(=N\NC(=O)c1cccc(S(=O)(=O)N2CCCCC2)c1)c1cc(Cl)ccc1O]

3-(piperidin-1-ylsulfonyl)benzohydrazide (65 mg, 0.229 mmol) and 1-(5-chloro-2-hydroxyphenyl)ethanone (39.1 mg, 0.229 mmol) was dissolved in methanol (Volume: 4 ml) in the presence of acetic acid as a catalyst and then the reaction mixture was heated via microwave irradiation to 120° C. for 30 min. Reaction was monitored by TLC. After completion of the reaction, following cooling, the solvent was removed by vacuum and the resulting crude material was purified by flash column chromatography (2% CH₃OH/CH₂Cl₂) afforded the product (E)-N'-(1-(5-chloro-2-hydroxyphenyl)ethylidene)-3-(piperidin-1-ylsulfonyl)benzohydrazide (55 mg, 0.124 mmol, 53.9% yield) as a solid. 1H NMR (CDCl3, 400 MHz): δ 8.09 (m, 2H), 7.85 (d, 1H, J=8.0 Hz), 7.62 (t, 1H, J=8.0 Hz), 7.41 (d, 1H, J=2.4 Hz), 7.22 (d, 1H, J=8.0 Hz), 6.93 (d, 1H, J=8.8 Hz), 2.97 (m, 4H), 2.41 (s, 3H), 1.61 (m, 4H), 1.40 (m, 2H). Mass [M+H]+: 436.9

66. Preparation of 4-chloro-2-(4-methyl-1H-pyrazol-5-yl)phenol

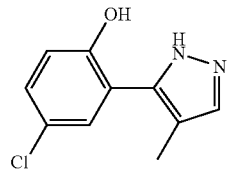

A mixture of (E)-3-(5-chloro-2-hydroxyphenyl)-2-methylacrylaldehyde (40 mg, 0.203 mmol) and 4-methylbenzenesulfonohydrazide (41.7 mg, 0.224 mmol) in Acetonitrile (3 mL) were stirred at room temperature for 3 h and then acetonitrile (2 mL), Sodiumhydroxide (8.95 mg, 0.224 mmol) were added and the mixture was heated at reflux for 16 h. Product was used for further reaction without purification.

67. Preparation of 3-(morpholinosulfonyl)benzoic acid

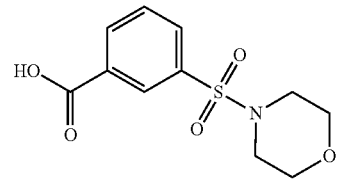 [SMILES: O=C(O)c1cccc(S(=O)(=O)N2CCOCC2)c1]

3-(chlorosulfonyl)benzoic acid (250 mg, 1.133 mmol) was added to the morpholine (99 mg, 1.133 mmol) in presence of Potassiumcarbonate (313 mg, 2.266 mmol) in THF (Volume: 5 ml) at room temperature and reaction mixture allowed to stirred for 12 h at room temperature. Reaction was monitored by TLC. After completion of the reaction, Solvent was removed by vacuum and then compound was purified by column chromatography (3% CH₃OH/CH₂Cl₂) afforded the title compound (160 mg) as a solid. ¹H NMR (400 MHz, CD₃OD): δ 8.34 (m, 1H), 8.32 (d, 1H, J=8.0 Hz), 7.99 (m, 1H), 7.76 (t, 1H, J=8.0 Hz), 3.70 (m, 4H), 2.98 (m, 4H). ESI-MS: 272.0 [M+H]⁺

68. Preparation of (3-(5-chloro-2-hydroxyphenyl)-4-methyl-1H-pyrazol-1-yl)(3-(morpholinosulfonyl)phenyl)methanone

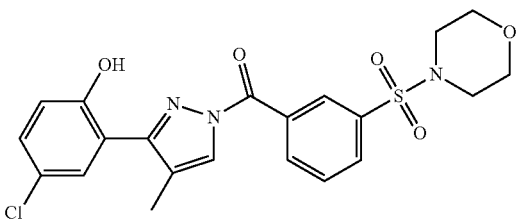 [SMILES: Cc1cn(C(=O)c2cccc(S(=O)(=O)N3CCOCC3)c2)nc1-c1cc(Cl)ccc1O]

A mixture of (E)-3-(5-chloro-2-hydroxyphenyl)-2-methylacrylaldehyde (40 mg, 0.203 mmol) and 4-methylbenzenesulfonohydrazide (41.7 mg, 0.224 mmol) in Acetonitrile (3 mL) were stirred at room temperature for 3 h and then acetonitrile (2 mL), Sodiumhydroxide (8.95 mg, 0.224 mmol) were added and the mixture was heated at reflux for 16 h, then Sodiumhydroxide (12.21 mg, 0.305 mmol) and 3-(morpholinosulfonyl)benzoyl chloride (88 mg, 0.305 mmol) (made from 3-(morpholinosufonyl)benzoic acid) were subsequently added and the mixture was stirred at room temperature for 2 h. Reaction was monitored by TLC. After completion of the reaction, the product was extracted with EtOAc and the organic layer was washed with brine, dried over anhydrous Na2SO4, filtered, and solvent was removed by vacuum. The resulting crude material was purified by flash column chromatography (2% CH₃OH/CH₂Cl₂) afforded the desired product (3-(5-chloro-2-hydroxyphenyl)-4-methyl-1H-pyrazol-1-yl)(3-(morpholinosulfonyl)phenyl)methanone (30 mg, 0.064 mmol, 31.3% yield) as a solid. 1HNMR (400 MHz, CDCl3): δ 8.28 (m, 2H), 8.20 (d, 1H, J=8.0 Hz), 7.95 (d, 1H, J=8.4 Hz), 7.70 (t, 1H, J=7.6 Hz), 7.59 (d, 1H, J=2.4 Hz), 7.18 (dd, 1H, J=2.8 & 8.8 Hz), 6.87 (d, 1H, J=8.4 Hz), 3.68 (m, 4H), 3.02 (m, 4H), 2.40 (s, 3H). ESI-MS: 462.0 [M+H]+

69. Preparation of 4-chloro-2-(1H-pyrazol-3-yl)phenol

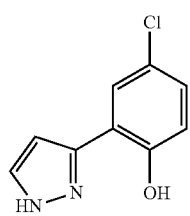 [SMILES: Oc1ccc(Cl)cc1-c1cc[nH]n1]

A mixture of (E)-3-(5-chloro-2-hydroxyphenyl)-2-methylacrylaldehyde (40 mg, 0.203 mmol) and 4-methylbenzenesulfonohydrazide (41.7 mg, 0.224 mmol) in Acetonitrile (3 mL) were stirred at room temperature for 3 h and then acetonitrile (2 mL), Sodiumhydroxide (8.95 mg, 0.224 mmol) were added and the mixture was heated at reflux for 16 h. Product was used for further reaction without purification.

70. Preparation of (3-(5-chloro-2-hydroxyphenyl)-1H-pyrazol-1-yl)(3-(morpholinosulfonyl)phenyl)methanone

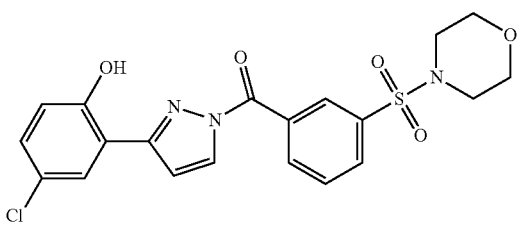

3-(morpholinosulfonyl)benzoic acid (50 mg, 0.184 mmol), 1H-benzo[d][1,2,3]triazol-1-ol (37.4 mg, 0.276 mmol), EDC (53.0 mg, 0.276 mmol) and Sodiumbicarbonate (17.03 mg, 0.203 mmol) was dissolved in THF (10 mL) and then 4-chloro-2-(1H-pyrazol-3-yl)phenol (35.9 mg, 0.184 mmol) was added at room temperature and reaction mixture was allowed to stirred for overnight at room temperature. Reaction was monitored by TLC. After completion of the reaction, the solvent was removed by vacuum and the resulting crude material was purified by flash column chromatography (2% CH₃OH/CH₂Cl₂) afforded the title compound (3-(5-chloro-2-hydroxyphenyl)-1H-pyrazol-1-yl)(3-(morpholinosulfonyl)phenyl)methanone (43 mg, 0.094 mmol, 51.0% yield) as a solid. 1HNMR (400 MHz, CDCl3): δ 8.68 (s, 1H), 8.39 (d, 1H, J=7.6 Hz), 8.01 (d, 1H, J=7.6 Hz), 7.80 (d, 1H, J=2.4 Hz), 7.70 (t, 1H, J=7.6 Hz), 7.53 (d, 1H, J=2.4 Hz), 7.38 (dd, 1H, J=2.4 & 8.4 Hz), 7.27 (d, 1H, J=8.4 Hz), 6.52 (s, 1H), 3.75 (m, 4H), 3.05 (m, 4H). ESI-MS: 448.0 [M+H]+

71. Preparation of 5-((4-methylpiperazin-1-yl)sulfonyl)nicotinohydrazide

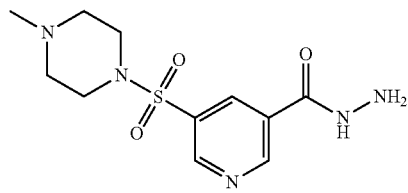 [SMILES: CN1CCN(S(=O)(=O)c2cncc(C(=O)NN)c2)CC1]

Hydrazine (11.78 mg, 0.367 mmol) was added to the methyl 5-((4-methylpiperazin-1-yl)sulfonyl)nicotinate (55 mg, 0.184 mmol) in methanol (10 mL) and refluxed for overnight. The reaction was monitored by TLC, after completion of the reaction, Solvent was removed by vacuum and then compound was purified by column chromatography (3% methanol/DCM) afforded the title compound 5-((4-methylpiperazin-1-yl)sulfonyl)nicotinohydrazide (45 mg, 0.147 mmol, 80% yield) as a solid. 1HNMR (400 MHz, CDCl3): δ 9.07 (s, 1H), 9.02 (s, 1H), 8.33 (s, 1H), 7.46 (bs, 1H), 4.09 (bs, 2H), 3.05 (m, 4H), 2.43 (m, 4H), 2.21 (s, 3H). ESI-MS: 300.1 [M+H]⁺

72. Preparation of (E)-N'-(1-(5-chloro-2-hydroxyphenyl)ethylidene)-5-((4-methylpiperazin-1-yl)sulfonyl)nicotinohydrazide

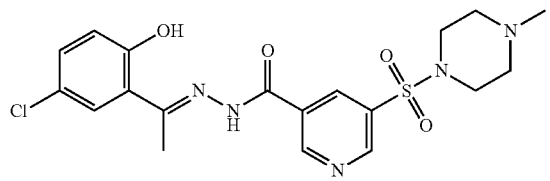 [SMILES: C/C(=N\NC(=O)c1cncc(S(=O)(=O)N2CCN(C)CC2)c1)c1cc(Cl)ccc1O]

1-(5-chloro-2-hydroxyphenyl)ethanone (25.07 mg, 0.147 mmol) and 5-((4-methylpiperazin-1-yl)sulfonyl)nicotinohydrazide (40 mg, 0.134 mmol) was dissolved in Methanol (10 ml) in the presence of acetic acid as a catalyst and then the reaction mixture was refluxed for 12 h at 70° C. Reaction was monitored by TLC. After completion of the reaction, following cooling, the solvent was removed by vacuum and the resulting crude material was purified by flash column chromatography (2% CH₃OH/CH₂Cl₂) afforded the title compound (E)-N'-(1-(5-chloro-2-hydroxyphenyl)ethylidene)-5-((4-methylpiperazin-1-yl)sulfonyl)nicotinohydrazide as a solid. 1HNMR (400 MHz, CDCl3): δ 9.21 (s, 1H), 9.00 (s, 1H), 8.48 (s, 1H), 7.41 (d, 1H, J=2.0 Hz), 7.20 (d, 1H, J=8.4 Hz), 6.90 (d, 1H, J=8.4 Hz), 3.08 (m, 4H), 2.48 (m, 4H), 2.40 (s, 3H), 2.25 (5, 3H). ESI-MS: 452.0 [M+H]+

73. Preparation of methyl 5-(morpholinosulfonyl)nicotinate

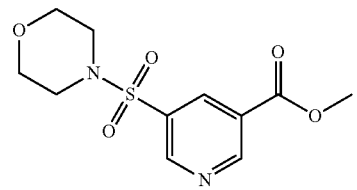 [SMILES: COC(=O)c1cncc(S(=O)(=O)N2CCOCC2)c1]

Methyl 5-(chlorosulfonyl)nicotinate (35 mg, 0.149 mmol) was added to the morpholine (25.9 mg, 0.297 mmol) in presence of Potassiumcarbonate (41.1 mg, 0.297 mmol) in THF (8 mL) at room temperature and the reaction mixture was stirred for 12 h at room temperature. The reaction was monitored by TLC, after completion of the reaction, Solvent was removed by vacuum and then compound was purified by column chromatography (2% Methanol/DCM) afforded the product methyl 5-(morpholinosulfonyl)nicotinate (26 mg, 0.090 mmol, 60.5% yield) as a solid. 1HNMR (400 MHz, CDCl3): δ 9.41 (s, 1H), 9.12 (s, 1H), 8.60 (d, 1H, J=2.0 Hz), 4.01 (s, 3H), 3.76 (m, 4H), 3.07 (m, 4H).

74. Preparation of 5-(morpholinosulfonyl)nicotinohydrazide

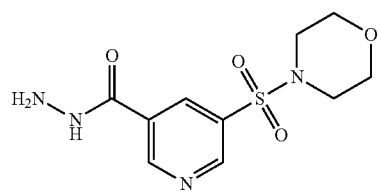 [SMILES: NNC(=O)c1cncc(S(=O)(=O)N2CCOCC2)c1]

AHydrazine (5.60 mg, 0.175 mmol) was added to the methyl 5-(morpholinosulfonyl)nicotinate (25 mg, 0.087 mmol) in methanol (10 mL) and refluxed for overnight. The reaction was monitored by TLC, after completion of the reaction, Solvent was removed by vacuum and then compound was purified by column chromatography (3% methanol/DCM) afforded the title compound 5-(morpholinosulfonyl) nicotinohydrazide as a solid. 1HNMR (400 MHz, CDCl3): δ 9.15 (s, 1H), 8.98 (s, 1H), 8.41 (s, 1H), 3.71 (m, 4H), 3.02 (m, 4H)

75. Preparation of (E)-N'-(1-(5-chloro-2-hydroxyphenyl)ethylidene)-5-(morpholinosulfonyl)nicotinohydrazide

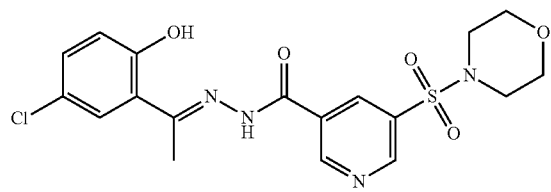 [SMILES: C/C(=N\NC(=O)c1cncc(S(=O)(=O)N2CCOCC2)c1)c1cc(Cl)ccc1O]

1-(5-chloro-2-hydroxyphenyl)ethanone (6.55 mg, 0.038 mmol) and 5-(morpholinosulfonyl)nicotinohydrazide (10 mg, 0.035 mmol) was dissolved in Methanol (3 ml) in the presence of acetic acid as a catalyst and then the reaction mixture was refluxed for 12 h at 70° C. Reaction was monitored by TLC. After completion of the reaction, following cooling, the solvent was removed by vacuum and the resulting crude material was purified by flash column chromatography (2% $CH_3OH/CH_2Cl_2$) afforded the title compound (E)-N'-(1-(5-chloro-2-hydroxyphenyl)ethylidene)-5-(morpholinosulfonyl)nicotinohydrazide (10 mg, 0.023 mmol, 65.2% yield) as a solid. 1HNMR (400 MHz, DMSO-d6): δ 11.82 (bs, 1H), 9.35 (s, 1H), 9.08 (s, 1H), 8.52 (s, 1H), 7.66 (s, 1H), 7.34 (d, 1H, J=8.4 Hz), 6.94 (d, 1H, J=8.8 Hz), 3.63 (m, 4H), 2.99 (m, 4H), 2.50 (s, 3H). ESI-MS: 439.1 [M+H]+

76. General Biochemical and Cell Materials and Methods

LSD1 activity was determined using a LSD1 Inhibitor Screening Assay Kit (Cayman Chemical Item Number 700120) purchased from Cayman Chemical Company (Ann Arbor, Mich.). Recombinant (expressed in baculovirus infected BTI insect cells) monoamine oxidase A and monoamine oxidase B (Catalog No. M7316 and M7441, respectively) were purchased from Sigma-Aldrich Co. LLC. (St. Louis, Mo.). MAO-Glo™ Assay Kit was purchased from Promega Corporation (Madison, Wis.). ATPlite™ Luminescence Assay System (e.g. Catalog No. V1401) was purchased from Perkin Elmer Inc. (Waltham, Mass.).

77. Cell Culture

Cancer cell lines were obtained from ATCC. Cells were cultured according to the procedures provided. Cell-lines used included those shown in Table 4 below. In addition to the supplements indicated in Table 4, media were also supplemented with 1% penicillin/streptomycin (100 IU/mL penicillin and 100 μg/mL streptomycin). Cells were cultured at 37° C. and 5% $CO_2$. ATCC is the American Type Culture Collection (Manassas, Va.).

TABLE 4

| Cell-line | ATCC ® Number | Organ/tissue/pathology* | Culture Media |
| --- | --- | --- | --- |
| AN3 CA | HTB-111 ™ | Uterine/endometrium/ adenocarcinoma | Eagle's Minimum Essential Medium supplemented with 10% FCS** |
| BT-20 | HTB-19 ™ | Breast/carcinoma | Eagle's Minimum Essential Medium supplemented with 10% FCS |
| BT-549 | HTB-122 ™ | Breast/ductal carcinoma | RPMI-1640 Medium supplemented with 0.023 IU/ml insulin and 10% FCS |
| HCT 116 | CCL-247 ™ | Colon/colorectal carcinoma | McCoy's 5a Medium Modified supplemented with 10% FCS |
| HER218*** | Not applicable | Breast/adenocarcinoma | RPM1-1640 Medium supplemented and 10% FCS |

TABLE 4-continued

| Cell-line | ATCC® Number | Organ/tissue/pathology* | Culture Media |
|---|---|---|---|
| MCF7 | HTB-22 ™ | Breast/adenocarcinoma | Eagle's Minimum Essential Medium supplemented with 0.01 mg/ml bovine insulin and 10% FCS. |
| MDA-MB-231 | HTB-26 ™ | Breast/adenocarcinoma | Leibovitz's L-15 Medium supplemented with 10% FCS |
| MDA-MB-435S | HTB-129 ™ | Pleural effusion; likely melanoma | Leibovitz's L-15 Medium supplemented with 0.01 mg/ml bovine insulin, •0.01 mg/ml glutathione, and 10% FCS |
| MDA-MB-468 | HTB-132 ™ | Breast/adenocarcinoma | Leibovitz's L-15 Medium supplemented with 10% FCS |
| PANC-1 | CRL-1469 ™ | Pancreas/duct/epithelioid carcinoma | Dulbecco's Modified Eagle's Medium supplemented with 10% FCS |
| PC-3 | CRL-1435 ™ | Prostate adenocarcinoma | F-12K Medium supplemented with 10% FCS |
| SK-N-MC | HTB-10 ™ | Brain/neuroepithelioma | Eagle's Minimum Essential Medium supplemented with 10% FCS |
| T-47D | HTB-133 ™ | Breast/ductal carcinoma | RPMI-1640 Medium supplemented with 0.2 units/ml bovine insulin and 10% FCS |
| U-87 MG | HTB-14 ™ | Brain/glioblastoma, astrocytoma | Eagle's Minimum Essential Medium supplemented with 10% FCS |

*All organ/tissue sources were of human origin.
**FCS is Fetal Calf Serum
***MCF7 cell-line derivative characterized by non-nuclear estrogen receptor and high levels of HER2 (Massarweh S, et al. (2008) Cancer Research 68: 826-33).

78. LSD1 Histone Demethylase Assay

The primary assay for compound inhibitory activity was the LSD1 Inhibitor Screening Assay Kit (Cayman Chemical Company, Ann Arbor, Mich.; Cayman Chemical Item Number 700120). Briefly, test compounds were diluted to 20× the desired test concentration in 100% DMSO and 2.5 µL of the diluted drug sample was added to a black 384-well plate. The LSD1 enzyme stock was diluted 17-fold with assay buffer and 40 µM of the diluted LSD1 enzyme was added to the appropriate wells. The reaction mixture comprised horseradish peroxidase, dimethyl K4 peptide (corresponding to the first 21 amino acids of the N-terminal tail of histone H3), and 10-acetyl-3,7-dihydroxyphenoxazine was then added to wells. Generation of resorufin (generated by reacting with $H_2O_2$ produced in the reaction) was analyzed on an Envision microplate reader with an excitation wavelength of 530 nm and an emission wavelength of 595 nm.

79. Monoamine Oxidase ("MAO") Assay

Inhibition of monoamine oxidase activity was carried used using the MAO-Glo™ Assay Kit according to the manufacturer's suggested protocol. Briefly, 6.25 µL of test compound was added to each well of a 384-well plate. Enzyme (either MAO A or B) was added (12.5 µL in 2× buffer containing 1 µg protein) and allowed to incubate for 5 minutes. Finally, 6.25 µL of 4×MAO substrate was added to each well. Following a one hour incubation, 25 µL of Luciferin detection reagent was added to each well, and incubated for 20 minutes. Luminescence was then measured on an Envision microplate reader.

Representative data used to determine $IC_{50}$ for inhibition of each MAO isoform is provided in FIG. 4, and representative data for several compounds is summarized in Table 8 below.

80. Cell Viability Assay

Cell viability was determined using ATPlite™ Luminescence Assay System (PerkinElmer Inc., Waltham, Mass.) using the various cell-lines described above and in Table 4. Briefly, cells were seeded in 96-well plates and then treated with different concentrations of inhibitor (0.1% final DMSO concentration). After 96-hours of incubation, ATPlite detection reagent was added directly to the culture well. Luminescence was read 5 minutes later on an Envision microplate reader. Representative $IC_{50}$ data for inhibition of cell growth with various cell-lines is provided below in Tables 6, 7, and 9.

81. Real-Time PCR

Briefly, T-47D cells were seeded in 96-well plates and treated with concentrations of inhibitors as indicated. Cell lysates, Reverse transcription, and single color syber green realtime PCR was performed using the Cells-to-Ct kit (Life Technologies). Transcript levels of heme oxygenase (HMOX) were normalized to hypoxanthine phosphoribosyltransferase (HPRT) and β-actin. The primers used in real-time PCR are shown below in Table 5, and representative data for the effect of disclosed compounds on HMOX expression are provided in Tables 6 and 7.

The ASCII text file "Sequence.txt" created on Dec. 10, 2013, having the size of 2 KB, is incorporated by reference into the specification.

TABLE 5

| Primer Designation | Amplification Target | Sequence |
|---|---|---|
| HMOX_F | Heme oxygenase | AACTTTCAGAAGGGCCAGGT |
| HMOX_R | Heme oxygenase | GTAGACAGGGGCGAAGACTG |
| HPRT_F | Hypoxanthine phosphoribosyltransferase | TGCTGAGGATTTGGAAAGGGTG |
| HPRT_R | Hypoxanthine phosphoribosyltransferase | CCTTGAGCACACAGAGGGCTAC |
| B-Actin_F | β-actin | CTGGAACGGTGAAGGTGACA |
| B-Actin_R | β-actin | AAGGGACTTCCTGTAACAACGCA |

82. $IC_{50}$ Calculation $IC_{50}$ values are determined using GraphPad Prism 5 software. The data were entered as an X-Y plot into the software as percent inhibition for each concentration of the drug. The concentration values of the drug were log transformed and the nonlinear regression was carried out using the "sigmoidal dose-response (variable slope)" option within the GraphPad software to model the data and calculate $IC_{50}$ values. The $IC_{50}$ values reported are the concentration of drug at which 50% inhibition was reached.

83. Compound Activity

The ability of representative disclosed compounds to modulate various biochemical and cellular activities was determined using the assays described above. The results are shown in the tables below. The $IC_{50}$ (µM) for inhibition of either LSD1 activity or cell growth using T-47D cells is shown in Tables 6 and 7. In addition, the effect of representative compounds on heme oxygenase (HMOX) expression is also shown in Tables 6 and 7. The $IC_{50}$ for inhibition of monoamine oxidases A ("MAO A") and B ("MAO B") by representative compounds compared to a control compound, tranylcypromine, is shown in Table 8. The effect of Compound No. 12 (in reference to the compound number used in Table 7, or (E)-N'-(1-(5-chloro-2-hydroxyphenyl)ethylidene)-3-(morpholinosulfonyl)benzohydrazide) on cell growth for various cell-lines in shown in Table 9. If an $IC_{50}$ or other assay result is indicated as "n.d.", it was not determined in the indicated assay.

Compound 12 was used to evaluate sensitivity in a panel of cancer cell lines (Table 9). Cell line sensitivity to compound 12 in this viability assay varied by one log, with $IC_{50}$ values around 300 nM to just under 3 µM. For comparison among the representative compounds, $IC_{50}$ values were determined in T-47D cells (see Tables 6 and 7). With few exceptions, it was observed that T-47D cells were sensitive to test compounds that were active in the LSD1 biochemical assay, and were less sensitive to the compounds which showed less activity in the LSD1 assay.

In order to add an additional level of analysis of LSD1 inhibition in cell culture by these compounds, expression array experiments were performed to evaluate transcriptional changes induced by compound 12 (data not shown). These data indicated that heme oxygenase 1 (HMOX1) was one of the most consistently up-regulated genes across multiple cell lines following treatment with this compound. As HMOX1 is known to be regulated by H3 methylation in the promoter (Krieg, A. J., et al. *Mol Cell Biol* 2010, 30 (1), 344-53), the effect of the test compounds on HMOX1 expression in T-47D cells was determined (see Tables 6 and 7). The data show that the representative compounds which are associated with upregulation of HMOX1 expression are also associated inhibitory activity in the LSD1 assay and the cell viability assay.

LSD1 has a high structural homology of to the monoamine oxidase family of enzymes (17.6% for both monoamine oxidase A and B; MAO A and B, respectively; e.g. see Gooden, D. M., et al. *Bioorg Med Chem Lett* 2008, 18 (10), 3047-51). Selective activity of the representative compounds for LSD1 compared to either MAO A or MAO B, is a desirable property for therapeutic compounds targeting LSD1. The specificity of compound 1 and compound 12 were tested in MAO biochemical assays described herein (see FIG. 3 for representative results which are summarized in Table 8). In this assay, the known MAO inhibitor tranylcypromine exhibited activity against both MAO A and B. In contrast, compound 1 exhibited comparable activity to tranylcypromine against MAO B, but showed no activity against MAO A. However, compound 12 does not exhibit activity against either MAO enzyme (>300 µM). Compounds 18 and 24 were also tested, and exhibited no activity against MAO A or B, and the results are provided in Table 8. These results demonstrate that the representative compounds have specificity for LSD1 with significantly reduced effect on the MAO enzymes. It should be noted that both MAO A and B differ from LSD1 in that the FAD is covalently bound to the enzyme through a thioether linkage with Cys406 and Cys397, respectively (Kearney, E. B., et al. *European Journal of Biochemistry* 1971, (24), 321-327; and Bach, A. W., et al. *Proc Natl Acad Sci USA* 1988, (85), 4934-4938).

TABLE 6
| No. | Structure | LSD1 Activity, IC$_{50}$ (μM) | Cell Growth, IC$_{50}$ (μM) | HMOX expression (fold-induction) |
|---|---|---|---|---|
| 1 | 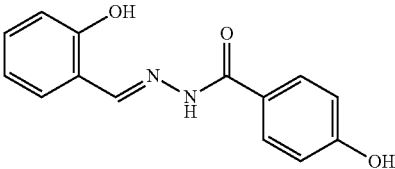 [SMILES: O=C(N/N=C/c1ccccc1O)c1ccc(O)cc1] | 0.218 | 2.7 | 2.3 |
| 2 | 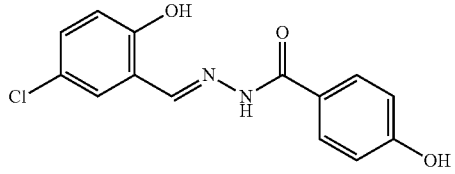 [SMILES: O=C(N/N=C/c1cc(Cl)ccc1O)c1ccc(O)cc1] | 0.275 | 0.821 | 13 |
| 3 | 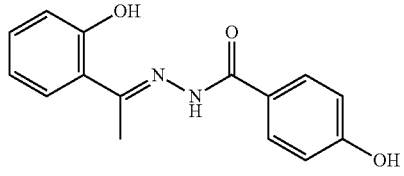 | 0.291 | 0.971 | 15.1 |
| 4 | 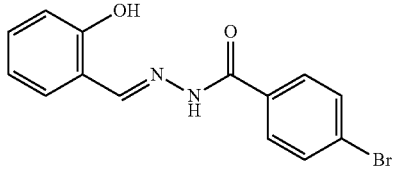 | 0.196 | 0.096 | 20.3 |
| 5 | 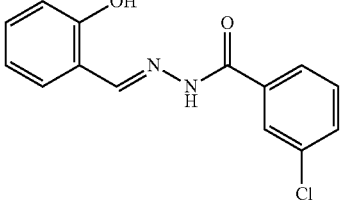 | 0.333 | 0.615 | 31.5 |
| 6 | 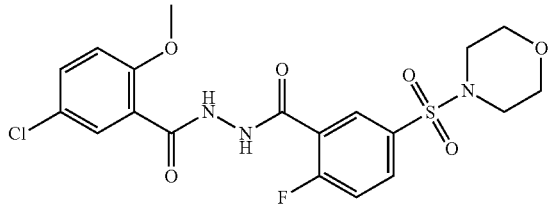 [SMILES: COc1ccc(Cl)cc1C(=O)NNC(=O)c1cc(S(=O)(=O)N2CCOCC2)ccc1F] | >3 | >10 | 1.9 |
| 7 | 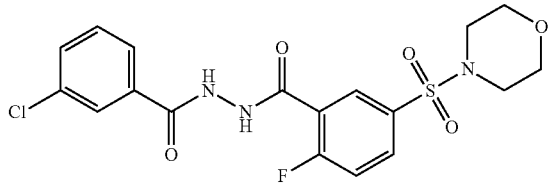 [SMILES: O=C(NNC(=O)c1cc(S(=O)(=O)N2CCOCC2)ccc1F)c1cccc(Cl)c1] | >3 | >10 | 1.1 |

TABLE 6-continued

| No. | Structure | LSD1 Activity, IC$_{50}$ (μM) | Cell Growth, IC$_{50}$ (μM) | HMOX expression (fold-induction) |
|---|---|---|---|---|
| 8 | 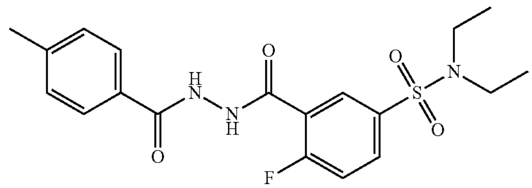 [SMILES: CCN(CC)S(=O)(=O)c1ccc(F)c(C(=O)NNC(=O)c2ccc(C)cc2)c1] | >3 | >10 | 0.9 |
| 9 | 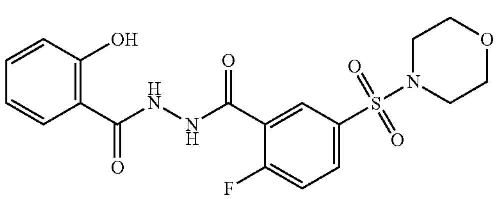 [SMILES: O=C(NNC(=O)c1cc(S(=O)(=O)N2CCOCC2)ccc1F)c1ccccc1O] | 0.013 | 0.524 | 31.7 |
| 10 | 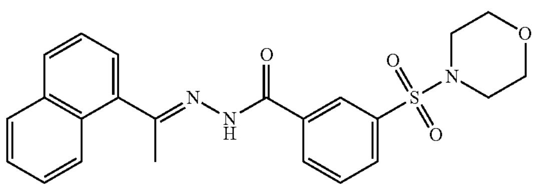 [SMILES: C/C(=N\NC(=O)c1cccc(S(=O)(=O)N2CCOCC2)c1)c1cccc2ccccc12] | >10 | >10 | 1.0 |

TABLE 7

| No. | Structure | LSD1 Activity, IC$_{50}$ (μM) | Cell Growth, IC$_{50}$ (μM) | HMOX expression (fold-induction) |
|---|---|---|---|---|
| 11 | 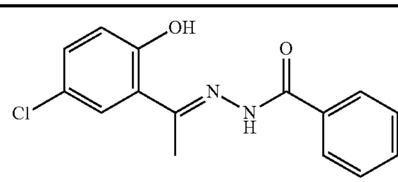 | 0.128 | 0.352 | 31.3 |
| 12 | 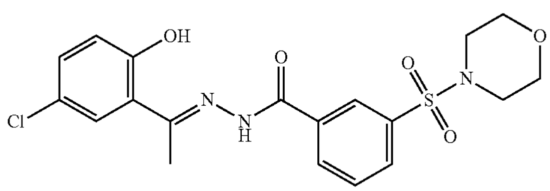 [SMILES: C/C(=N\NC(=O)c1cccc(S(=O)(=O)N2CCOCC2)c1)c1cc(Cl)ccc1O] | 0.013 | 0.649 | 26.9 |
| 13 | 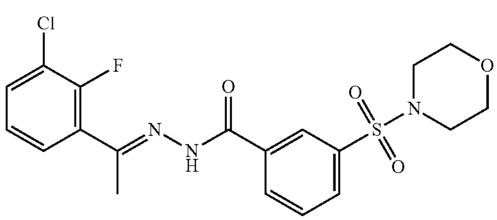 [SMILES: C/C(=N\NC(=O)c1cccc(S(=O)(=O)N2CCOCC2)c1)c1cccc(Cl)c1F] | >3 | >10 | ND |
| 14 | 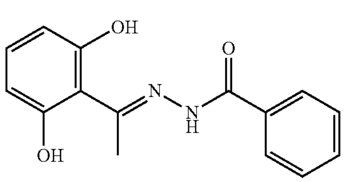 [SMILES: C/C(=N\NC(=O)c1ccccc1)c1c(O)cccc1O] | >3 | >10 | 1.1 |

TABLE 7-continued
| No. | Structure | LSD1 Activity, IC$_{50}$ (μM) | Cell Growth, IC$_{50}$ (μM) | HMOX expression (fold-induction) |
|---|---|---|---|---|
| 15 | 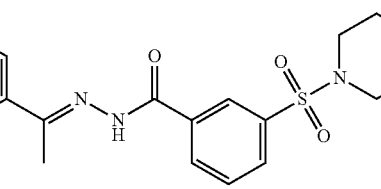 | >3 | >10 | ND |
| 16 | 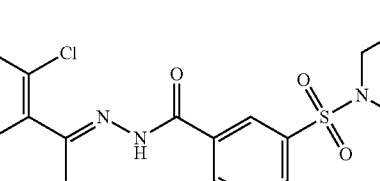 | >3 | >10 | 0.9 |
| 17 | 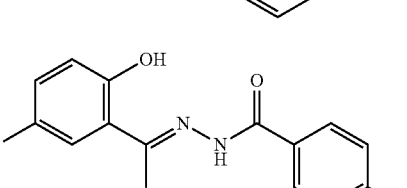 | >3 | 1.700 | ND |
| 18 | 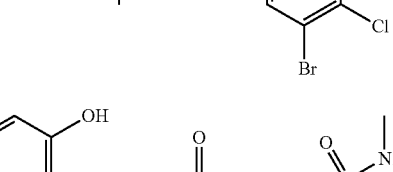 | 0.013 | 0.565 | 56.4 |
| 19 | 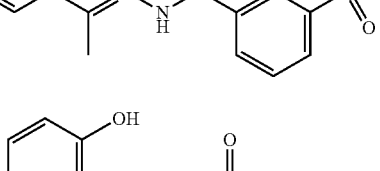 | >3 | 1.375 | ND |
| 20 | 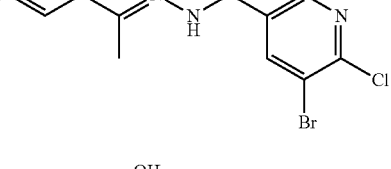 | >3 | 0.270 | ND |
| 21 | 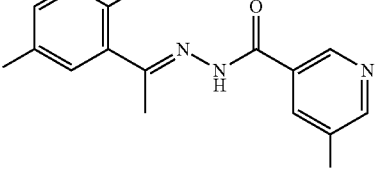 | >3 | 0.616 | ND |

TABLE 7-continued

| No. | Structure | LSD1 Activity, IC$_{50}$ (μM) | Cell Growth, IC$_{50}$ (μM) | HMOX expression (fold-induction) |
|---|---|---|---|---|
| 22 | 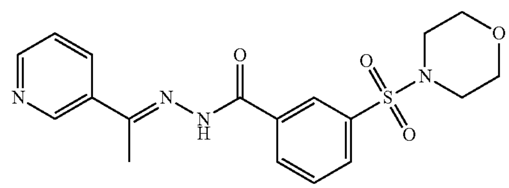 [SMILES: C/C(=N\NC(=O)c1cccc(S(=O)(=O)N2CCOCC2)c1)c1cccnc1] | >3 | ND | ND |
| 23 | 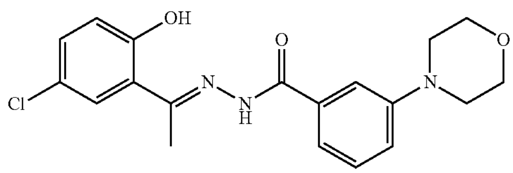 [SMILES: C/C(=N\NC(=O)c1cccc(N2CCOCC2)c1)c1cc(Cl)ccc1O] | 0.519 | ND | ND |
| 24 | 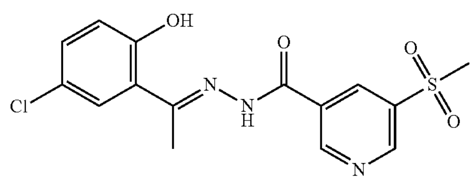 [SMILES: C/C(=N\NC(=O)c1cncc(S(C)(=O)=O)c1)c1cc(Cl)ccc1O] | 0.028 | ND | ND |
| 25 | 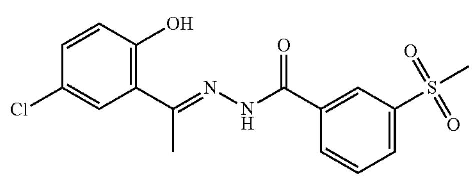 [SMILES: C/C(=N\NC(=O)c1cccc(S(C)(=O)=O)c1)c1cc(Cl)ccc1O] | 0.049 | ND | 50.3 |
| 26 | 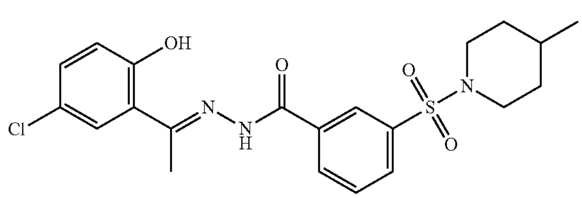 [SMILES: C/C(=N\NC(=O)c1cccc(S(=O)(=O)N2CCC(C)CC2)c1)c1cc(Cl)ccc1O] | 0.0095 | ND | ND |
| 27 | 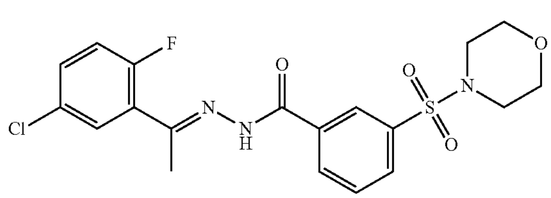 [SMILES: C/C(=N\NC(=O)c1cccc(S(=O)(=O)N2CCOCC2)c1)c1cc(Cl)ccc1F] | >3 | ND | ND |
| 28 | 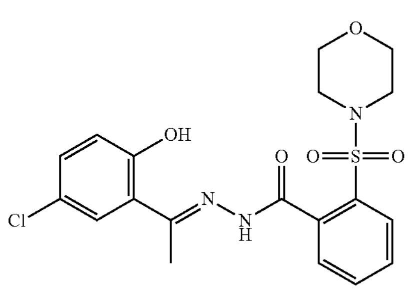 [SMILES: C/C(=N\NC(=O)c1ccccc1S(=O)(=O)N1CCOCC1)c1cc(Cl)ccc1O] | >3 | ND | ND |

TABLE 7-continued

| No. | Structure | LSD1 Activity, IC$_{50}$ (μM) | Cell Growth, IC$_{50}$ (μM) | HMOX expression (fold-induction) |
|---|---|---|---|---|
| 29 | 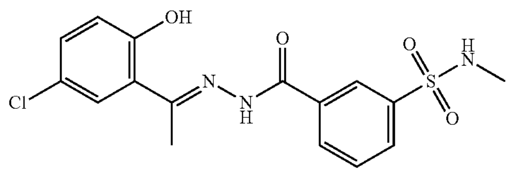 [SMILES: CNS(=O)(=O)c1cccc(C(=O)N/N=C(\C)c2cc(Cl)ccc2O)c1] | 0.0087 | ND | ND |
| 30 | 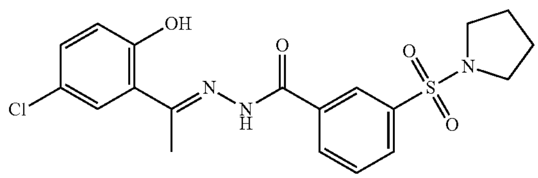 [SMILES: C/C(=N\NC(=O)c1cccc(S(=O)(=O)N2CCCC2)c1)c1cc(Cl)ccc1O] | ND | ND | ND |
| 31 | 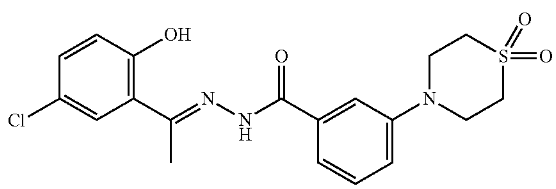 [SMILES: C/C(=N\NC(=O)c1cccc(N2CCS(=O)(=O)CC2)c1)c1cc(Cl)ccc1O] | ND | ND | ND |
| 32 | 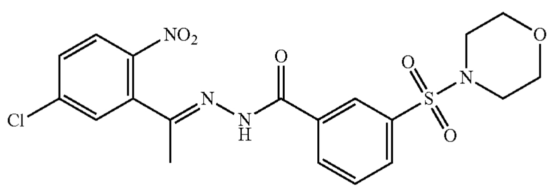 [SMILES: C/C(=N\NC(=O)c1cccc(S(=O)(=O)N2CCOCC2)c1)c1cc(Cl)ccc1[N+](=O)[O-]] | >3 | ND | ND |
| 33 | 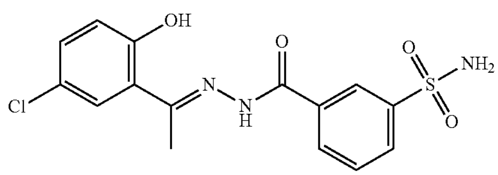 [SMILES: C/C(=N\NC(=O)c1cccc(S(N)(=O)=O)c1)c1cc(Cl)ccc1O] | ND | ND | ND |
| 34 | 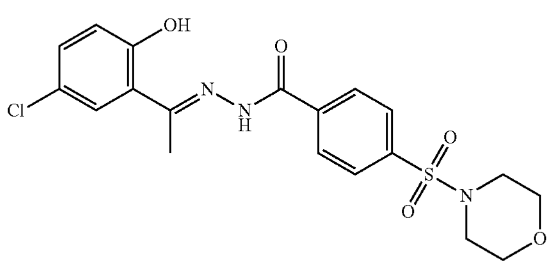 [SMILES: C/C(=N\NC(=O)c1ccc(S(=O)(=O)N2CCOCC2)cc1)c1cc(Cl)ccc1O] | ND | ND | ND |
| 35 | 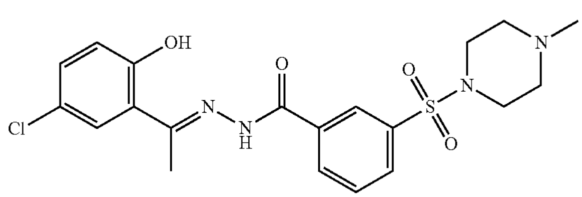 | <0.01 | ND | ND |

TABLE 7-continued

| No. | Structure | LSD1 Activity, IC$_{50}$ (μM) | Cell Growth, IC$_{50}$ (μM) | HMOX expression (fold-induction) |
|---|---|---|---|---|
| 36 | 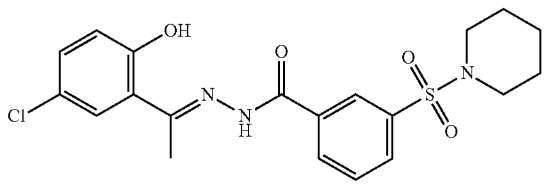 [SMILES: C/C(=N\NC(=O)c1cccc(S(=O)(=O)N2CCCCC2)c1)c1cc(Cl)ccc1O] | ND | ND | ND |
| 37 | 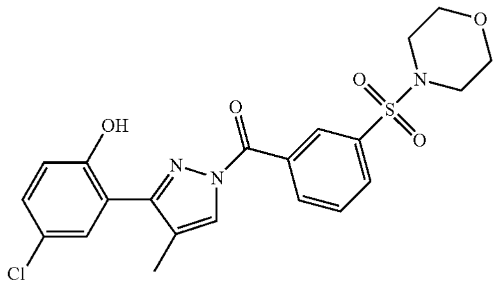 [SMILES: Cc1cn(C(=O)c2cccc(S(=O)(=O)N3CCOCC3)c2)nc1-c1cc(Cl)ccc1O] | >3 | ND | ND |
| 38 | 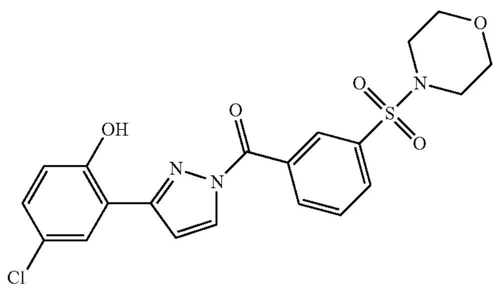 [SMILES: O=C(c1cccc(S(=O)(=O)N2CCOCC2)c1)n1ccc(-c2cc(Cl)ccc2O)n1] | >3 | ND | ND |
| 39 | 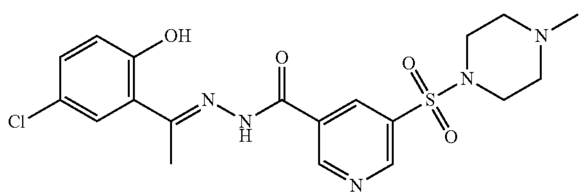 [SMILES: C/C(=N\NC(=O)c1cncc(S(=O)(=O)N2CCN(C)CC2)c1)c1cc(Cl)ccc1O] | ND | ND | ND |
| 40 | 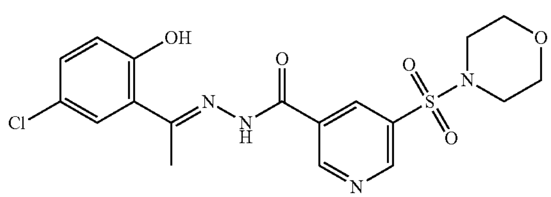 [SMILES: C/C(=N\NC(=O)c1cncc(S(=O)(=O)N2CCOCC2)c1)c1cc(Cl)ccc1O] | ND | ND | ND |

TABLE 8

| No. | Structure | MAO A, IC50 (μM) | MAO B, IC50 (μM) |
|---|---|---|---|
| — | 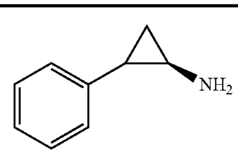 | 2.1 | 3.6 |

TABLE 8-continued

| No. | Structure | MAO A, IC50 (μM) | MAO B, IC50 (μM) |
|---|---|---|---|
| 1 | (2-hydroxyphenyl)methylidene hydrazide of 4-hydroxybenzoic acid | 88.5 | 1.3 |
| 12 | 1-(5-chloro-2-hydroxyphenyl)ethylidene hydrazide of 3-(morpholinosulfonyl)benzoic acid | >300 | >300 |
| 18 | 1-(5-chloro-2-hydroxyphenyl)ethylidene hydrazide of 3-(N,N-dimethylsulfamoyl)benzoic acid | >300 | >300 |
| 24 | 1-(5-chloro-2-hydroxyphenyl)ethylidene hydrazide of 5-(methylsulfonyl)nicotinic acid | >300 | >300 |

TABLE 9

| Cell-line | Cell Growth, IC50 (μM) |
|---|---|
| AN3 Ca | 0.356 |
| BT-20 | 0.489 |
| BT-549 | 1.010 |
| HCT 116 | 0.614 |
| HER218 | 0.612 |
| Hs-578-T | 1.700 |
| HT29 | 0.429 |
| MCF-7 | 0.637 |
| MDA-MB-231 | 1.040 |
| MDA-MB-235 | 0.728 |
| MDA-MB-435 | 1.440 |
| MDA-MB-468 | 2.730 |
| MIA PaCa-2 | 0.468 |
| PANC-1 | 1.104 |
| PC-3 | 2.160 |
| SK-N-MC | 0.329 |
| T-47D | 0.649 |
| U87 | 1.160 |

84. Prophetic In Vivo Anti-Tumor Effects: Cell-Line Xenograft Model

The following examples of the in vivo effect of the disclosed compounds are prophetic. Generally agents which modulate the regulation of chromatin, including histone demethylase inhibitors, display efficacy in preclinical models of cancer. In vivo effects of the compounds described in the preceding examples are expected to be shown in various animal models of cancer known to the skilled person, such as tumor xenograft models. These models are typically conducted in rodent, most often in mouse, but may be conducted in other animal species as is convenient to the study goals. Compounds, products, and compositions disclosed herein are expected to show in vivo effects in various animal models of cancer known to the skilled person, such as mouse tumor xenograft models.

In vivo effects of compounds can be assessed with in a mouse tumor xenograft study, one possible study protocol is described herein. Briefly, cells (2 to 5×10$^6$ in 100 mL culture media) were implanted subcutaneously, e.g. by subcutaneous injection, in the right hind flank of athymic nu/nu nude mice (5 to 6 weeks old, 18-22 g). For test compounds of the present invention, a typical cell-line used for the tumor xenograft study would be AN3 CA or BT-20. Other suitable cell-lines for these studies are BT-549, HCT 116, HER218, MCF7, MDA-MB-231, MDA-MB-235, MDA-MB-435S, MDA-MB-468, PANC-1, PC-3, SK-N-MC, T-47D, and U-87 MG cells. The cells are cultured prior to harvesting for this protocol as described herein.

Following implantation, the tumors are allowed to grow to about 100 mm$^3$, typically about 6-18 days post-implantation, before the animals are randomized into treatment groups (e.g. vehicle, positive control and various dose levels of the test compound); the number of animals per group is typically 8-12. Day 1 of study corresponds to the day that the animals receive their first dose. The efficacy of a test compound can be determined in studies of various lengths dependent upon the goals of the study. Typical study periods are for 14, 21 and 28-days. The dosing frequency (e.g. whether animals are dosed with test compound daily, every other day, every third day or other frequencies) is determined for each study depending upon the toxicity and potency of the test compound. A typical study design would involve dosing daily (M-F) with the test compound with recovery on the weekend. Throughout the study, tumor volumes and body weights are measured twice a week. At the end of the study the animals are euthanized and the tumors harvested and frozen for further analysis. Alternatively, tumors may be processed immediately for analysis, e.g. fixed in buffered-formalin, paraffin embedded, and sectioned for hematoxylin/eosin staining and further immunohistochemical analysis for desired oncology markers.

For example, compounds of the invention, or a pharmaceutically acceptable salt, solvate, polymorph, hydrate and the stereochemically isomeric form thereof, are expected to show such in vivo effects.

85. Prophetic In Vivo Anti-Tumor Effects: Tumor Graft Model

Alternatively, it can be desirable to assess the in vivo efficacy of the disclosed compounds in a tumor explant or tumor graft animal models (e.g. see Rubio-Viqueira B., et al. *Clin Cancer Res.* (2006) 12:4652-4661; Fiebig, H. H., Maier, A. and Burger, A. M. *Eur. J. Canc.* (2004) 40:802-820; and DeRose, Y. S., et al. "Patient-derived tumor grafts authentically reflect tumor pathology, growth, metastasis and disease outcomes." (2011) *Nat. Med.*, in press). These models can provide higher quality information on in vivo effects of therapeutic compounds. It is believed tumor graft models are more authentic in vivo models of many types of cancer, e.g. human breast cancer, with which to examine the biology of tumors and how they metastasize. Engraftment of actual patient tumor tissues into immunodeficient mice (termed 'tumor grafts') provides improvement over implantation of cell lines, in terms of phenocopying human tumors and predicting drug responses in patients (Clarke, R. *Breast Cancer Res* (2009) 11 Suppl 3, S22; Press, J. Z., et al. *Gynecol Oncol* (2008) 110: 56-264; Kim, M. P., et al. *Nat Protoc* (2009) 4:670-1680; Daniel, V. C., et al. *Cancer Res* (2009) 69:3364-3373; and Ding, L., et al. *Nature* (2010) 464:999-1005).

Briefly, tissue samples will be collected from informed, consented patients at Huntsman Cancer Hospital/University of Utah under an approved IRB protocol. Samples will be collected and de☐identified by the Huntsman Cancer Institute Tissue Resource and Application Core facility before being obtained for implantation. It is anticipated that all primary tumors will be from individuals that had not received chemotherapy prior to tissue collection, and all metastatic effusions will be from individuals that had been treated with chemotherapy, hormone therapy, and/or radiation therapy. The University of Utah Institutional Animal Care and Use Committee will review and approve all mouse experiments. It is anticipated that a minimum of three mice per experimental group will be used, and only female mice will be used for studies involving breast cancer tumors. A single fragment of fresh or frozen tumor (~8 mm3), or about $10^6$ cells in matrigel, is implanted into cleared inguinal mammary fat pads of 3-4 week old female NOD/SCID mice. At the same, interscapular estrogen pellets are subcutaneously implanted in mice with ER+ tumors. Tumor growth is measured weekly using calipers. When tumors reach about 150-2,000 mm$^3$, the mice are euthanized, and tissue fragments are re-transplanted into another cohort of mice, frozen for later use, and/or analyzed for histology, gene expression, and DNA copy number. Tumor volumes are calculated using the formula 0.5×length× (width)$^2$. For experiments to determine estrogen dependence, ER+ tumors are implanted into mice as described above, in the presence or absence of intrascapular estrogen pellets and with or without a concurrent surgical procedure to remove the ovaries, which is performed according to standard methods.

Freshly harvested tumor tissues from patients or mice are cut into ~8 mm3 pieces and stored in liquid nitrogen, in a solution of 95% FBS and 5% DMSO for later implantation. Alternatively, the tissue is digested with collagenase solution (1 mg/ml collagenase [Type IV, Sigma] in RPMI 1640 supplemented with 2.5% FBS, 10 mM HEPES, 10 μg/mL penicillin-streptomycin) at 37° C. for 40-60 min, while shaking at 250 rpm. Digested tissue is strained to remove debris and washed in human breast epithelial cell (HBEC) medium (DMEM F/12 supplemented with 10 mM HEPES, 5% FBS, 1 mg/mL BSA, 0.5 μg/mL hydrocortisone, 50 μg mL Gentamycin, 1 μg/mL ITS-X100) three times. The pellet is resuspended in freezing medium (5% FBS and 10% DMSO in HBEC medium) and stored in liquid nitrogen.

To assess the effect of a disclosed compound, tumors in mice are allowed to grow to about 100 mm$^3$, typically about 6-18 days post-implantation, before the animals are randomized into treatment groups (e.g. vehicle, positive control and various dose levels of the test compound); the number of animals per group is typically 8-12. Day 1 of study corresponds to the day that the animals receive their first dose. The efficacy of a test compound can be determined in studies of various lengths dependent upon the goals of the study. Typical study periods are for 14, 21 and 28-days. The dosing frequency (e.g. whether animals are dosed with test compound daily, every other day, every third day or other frequencies) is determined for each study depending upon the toxicity and potency of the test compound. A typical study design would involve dosing daily (M-F) with the test compound with recovery on the weekend. Throughout the study, tumor volumes and body weights are measured twice a week. At the end of the study the animals are euthanized and the tumors harvested and frozen for further analysis. Alternatively, tumors may be processed immediately for analysis, e.g. fixed in buffered-formalin, paraffin embedded, and sectioned for hematoxylin/eosin staining and further immunohistochemical analysis for desired oncology markers.

For example, compounds of the invention, or a pharmaceutically acceptable salt, solvate, polymorph, hydrate and the stereochemically isomeric form thereof, are expected to show such in vivo effects.

86. Prophetic Pharmaceutical Composition Examples

"Active ingredient" as used throughout these examples relates to one or more of the compounds of the invention, or a pharmaceutically acceptable salt, solvate, polymorph, hydrate and the stereochemically isomeric form thereof. The following examples of the formulation of the compounds of the present invention in tablets, suspension, injectables and ointments are prophetic.

Typical examples of recipes for the formulation of the invention are as given below. Various other dosage forms can be applied herein such as a filled gelatin capsule, liquid emulsion/suspension, ointments, suppositories or chewable tablet form employing the disclosed compounds in desired dosage amounts in accordance with the present invention. Various conventional techniques for preparing suitable dosage forms can be used to prepare the prophetic pharmaceutical compositions, such as those disclosed herein and in standard reference texts, for example the British and US Pharmacopoeias, Remington's Pharmaceutical Sciences (Mack Publishing Co.) and Martindale The Extra Pharmacopoeia (London The Pharmaceutical Press).

The disclosure of this reference is hereby incorporated herein by reference.

a. Pharmaceutical Composition for Oral Administration

A tablet can be prepared as follows:

| Component | Amount |
|---|---|
| Active ingredient | 10 to 500 mg |
| Lactose | 100 mg |
| Crystalline cellulose | 60 mg |
| Magnesium stearate | 5 |
| Starch (e.g. potato starch) | Amount necessary to yield total weight indicated below |
| Total (per capsule) | 1000 mg |

Alternatively, about 100 mg of a disclosed compound, 50 mg of lactose (monohydrate), 50 mg of maize starch (native), 10 mg of polyvinylpyrrolidone (PVP 25) (e.g. from BASF, Ludwigshafen, Germany) and 2 mg of magnesium stearate are used per tablet. The mixture of active component, lactose and starch is granulated with a 5% solution (m/m) of the PVP in water. After drying, the granules are mixed with magnesium stearate for 5 min. This mixture is moulded using a customary tablet press (e.g. tablet format: diameter 8 mm, curvature radius 12 mm). The moulding force applied is typically about 15 kN.

Alternatively, a disclosed compound can be administered in a suspension formulated for oral use. For example, about 100-5000 mg of the desired disclosed compound, 1000 mg of ethanol (96%), 400 mg of xanthan gum, and 99 g of water are combined with stirring. A single dose of about 10-500 mg of the desired disclosed compound according can be provided by 10 ml of oral suspension.

In these Examples, active ingredient can be replaced with the same amount of any of the compounds according to the present invention, in particular by the same amount of any of the exemplified compounds. In some circumstances it may be desirable to use a capsule, e.g. a filled gelatin capsule, instead of a tablet form. The choice of tablet or capsule will depend, in part, upon physicochemical characteristics of the particular disclosed compound used.

Examples of alternative useful carriers for making oral preparations are lactose, sucrose, starch, talc, magnesium stearate, crystalline cellulose, methyl cellulose, hydroxypropyl cellulose, hydroxypropylmethyl cellulose, carboxymethyl cellulose, glycerin, sodium alginate, gum arabic, etc. These alternative carriers can be substituted for those given above as required for desired dissolution, absorption, and manufacturing characteristics.

The amount of a disclosed compound per tablet for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

b. Pharmaceutical Composition for Injectable Use

A parenteral composition can be prepared as follows:

| Component | Amount |
|---|---|
| Active ingredient | 10 to 500 mg |
| Sodium carbonate | 560 mg* |
| Sodium hydroxide | 80 mg* |
| Distilled, sterile water | Quantity sufficient to prepare total volume indicated below. |
| Total (per capsule) | 10 ml per ampule |

*Amount adjusted as required to maintain physiological pH in the context of the amount of active ingredient, and form of active ingredient, e.g. a particular salt form of the active ingredient.

Alternatively, a pharmaceutical composition for intravenous injection can be used, with composition comprising about 100-5000 mg of a disclosed compound, 15 g polyethylenglycol 400 and 250 g water in saline with optionally up to about 15% Cremophor EL, and optionally up to 15% ethyl alcohol, and optionally up to 2 equivalents of a pharmaceutically suitable acid such as citric acid or hydrochloric acid are used. The preparation of such an injectable composition can be accomplished as follows: The disclosed compound and the polyethylenglycol 400 are dissolved in the water with stirring. The solution is sterile filtered (pore size 0.22 μm) and filled into heat sterilized infusion bottles under aseptic conditions. The infusion bottles are sealed with rubber seals.

In a further example, a pharmaceutical composition for intravenous injection can be used, with composition comprising about 10-500 mg of a disclosed compound, standard saline solution, optionally with up to 15% by weight of Cremophor EL, and optionally up to 15% by weight of ethyl alcohol, and optionally up to 2 equivalents of a pharmaceutically suitable acid such as citric acid or hydrochloric acid. Preparation can be accomplished as follows: a desired disclosed compound is dissolved in the saline solution with stirring. Optionally Cremophor EL, ethyl alcohol or acid are added. The solution is sterile filtered (pore size 0.22 μm) and filled into heat sterilized infusion bottles under aseptic conditions. The infusion bottles are sealed with rubber seals.

In this Example, active ingredient can be replaced with the same amount of any of the compounds according to the present invention, in particular by the same amount of any of the exemplified compounds.

The amount of a disclosed compound per ampule for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

Carriers suitable for parenteral preparations are, for example, water, physiological saline solution, etc. which can be used with tris(hydroxymethyl)aminomethane, sodium carbonate, sodium hydroxide or the like serving as a solubilizer or pH adjusting agent. The parenteral preparations contain preferably 50 to 1000 mg of a disclosed compound per dosage unit.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula (I)

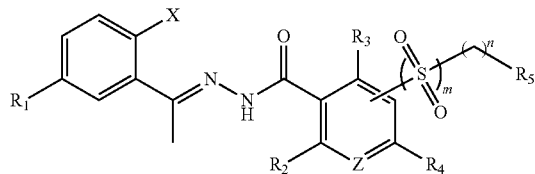

wherein
m is 1;
n is 0;
X is selected from the group consisting of OH, NO$_2$ and F;
Z is selected from the group consisting of N and CH;
R$_1$ is selected from the group consisting of halo, C1-C3 haloalkyl, and C1-C3 polyhaloalkyl;
each of R$_2$, R$_3$, and R$_4$ is independently selected from the group consisting of hydrogen, hydroxyl, cyano, amino, C2-C6 alkalkoxy, C1-C6 alkoxy, C1-C6 alkyl, C1-C6 polyhaloalkyl, and C1-C6 haloalkyl;
R$_5$ is selected from the group consisting of NR$_6$R$_7$, C1-C6 alkyl, C3-C6 cycloalkyl,

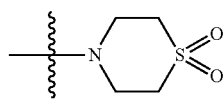

and Cy, and substituted with 0-3 groups independently selected from halo, hydroxyl, amino, C2-C6 alkalkoxy, C1-C6 alkylalcohol, C1-C6 alkoxy, C1-C6 alkyl, C1-06 polyhaloalkyl, C1-C6 haloalkyl, C3-C6 cycloalkyl, and Cy;
Cy is a heterocycloalkyl selected from the group consisting of aziridinyl, azetidinyl, pyrrolidinyl, piperidinyl, azepanyl, oxazolidinyl, imidazolidinyl, pyrazolidinyl, piperazinyl, oxazinanyl, morpholinyl, hexahydrophyrimidinyl, and hexahydropyridazinyl; and
each of R$_6$ and R$_7$ is independently selected from the group consisting of hydrogen, C1-C6 alkyl, C3-C6 cycloalkyl, and C3-C6 heterocycloalkyl;
or a pharmaceutically acceptable salt thereof.

2. A pharmaceutical composition comprising a therapeutically effective amount of a compound of claim 1 and a pharmaceutically acceptable carrier.

3. A compound selected from the group consisting of:

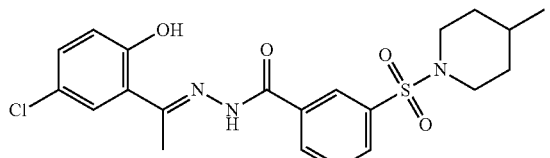

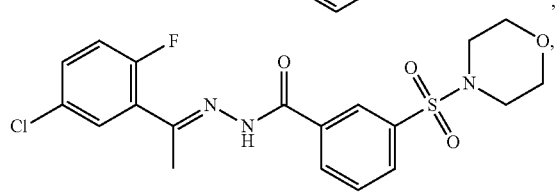

-continued

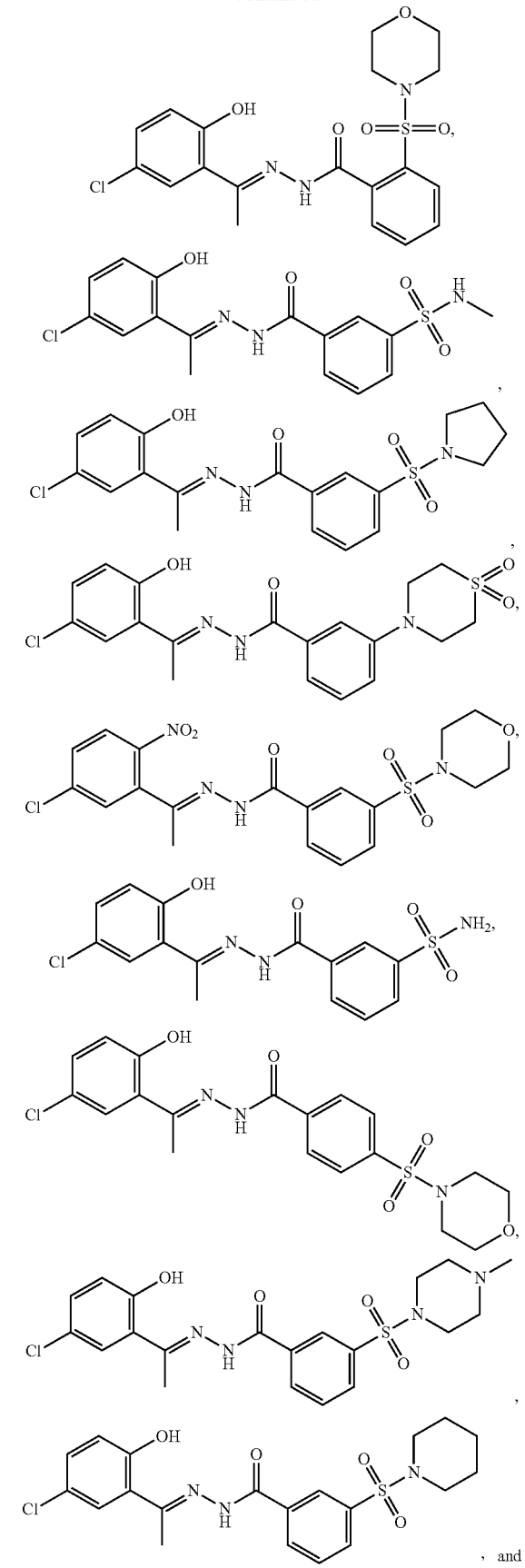

, and

-continued

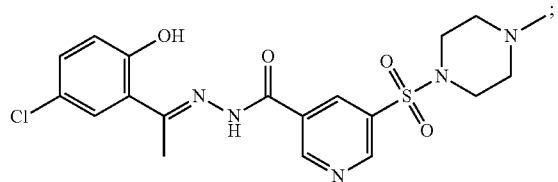

or a pharmaceutically acceptable salt thereof.

4. A pharmaceutical composition comprising a therapeutically effective amount of a compound of claim 3 and a pharmaceutically acceptable carrier.

5. A compound having a structure represented by a formula:

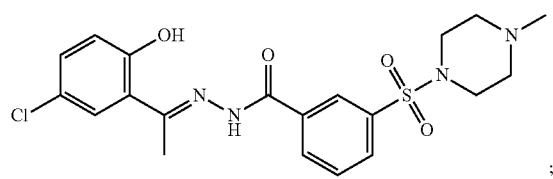 [SMILES: C/C(=N\NC(=O)c1cccc(S(=O)(=O)N2CCN(C)CC2)c1)c1cc(Cl)ccc1O]

or a pharmaceutically acceptable salt thereof.

6. A pharmaceutical composition comprising a therapeutically effective amount of a compound of claim 5 and a pharmaceutically acceptable carrier.

7. A compound having a structure represented by a formula:

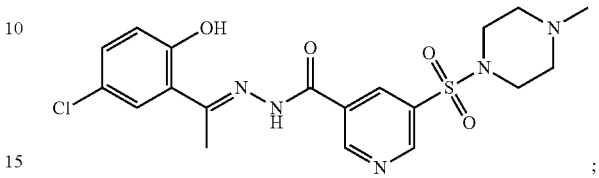

or a pharmaceutically acceptable salt thereof.

8. A pharmaceutical composition comprising a therapeutically effective amount of a compound of claim 7 and a pharmaceutically acceptable carrier.

* * * * *